US012702654B2

(12) United States Patent
Maclean et al.

(10) Patent No.: US 12,702,654 B2
(45) Date of Patent: Aug. 11, 2026

(54) COMPOSITIONS AND METHODS FOR TREATING HOMOCYSTINURIA AND OTHER CONDITIONS USING POLYAMINES

(71) Applicant: THE REGENTS OF THE UNIVERSITY OF COLORADO, Denver, CO (US)

(72) Inventors: Kenneth N. Maclean, Lakewood, CO (US); Hua Jiang, Centennial, CO (US)

(73) Assignee: THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 580 days.

(21) Appl. No.: 18/312,772

(22) Filed: May 5, 2023

(65) Prior Publication Data

US 2023/0270708 A1 Aug. 31, 2023

Related U.S. Application Data

(63) Continuation of application No. PCT/US2021/058107, filed on Nov. 4, 2021.

(60) Provisional application No. 63/109,983, filed on Nov. 5, 2020.

(51) Int. Cl.

| | |
|---|---|
| ***A61K 31/205*** | (2006.01) |
| ***A61K 31/132*** | (2006.01) |
| ***A61K 33/34*** | (2006.01) |
| ***A61P 7/02*** | (2006.01) |

(52) U.S. Cl.

CPC .......... *A61K 31/205* (2013.01); *A61K 31/132* (2013.01); *A61K 33/34* (2013.01); *A61P 7/02* (2018.01)

(58) Field of Classification Search

CPC .... A61K 31/205; A61K 31/732; A61K 31/19; A61K 31/185; A61K 31/195; A61P 7/02; A61P 3/00

See application file for complete search history.

(56) References Cited

U.S. PATENT DOCUMENTS

| | | | |
|---|---|---|---|
| 5,352,440 | A | 10/1994 | Gilchrest et al. |
| 9,895,328 | B2 | 2/2018 | Appling et al. |
| 2004/0213838 | A1 | 10/2004 | Mazer et al. |
| 2008/0267941 | A1 | 10/2008 | Peters et al. |
| 2010/0028334 | A1 | 2/2010 | Cottarel et al. |
| 2018/0326025 | A1 | 11/2018 | Georgiou et al. |
| 2020/0028334 | A1 | 1/2020 | Merke |
| 2022/0096408 | A1 | 3/2022 | Maclean et al. |

FOREIGN PATENT DOCUMENTS

| | | |
|---|---|---|
| CA | 2257559 A1 | 12/1997 |
| WO | WO 89/09258 | 10/1989 |
| WO | WO 2020/210667 | 10/2020 |

OTHER PUBLICATIONS

Soda, K., "Polyamine Metabolism and Gene Methylation in Conjunction with One-Carbon Metabolism," International Journal of Molecular Sciences, Oct. 18, 2018, 35 pages.

Stevens et al. "Quantification of intermediates of the methionine and polyamine metabolism by liquid chromatography-tandem mass spectrometry in cultured tumor cells and liver biopsies" Journal of Chromatography A, 2010, pp. 3282-3288.

Witham et al. "5-Methyl-Tetrahydrofolate and the S-Adenosylmethionine Cycle in C57BL/6J Mouse Tissues: Gender Differences and Effects of Arylamine N-Acetyltransferase-1 Deletion" PLOS One, Oct. 2013, vol. 3, Issue 10, pp. 1-7.

Albert et al., "Impaired osteoblast and osteoclast function characterize the osteoporosis of Snyder-Robinson Syndrome" Orphanet Journal of Rare Disease, 10(27): 1-13, 2015.

Baldensperger et al., "Comprehensive analysis of posttranslational protein modifications in aging of subcellular compartments" Scientific Reports, 10(7596): 1-11, 2020.

Bonaa et al., "Homocysteine lowering and cardiovascular events after acute myocardial infarction" The New England Journal of Medicine, 354: 1578-1588, 2006.

Bradford, "A rapid and sensitive method for the quantitation of microgram quantities of protein utilizing the principle of protein-dye binding" Analytical Biochemistry, 72: 248-254, 1976.

Burgos-Barragan et al., "Mammals divert endogenous genotoxic formaldehyde into one-carbon metabolism" Nature, 548(7669):549-554, 2017.

Chou et al., "Greater protective potent of s-Methyl Cysteine and Syringic Acid Combination for NGF-differentiated PC12 cells against kainic acid-induced injury" International Journal of Medical Sciences, 16(8): 1180-1187, 2019.

Castro et al., "Liver betaine-homocysteine S-methyltransferase activity undergoes a redox switch at the active site zinc" Archives of Biochemistry and Biophysics, 472(1): 26-33, 2008.

(Continued)

*Primary Examiner* — Kevin E Weddington

(74) *Attorney, Agent, or Firm* — MICHAEL BEST & FRIEDRICH LLP

(57) ABSTRACT

Embodiments of the instant disclosure relate to novel compositions and methods for treating a subject having genetic homocystinuria (HCU or other form of genetic homocystinuria). In some embodiments, compositions and methods disclosed herein concern improving efficacy of standard treatments (e.g. trimethylglycine) to reduce dietary compliance requirements and improve outcomes. In accordance with these embodiments, a subject having or suspected of developing classical cystathionine beta-synthase deficient homocystinuria (HCU) or other genetic form of homocystinuria can be treated with a polyamine or diamine or a precursor thereof or a combination thereof for example, in combination with trimethylglycine (e.g. betaine) or other genetic homocystinuria treatment. In other embodiments, a subject having or suspected of developing HCU or other genetic homocystinuria can also be treated with formate or formate derivative, or zinc and/or zinc-containing agent or other standard treatment in combination with a polyamine composition to treat HCU or RD or other form of genetic homocystinuria in the subject.

20 Claims, 23 Drawing Sheets

Specification includes a Sequence Listing.

(56) References Cited

OTHER PUBLICATIONS

Franceschi et al., "Characterization of macrophage phenotype, redox, and purinergic response upon chronic treatment with methionine and methionine sulfoxide in mice" Amino Acids, 52:629-638, 2020.
Corona de la pena et al., "Inhibition of platelet aggregation by putrescine, spermidine, and spermine in hypercholesterolemic rabbits" Archives of Medical Research, 31:546-550, 2000.
Eisenberg et al., "Cardioprotection and lifespan extension by the natural polyamine spermidine" Nature Medicine, 22(12): 1428-1438, 2016.
Husain et al., "Metabolome analysis revealed increase in S-methylcysteine and phosphatidylisopropanolamine synthesis upon L-cysteine deprivation in the anaerobic protozoan parasite Entamoeba histolytica" The Journal of Biological Chemistry, 285(50):39160-39170, 2010.
Hashizume et al., "Epigenetic regulation of the nuclear-coded GCAT and SHMT2 genesconfers human age-associated mitochondrial respiration defects" Scientific Reports, 5:10434, 2015.
Harris et al., "Maternal diet alters exencephaly frequency in SELH/Bc strain mouseembryos" Birth Defects Research Part A, Clinical and Molecular Teratology,73(8): 532-40, 2005.
Iqbal et al., "Folinic acid protects against suppression of growth by methotrexate in mice" Biopharmaceutics & Drug Disposition, 22(4):169-178, 2001.
Imai et al., "Neuroprotective effect of S-allyl-I-cysteine derivatives against endoplasmicreticulum stress-induced cytotoxicity is independent of calpain inhibition" Journal of Pharmacological Sciences, 130: 185-188, 2016.
Jacobs et al., "Cystathionine beta-synthase deficiency alters hepatic phospholipid metabolism: Post-translational repression of phosphatidylethanolamine methyltransferase is a consequence rather than a cause of liver injury in homocystinuria" Molecular genetics and Metabolism, 120: 325-336, 2017.
Wijngaarden et al., "Effect of daily vitamin B-12 and folic acid supplementation on fracture incidence in elderly individuals with an elevated plasma homocysteine concentration: B-Proof, a randomized controlled trial" The American Journal of Clinical Nutrition, 100(6): 1578-1586, 2014.
Jamall et al., "A simple method to determine nanogram levels of 4-hydroxyproline in biological tissues" Analytical Biochemistry, 112:70-75, 1981.
Jamison et al., "Effect of homocysteine lowering on mortality and vascular disease inadvanced chronic kindey disease and end-stage renal disease: a randomized controlled trial" JAMA, 298:1163-70, 2007.
Jiang et al., "Altered hepatic sulfur metabolism in cystathionine beta-synthase deficienthomocystinuria: Regulatory role of taurine upon competing cysteine oxidation pathways" FASEB Journal, 28(9):4044-4054, 2014.
Jiang et al., "Sex-specific dysregulation of cysteine oxidation and the methionine andfolate cycles in female cystathionine gamma-lyase null mice: A serendipitous model of the methylfolate trap." Biology Open, 4:1154-1162, 2015.
Jiang et al., "Altered expression of apoA-IV and PON-1 activity in CBS deficient homocystinuria in the presence and absence of treatment: possible implications for cardiovascular outcomes" Molecular Genetics and Metabolism, 107(1-2): 55-65, 2012.
Kalish et al., "A metabolomic analysis of two intravenous lipid emulsions in a murine model" PLoS One, 8(4): e59653, 2013.
Keating et al., "Constitutive induction of pro-inflammatory and chemotactic cytokines in cystathionine beta-synthase deficient homocystinuria" Molecular genetics and Metabolism, 103(4):330-7, 2011.
Lonn et al., "Homocysteine lowering with folic acid and B vitamins in vascular disease" The New England Journal of Medicine, 354: 1567-77, 2006.
Liu et al., "S-Methyl cysteine enhanced survival of nerve growth factor differentiated PC12 cells under hypoxic conditions" Food & Function, 5: 1125-1133, 2014.
Lamers et al., "Glycine turnover and decarboxylation rate quantified in healthy men and women using primed constant infusions of [1,2-(13C2]glycine and [(2)H3]leucine" The Journal of Nutrition, 137(12): 2647-2652, 2007.
Leung et al., "Folate metabolite profiling of different cell types and embryos suggestsvariation in folate one-carbon metabolism, including developmental changes in human embryonic brain" Molecular and Cellular Biochemistry, 378(1-2): 229-36, 2013.
Heijer et al., "Homocysteine lowering by B vitamins and the secondary prevention ofdeep vein thrombosis and pulmonary embolism: A randomized, placebo-controlled, double-blind trial" Blood, 109(1): 139-44, 2007.
Maclean et al., "Derangement of hepatic polyamine, folate, and methionine cycle metabolism in cystathionine beta-synthase-deficient homocystinuria in the presence and absence of treatment: Possible implications for pathogenesis" Molecular Genetics and Metabolism, 132(2):128-138, 2021.
Maclean et al., "Betaine treatment of cystathionine B-synthase deficient homocystinuria;does it work and can it be improved?" Orphan Drugs: Research and Reviews, 2: 23-33, 2012.
Maclean et al., "Taurine treatment prevents derangement of the hepatic gamma- glutamyl cycle and methylglyoxal metabolism in a mouse model of classical homocystinuria: Regulatory cross-talk between thiol and sulfinic acid metabolism" FASEB Journal, 32(3):1265-1280, 2018.
Maclean et al., "Long-term betaine therapy in a murine model of cystathionine beta- synthase deficient homocystinuria: Decreased efficacy over time reveals a significant threshold effect between elevated homocysteine and thrombotic risk" Molecular genetics and Metabolism, 105(3): 395-403, 2012.
Maclean et al., "Taurine alleviates repression of betaine-homocysteine S- methyltransferase and significantly improves the efficacy of long-term betaine treatment in a mouse model of cystathionine B-synthase-deficient homocystinuria" The FASEB Journal, 33(5): 6339-6353, 2019.
Maclean et al., "Cystathionine Beta-Synthase Null Homocystinuric Mice Fail To ExhibitAltered Hemostasis Or Lowering Of Plasma Homocysteine In Response To Betaine Treatment", Molecular Genetics and Metabolism, 101(2-3): 163-171, 2010.
Maclean et al., "High homocysteine and thrombosis without connective tissue disordersare associated with a novel class of cystathionine beta-synthase (CBS) mutations" Human Mutation, 19(6): 629-40, 2002.
Maclean et al., "A Novel Transgenic Mouse Model Of CBS-Deficient Homocystinuria Does Not Incur Hepatic Steatosis Or Fibrosis And Exhibits A Hypercoagulative Phenotype That Is Ameliorated By Betaine Treatment", Molecular Genetics and Metabolism, 101(2-3): 153-162, 2010.
Malouf et al., "Folic acid with or without vitamin B12 for cognition and dementia [Cochrane Review]" Cochrane Database of Systematic Reviews, 4: CD004514, 2004.
Madeo et al., "Nutritional Aspects of Spermidine" Annual Review of Nutrition, 40: 13.1-13.25, 2020.
Mudd et al., "Disorders of Transsulfuration—Chapter 35" The Online Metabolic and Molecular Bases of Inherited Disease McGraw-Hill Education, 1279-1327, 2019.
Mudd et al., "The natural history of homocystinuria due to cystathionine b-synthase deficiency" American Journal of Human Genetics, 37: 1-31, 1985.
Miller et al., "Conformation-dependent inactivation of human betaine-homocysteine S-methyltransferase by hydrogen peroxide in vitro" The Biochemical Journal, 392: 443-448, 2005.
Moreno et al., "Differential neuroprotective effects of 5'-deoxy-5'-methylthioadenosine" PLoS One, 9(3):e90671, 2014.
Naughten et al., "Homocystinuria due to cystathionine beta-synthase deficiency in Ireland: 25 years' experience of a newborn screened and treated population with reference to clinical outcome and biochemical control" Journal of Inherited Metabolic Disease, 21(7): 738-747, 1998.

(56) References Cited

OTHER PUBLICATIONS

Pakala, "Inhibition of arterial thrombosis by polyamines in a canine coronary artery injury model" Thrombosis Research, 110: 47-51, 2003.
Pakala, "Effect of polyamines on in vitro platelet aggregation and in vivo thrombus formation" Cardiovascular Radiation Medicine, 3: 213-220, 2002.
Pontel et al., "Endogenous Formaldehyde is a Hematopoietic Stem Cell Genotoxin and Metabolic Carcinogen" Molecular Cell, 60(1): 177-88, 2015.
Rosenblatt et al., Inherited disorders of folate and cobalamin transport and metabolism,in: B.A. Seriver CR, Sly WS, Valle D (Ed.), The metabolic and molecular bases of inherited disease McGraw-Hill Professional, New York, 2001, pp. 3897-3933.
Rosenblatt, "Chapter 9 Inherited Disorders of folate and cobalamin" Graham et al., (eds.) Homocysteine Metabolism: From Basic Science to Clinical Medicine, 61-68, 1997.
Soares et al., "High levels of methionine and methionine sulfoxide: Impact on adeninenucleotide hydrolysis and redox status in platelets and serum of young rats" Journal of Cellular Biochemistry, 1-15, 2018.
Tang et al., "5'-Methylthioadenosine attenuates ischemia reperfusion injury after liver transplantation in rats" Inflammation, 37:1366-1373, 2014.
Tani et al., "Mice deficient in the Shmt2 gene have mitochondrial respiration defects and are embryonic lethal" Scientific Reports, 8:425, 2018.
Green et al., "Lowering homocysteine with B vitamins has No. effect on biomarkers ofbone turnover in older persons: a 2-y randomized controlled trial" American Journal of Clinical Nutrition, 85(2): 460-4, 2007.
Toole et al., "Lowering homocysteine in patients with ischemic stroke to preventrecurrent stroke, myocardial infarction, and death: the Vitamin Intervention for Stroke Prevention (VISP) randomized controlled trial" JAMA, 291:565-75, 2004.
Tibbetts et al., "Compartmentalization of Mammalian folate-mediated one-carbon metabolism" Annual Review of Nutrition, vol. 30: 57-81, 2010.
Rebeille et al., "Methionine catabolismin *Arabidopsis* cells is initiated by a gamma-cleavage process and leads to S-methylcysteine and isoleucine syntheses" PNAS, 103(42): 15687-15692, 2006.
Oliai et al., "Long-term effects of folic acid and vitamin-B12 supplementation on fracturerisk and cardiovascular disease: Extended follow-up of the B-PROOF trial" Clinical Nutrition, 40: 1199-1206, 2021.
Anonymous, "The role of prebiotics in the management of inflammatory boweldiseases." Interview with Dr.Francisco Guamer, An ORAFTI Newsletter, No. 10—Summer 2004, 16 pages.
Kumar et al. "Homocystinuria: Therapeutic approach", Clinica Chimica Acta, 458: 55-62, 2016.
Maclean, "Manipulating folate metabolism achieves near-normal homocysteine withoutmethionine restriction in homocystinuric mice", Journal of Inherited Metabolic Disease, vol. 42, No. S1, pp. 13-14, 2019.
Van Hove et al., "Biomarkers of oxidative stress, inflammation and vascular dysfunction in inherited cystathionine beta-synthase deficient homocystinuria and the impact of taurine treatment in a phase 1/2 human clinical trial" Journal of Inherited Metabolic Disease, 42: 424-437, 2019.
Pascale et al., "Chemoprevention of hepatocarcinogenesis: S-adenosyl-L-methionine" Alcohol, 27:193-198, 2002.
Pai et al., "Glycine decarboxylase deficiency causes neural tube defects and features of non-ketotic hyperglycinemia in mice", Nature Communications, 6(6388): 1-11, 2015.
Yap et al., "Vascular outcome in patients with homocystinuria due to cystathionine beta-synthase deficiency treated chronically; a multicenter observational study" Arteriosclerosis, Thrombosis, and Vascular Biology, 21(12):2080-2085, 2001.
Maclean et al., "Cystathionine protects against endoplasmic reticulum Stress-inducedLipid Accumulation, Tissue Injury, and Apoptotic Cell Death" The Journal of Biological Chemistry,287(38): 31994-32005, 2012.

DHFR

+ NADPH + $H^+$ ⟶ + $NADP^+$

Dihydrofolate

THF

Fig. 4A
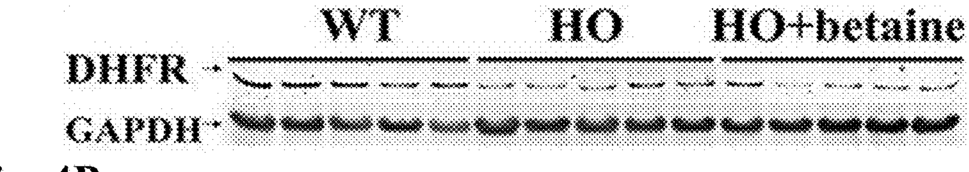
Fig. 4B
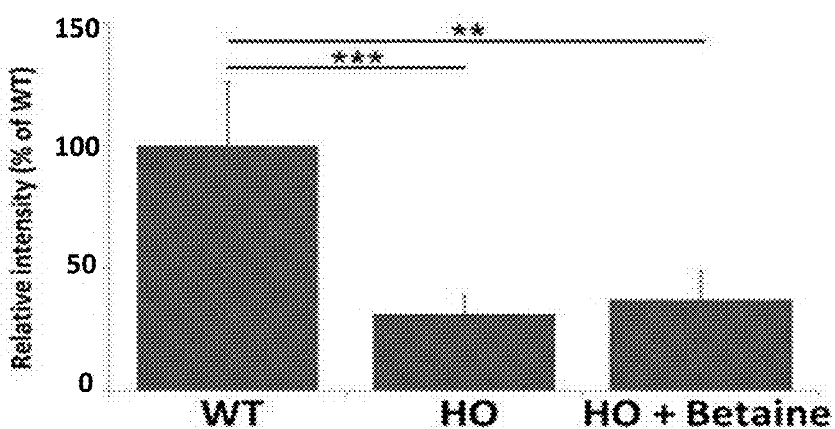
Fig. 5
10-FormylTHF
Purines
ALDH1L1
5,10-MethenylTHF
Thymidylate
THF
Serine
SHMT
Glycine
5,10-MethyleneTHF
Methionine
5,10-MethylTHF Fig. 9A
Fig. 9B
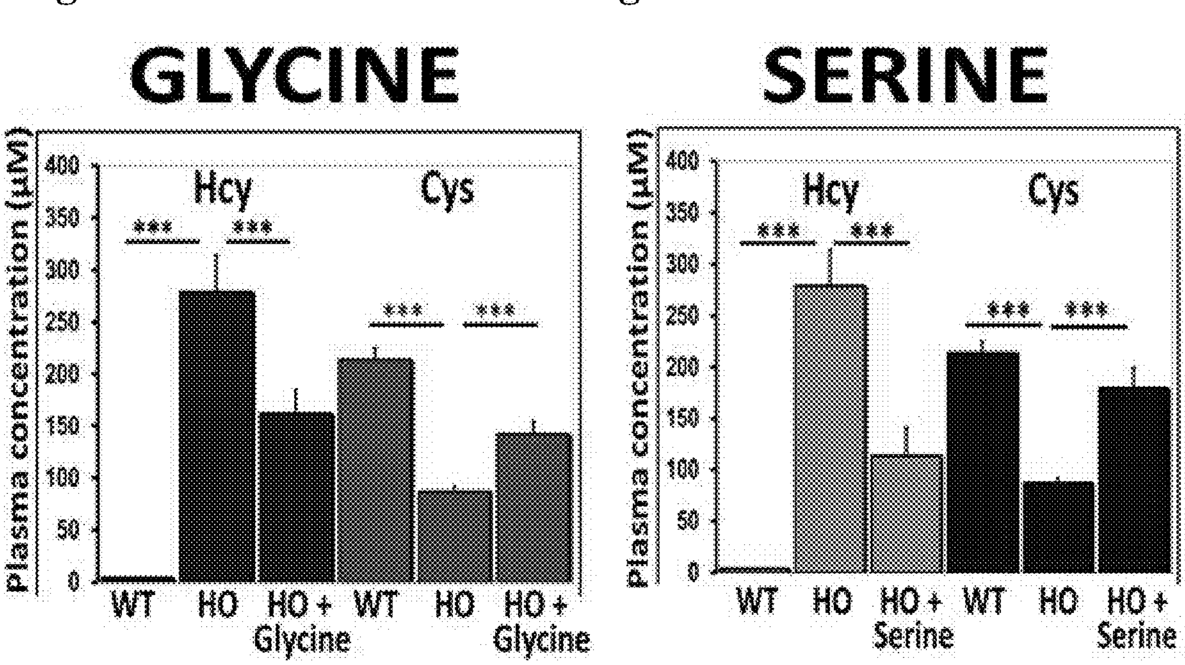
Fig. 10
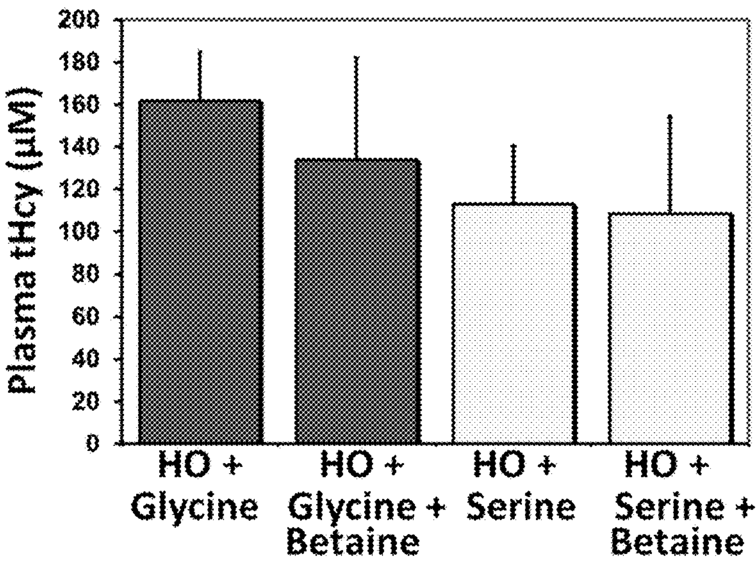

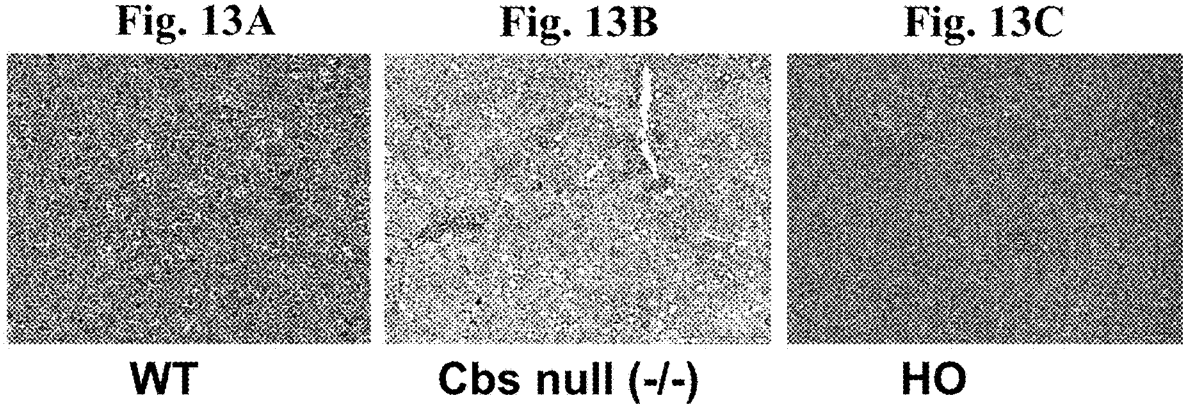
Fig. 14
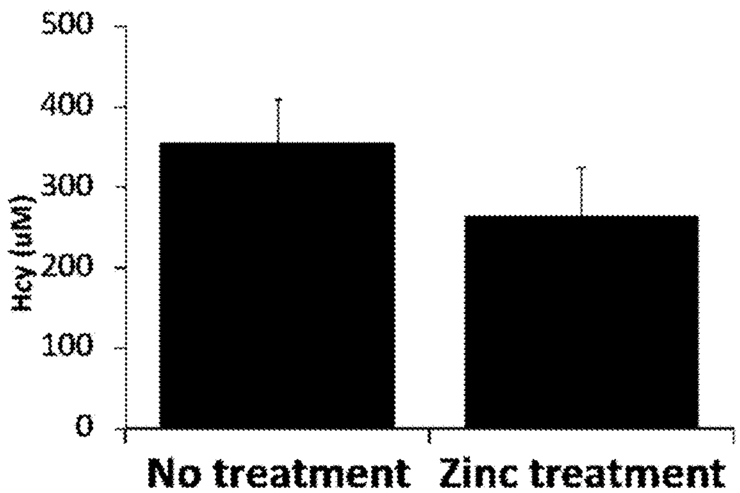

| Metabolites | HO vs WT | HO Bet vs WT | HO vs HO Bet |
|---|---|---|---|
| methionine | 131 | 138 | NS |
| N-acetylmethionine | 273 | 168 | -38 |
| N-formylmethionine | 230 | 238 | NS |
| methionine sulfoxide | 283 | 218 | NS |
| S-adenosylmethionine (SAM) | 195 | 303 | NS |
| S-adenosylhomocysteine (SAH) | 699 | 1290 | NS |
| homocysteine | 1142 | 8911 | -22 |
| cysteine | -42 | NS | 158 |
| N-acetylcysteine | -77 | NS | 297 |
| S-methylcysteine | 347 | 400 | NS |
| hypotaurine | -68 | NS | 172 |
| N-acetyltaurine | 321 | 377 | NS |
| taurocyamine | 166 | 155 | NS |

Fig. 21A
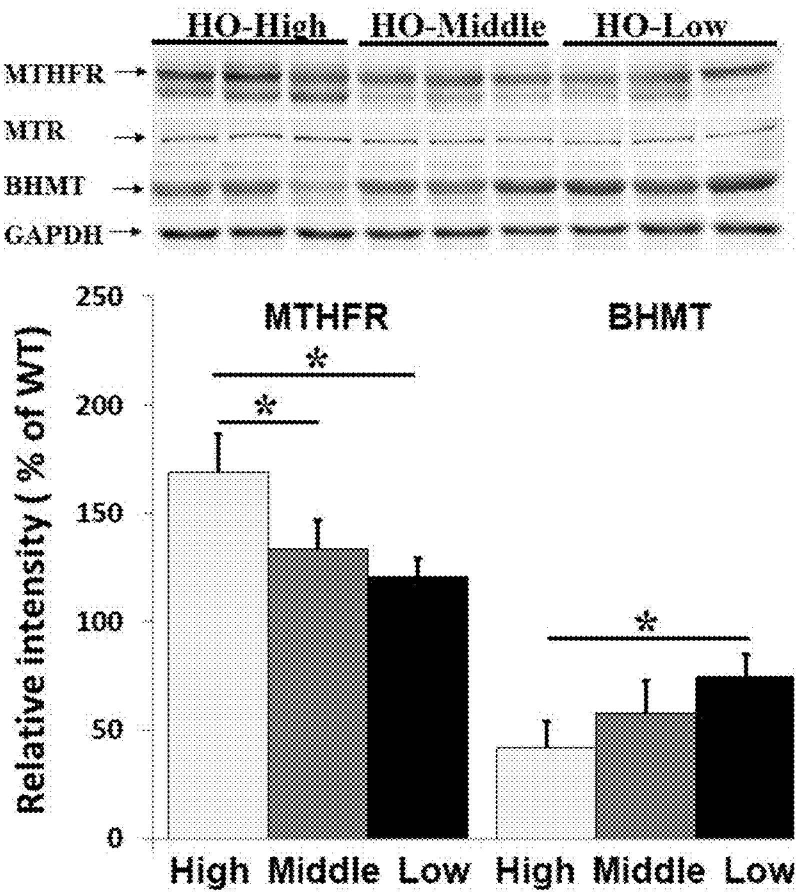
Fig. 21B
Fig. 21C
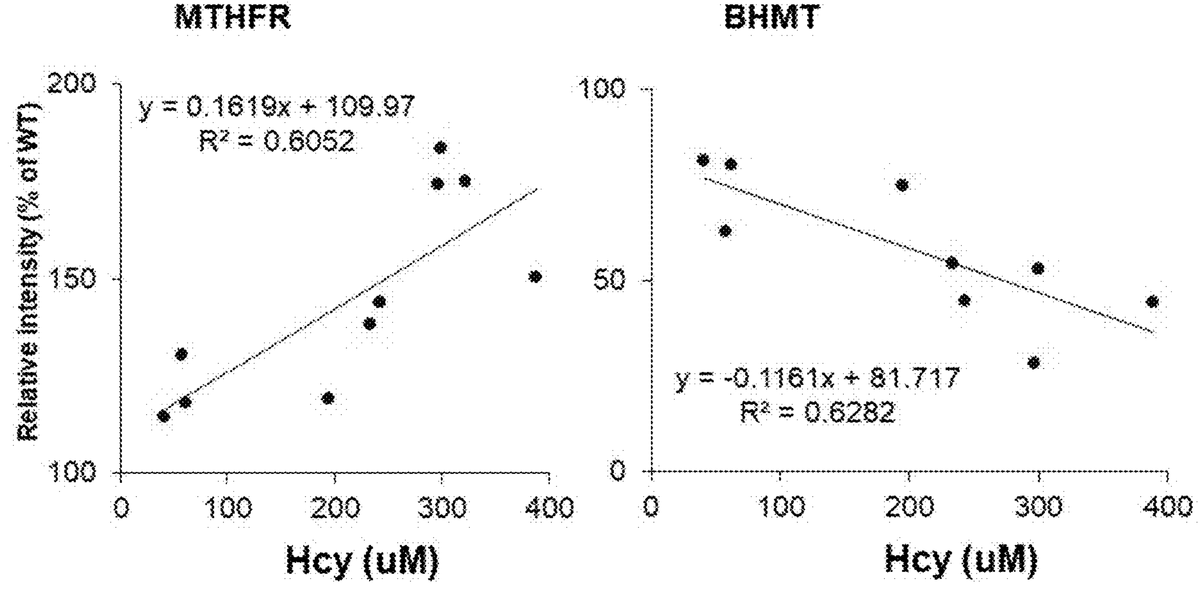

Figures 22A, 22B, 22C:
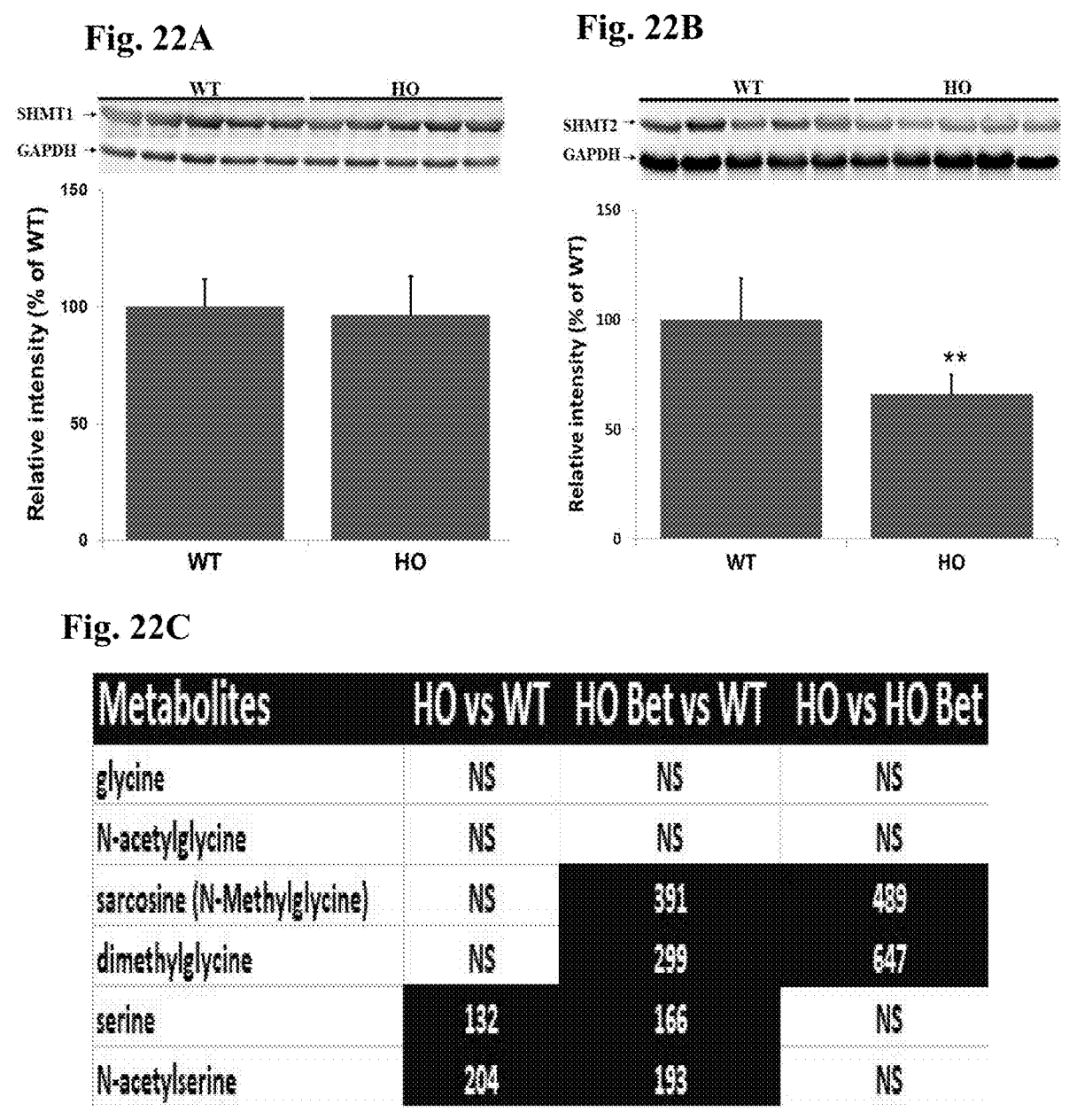

| Metabolites | HO vs WT | HO Bet vs WT | HO vs HO Bet |
|---|---|---|---|
| glycine | NS | NS | NS |
| N-acetylglycine | NS | NS | NS |
| sarcosine (N-Methylglycine) | NS | 391 | 489 |
| dimethylglycine | NS | 299 | 647 |
| serine | 132 | 166 | NS |
| N-acetylserine | 204 | 193 | NS |

Fig. 23A
Fig. 23B
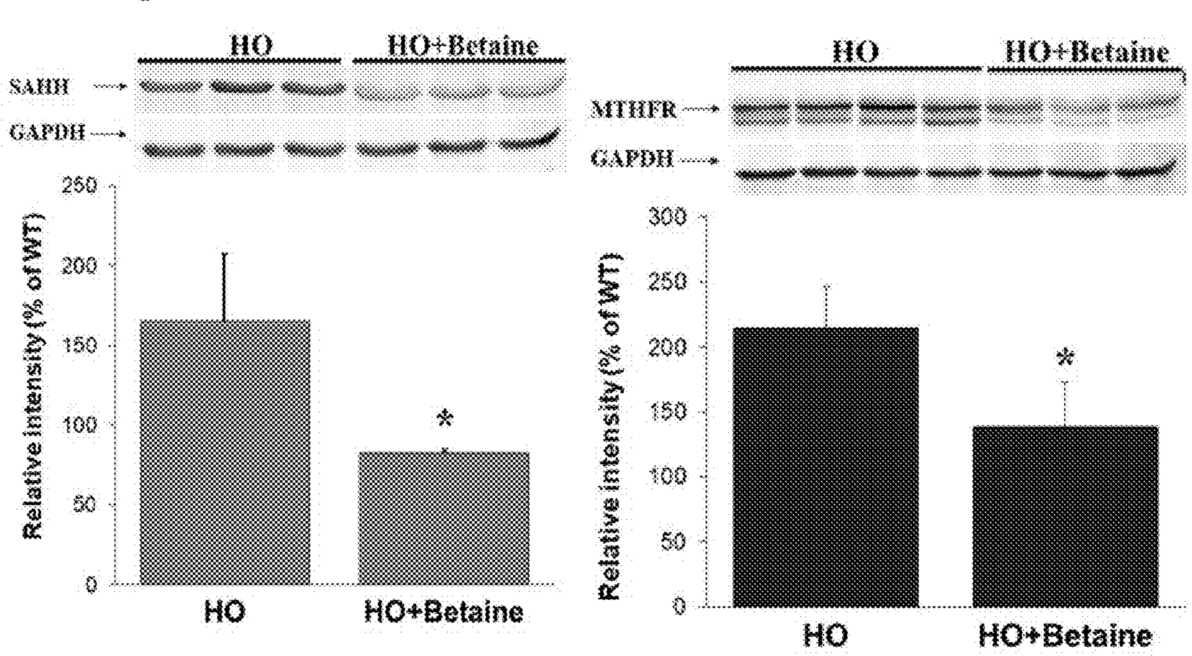
Fig. 23C
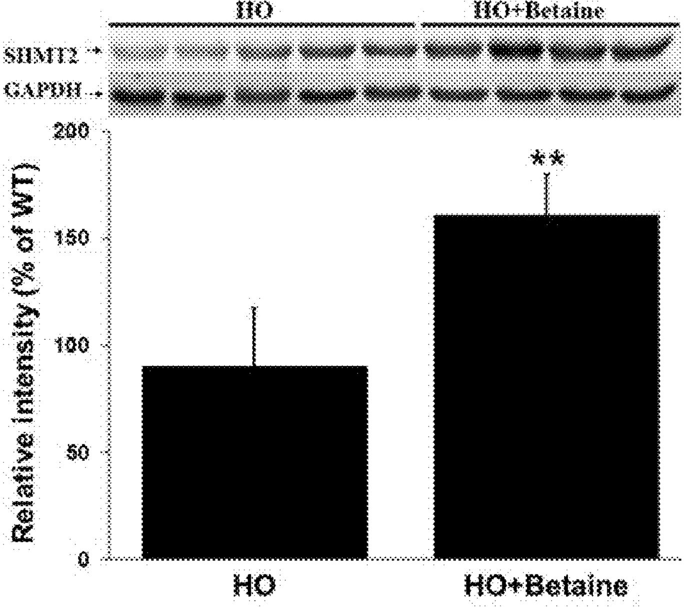

Fig. 23D
Fig. 23E
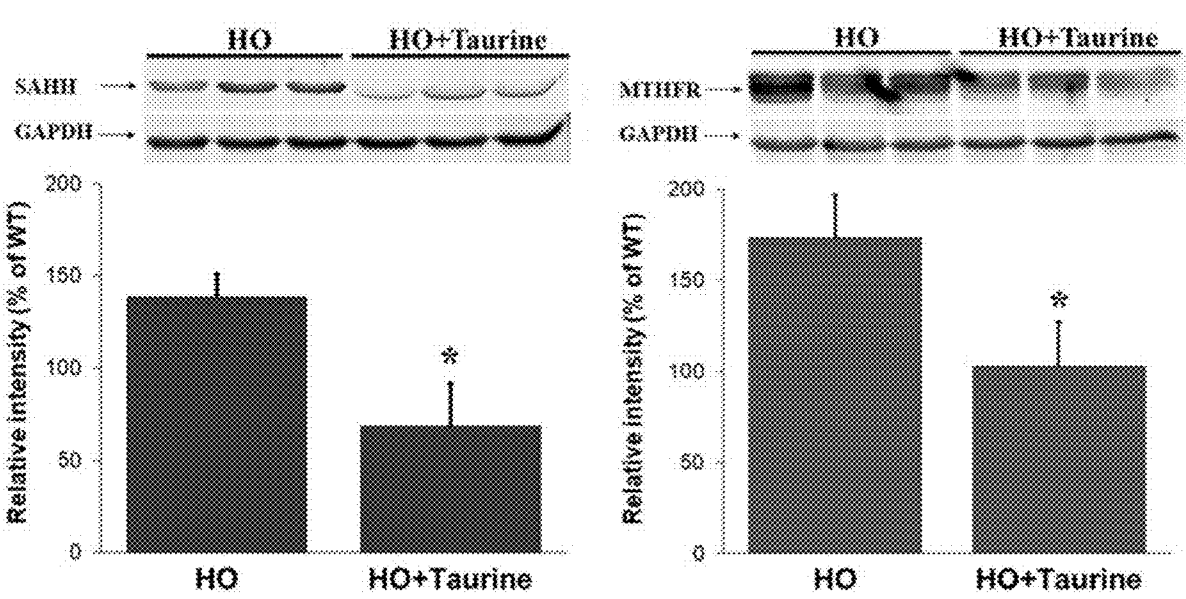
Fig. 23F
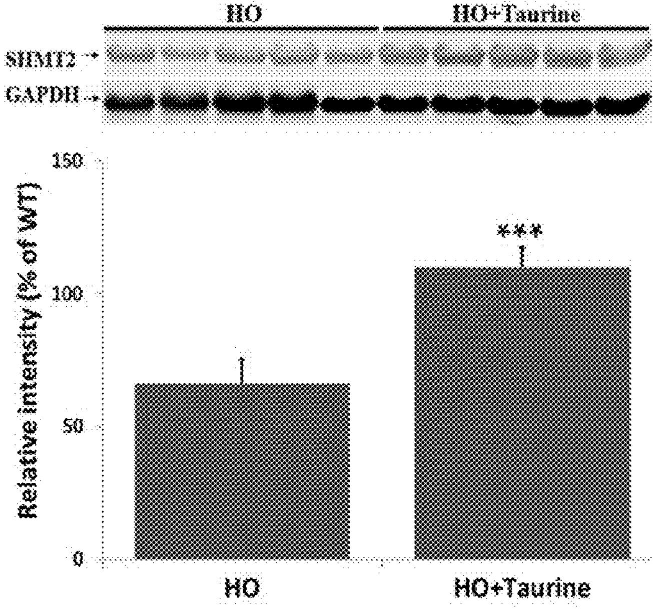

| | Homocystinuria | |
|---|---|---|
| | CBS Deficient | MTR Deficient |
| Plasma tHcy (μM) | 285 (22.8) 57-fold increase | 220 (38.4) 44-fold increase |
| SAHH | Induced ↑ | Repressed ↓ |
| MTHFR | Induced ↑ | Repressed ↓ |
| BHMT | Repressed ↓ | Induced ↑ |

COMPOSITIONS AND METHODS FOR TREATING HOMOCYSTINURIA AND OTHER CONDITIONS USING POLYAMINES

PRIORITY

This application is a Continuation of International Application No. PCT/US2021/058107 filed Nov. 4, 2021, which claims priority to U.S. Provisional Application No. 63/109,983 filed Nov. 5, 2020. The provisional application and the international application are each incorporated herein by reference in their entireties for all purposes.

STATEMENT REGARDING SEQUENCE LISTING

The instant application contains a Sequence Listing which was submitted via ASCII copy created on Nov. 3, 2021 and filed with PCT/US2021/058107 was converted on May 5, 2023 to reflect the required XML format, now referred to as '2023-05-05_CU5464H-US1_SequenceListing.xml' that is 17 kilobytes (KB) in size having 12 sequences and is incorporated herein in its entirety for all purposes.

FIELD

Embodiments of the instant disclosure relate to novel compositions and methods for treating a subject having the condition of genetic homocystinuria. In accordance with these embodiments, a subject having or suspected of developing a genetic homocystinuria can be treated with a polyamine or a diamine or a precursor thereof, or a combination thereof for example, in combination with trimethylglycine (e.g. betaine) or other genetic homocystinuria treatments to improve outcome and reduce side effects of these conditions.

BACKGROUND

Homocystinuria is a disorder in which the body is unable to process certain amino acids and homocysteine accumulates. Other forms of homocystinurias exist. Genetic homocystinurias can be due to deficiency of cystathionine beta-synthase (HCU). Homocystinuria can also occur due to genetic mutation impairing the remethylation of homocysteine back to methionine. Such remethylation disorders (RD) include inactivating mutations in methionine synthase or defects in the metabolism/transport of the methionine synthase co-factor cobalamin. HCU can be a side effect of an autosomal recessive disorder of sulfur amino acid metabolism such as methionine and is commonly caused by a deficiency in cystathionine β-synthase (CBS). This enzyme sits at the branch point between the methionine cycle and transsulfuration and catalyzes the condensation of serine and homocysteine (Hcy) into cystathionine which is subsequently converted to cysteine by cystathionine-lyase (CGL). Homocystinurias lead to a multi-systemic disorder of the connective tissue, central nervous system (CNS), and cardiovascular system. In human patients, HCU, for example, is characterized by a range of connective tissue disturbances, mental retardation, and a dramatically increased incidence of vascular disorders particularly thromboembolic disease. One major cause of death in HCU patients is cardiovascular complications. It is estimated that untreated patient with the severest form of this disease have about a 27% chance of having a thrombotic event by the age of 15. Hereditary metabolic disorders are caused by accumulation of homocysteine in serum and an increased excretion of homocysteine in the urine. Typical treatment for severe CBS deficient HCU involves lowering homocysteine (Hcy) levels by a combination of restricting dietary intake of methionine with a protein-restricted diet and remethylating Hcy with betaine treatment. While this regimen is effective, compliance with a methionine-restricted diet is typically poor. In addition, efficacy of betaine treatment for lowering plasma and tissue levels of Hcy significantly diminishes over time. Therefore, other more effective treatments are needed.

SUMMARY

Embodiments of the instant disclosure relate to novel compositions, methods and uses for treating a subject having homocystinuria to improve clinical outcomes. In some embodiments, compositions and methods disclosed herein concern improving efficacy of existing treatments. In accordance with this embodiment, compositions disclosed herein can be used alone or combined with standard treatments of genetic homocystinurias or similar condition to improve outcomes. In certain embodiments, compositions containing one or more polyamine can be used to treat homocystinurias (e.g. HCU), other genetic forms of homocystinuria (for example, having a level of Hcy of 70 μM or greater) and reduce the need for dietary compliance requirements for improved outcomes of the condition in the subject.

In certain embodiments, compositions to treat a subject having HCU or another form of genetic homocystinuria in a subject can include an effective amount of a polyamine or diamine thereof, a salt thereof, a polyamine or diamine derivative or polyamine or diamine precursor or prodrug agent, pectin, conjugate thereof or a recombinant microorganism (e.g. bacteria) capable of producing one or more polyamines or diamines of use as a single agent. In certain embodiments, the polyamine can include, putrescine, spermidine, spermine, a polyamine derivative (e.g. hypuscine) or a combination thereof. In other embodiments, a polyamine or diamine thereof, a salt thereof, a polyamine or diamine derivative or polyamine or diamine precursor or prodrug agent, pectin or a recombinant bacteria capable of producing one or more polyamines or diamines can be used to treat a subject in combination with other agents such as standard agents or other agents disclosed herein (e.g. betaine, taurine, formate or formate derivative, zinc, copper) to lower homocysteine (Hcy) levels in a subject having HCU, or other form of genetic homocystinuria, or similar condition over-producing homocysteine.

In other embodiments, spermidine synthase and/or spermine synthase or other relevant enzyme can be induced in a subject to increase polyamine production in order to lower homocysteine (Hcy) levels in a subject having HCU, or other form of genetic homocystinuria, or similar condition over-producing homocysteine. In accordance with these embodiments, compositions to treat aberrant Hcy levels can include an effective amount of a polyamine such as spermine or spermidine or a diamine such as putrescine or cadavarine or hypusine or other polyamine or polyamine derivative, a salt thereof or polyamine precursor or prodrug agent to lower homocysteine (Hcy) levels in a subject. In certain embodiments, a polyamine derivative or other agent can include an analog. In some embodiments, other suitable form of polyamine or combination agents with polyamine can be provided to a subject to improve bioavailability of polyamines or polyamine derivatives to treat a health condition disclosed herein.

In certain embodiments, the concentration of polyamines or diamines or derivatives thereof administered to a subject can be about 0.05 mg/kg to about 100.0 mg/kg; or about 0.05 mg/kg to about 80 mg/kg; or about 0.1 mg/kg to about 70 mg/kg: or 0.1 mg/kg to about 60 mg/kg; or 0.1 mg/kg to about 50 mg/kg; or about 0.1 mg/kg to about 40 mg·kg, about 2-4 times per day, about 2-3 times per day, daily, every other day, weekly, or other suitable administration schedule. In certain embodiments, a subject can consume these supplements 1 time to about 3 times per day; for example, at mealtime. It is contemplated that any treatment regimen known in the art can be used. In certain embodiments, polyamine or diamine or derivatives thereof can be given with food alone or in combination with other agents to treat HCU or other form of genetic homocystinuria in a subject.

In certain embodiments, one or more polyamine or polyamine-containing agent can be combined with standard HCU/RD or standard treatments for other forms of genetic homocystinuria or other agents to lower homocysteine (Hcy) levels in a subject. In some embodiments, a formate or formate derivative as indicated herein can be combined with or provided separately from, a polyamine (e.g. spermidine, spermine), diamine, or derivative thereof to the subject before, at the time of or after administering the polyamine, diamine, or derivative thereof to the subject. In other embodiments, zinc or zinc conjugate (and/or copper agent) as indicated herein can be combined with or provided separately from, a polyamine, diamine, or derivative thereof to the subject before, at the time of or after administering the polyamine, diamine, or derivative thereof to the subject. In some embodiments, a polyamine, a diamine, or derivative thereof as disclosed herein (e.g. at the same or different time) can be combined with any standard treatment; for example, trimethylglycine (e.g. betaine) where trimethylglycine can be administered to a subject at standard concentrations as noted above at the time of administering a polyamine or diamine or derivative thereof in a composition. In some embodiments, administration of any agent or combination of agents contemplated herein to treat HCU or other form of genetic homocystinuria or related condition can be during one or more meal.

In other embodiments, compositions contemplated herein can include a pharmaceutically acceptable formulation of one or more polyamines, diamines, polyamine derivative, or diamine derivative, a salt thereof (e.g. ammonium spermine, ammonium spermidine, spermidine trihydrochloride, spermine dihydrochloride, etc.), a polyamine or diamine derivative or polyamine or diamine precursor or prodrug agent for administration to a subject. In some embodiments, one or more polyamines of use herein can be produced by microorganisms or generated synthetically. In certain embodiments, compositions can include zinc or a zinc conjugate (and optionally a copper supplement) or other acceptable zinc delivery agent in combination with a polyamine, diamine, or polyamine or diamine prodrug disclosed herein. In yet other embodiments, compositions contemplated herein can include polyamines and/or zinc (and optionally, copper) and/or a standard treatment for HCU/RD or standard treatments for other forms of genetic homocystinuria such as trimethylglycine (e.g. betaine) or combinations thereof for optimal treatment. In certain embodiments, a polyamine- or diamine-containing compositions can be combined with a standard treatment for homocystinuria, (e.g. HCU) such as trimethylglycine (e.g. betaine, such as an anhydrous betaine, betaine hydrochloride). Modes of administration for these compositions can include any mode suitable for delivery of such agents such as oral administration (e.g. by tablet, liquid or hydratable powder or supplement), intravenously, intrarectally, or subcutaneously administered or other mode of administration.

In certain embodiments, polyamine or diamine combination regimens can include formate or formate derivative. Formate or formate derivative contemplated herein can be administered to a subject at about 0.5 mg/kg to about 100.0 mg/kg; or about 2.0 mg/kg to about 80 mg/kg; or about 3.0 mg/kg to about 70 mg/kg: or 4.0 mg/kg to about 60 mg/kg; or 5.0 mg/kg to about 50 mg/kg, 2-4 times per day, daily, every other day, weekly, or other suitable dosing regimen.

In some embodiments, a subject contemplated herein has homocystinuria (HCU) but not hyperhomocysteinemia. In some embodiments, a subject has genetic HCU or other genetic forms of homocystinuria such a RD or other genetic form of homocystinuria (for example, a subject having a level of Hcy of 70 μM or greater). In some embodiments, the subject has been taking betaine, but the betaine treatments have become less effect or ineffective. In certain embodiments, a subject contemplated herein is not folate deficient, folate resistant or a subject having limited ability to absorb or metabolize folic acid (e.g. folate deficient-related condition). In other embodiments, the subject is a young child, adolescent or adult. In some embodiments, the subject is not a pregnant female and/or not a neonate. In other embodiments, a subject contemplated herein having HCU (e.g. genetic HCU) or other genetic form of homocystinuria has a blood homocysteine level of about 70 μM to about 450 μM, or about 100 μM to about 450 μM, or about 150 μM to about 450 μM, or about 200 μM to about 400 μM, or about 250 μM to about 400 μM which differs from a subject having hyperhomocysteinemia. A subject having hyperhomocysteinemia can differ from a subject having genetic HCU where a subject having hyperhomocysteinuria can have a level of blood homocysteine above 15 μM or blood homocysteine can differ by about 15 μM to 50 μM or less than 70 μM. One of skill in the art recognizes the difference between these conditions. It is recognized by one of skill in the art that hyperhomocysteinemia is typically managed with vitamin B6, folic acid, and vitamin B12 supplementation which fails to treat HCU/RD or other forms of genetic homocytinuria contemplate herein.

In some embodiments, compositions to treat homocystinuria can include an effective amount of one or more polyamine composition in combination with formate, a salt thereof (e.g. sodium formate), a formate derivative or formate precursor or prodrug agent to lower homocysteine (Hcy) levels in a subject. In certain embodiments, compositions disclosed herein can include administering pectin known to produce formate by intestinal fermentation in the microbiome; for example, administering at mealtime or in a gradual release form over several minutes, hours or more. In other embodiments, a subject can be treated with a microorganism (e.g. a probiotic bacteria or other organism capable of producing formate or formate derivative). In other embodiments, administration of one or more polyamine, diamine or derivative thereof as disclosed herein can be combined with at least one of taurine and n-acetylcysteine, or other equivalent in order to boost glutathione availability for formaldehyde detoxification for a more effective treatment with reduced side effects. In accordance with these embodiments, taurine concentration can be about 10 mg/kg to about 300 mgs/kg; or about 20 mg/kg to about 250 mgs/kg; or about 30 mg/kg to about 200 mgs/kg; or about 50 mg/kg to about 150 mgs/kg provided daily, two or more times per day, every other day or other appropriate dosing regimen separate from or in the same compositions as the other agents. In other embodiments, N-acetylcysteine concentration can be about 20 mg/kg to about 300 mgs/kg; or about 30 mg/kg to about 250 mgs/kg; or about 40 mg/kg to about 200 mgs/kg; or about 100 mg/kg to about 180 mgs/kg provided daily, two or more times per day, every other day or other appropriate dosing regimen separate from or in the same compositions as the other agents.

In certain embodiments, compositions disclosed herein can be administered to a subject having a genetic form of homocystinuria (e.g. HCU or other genetic forms of homocystinuria (e.g. RD)) can be treated with combinations of polyamines or diamines and zinc, mixed or administered separately. In some embodiments, zinc or a zinc conjugate or other acceptable zinc delivery agent can be administered to a subject can be about 1.0 mgs to about 150 mgs daily or every other day or other appropriate dosing regimen; or about 2.0 mgs to about 100 mgs daily or every other day; or about 3.0 mgs to about 80 mgs daily or every other day; or about 4.0 mgs to about 70 mgs daily or every other day; or about 5.0 mgs to about 60 mgs daily or every other day; or about 35 mg to 60 mgs per day for an adult or about 2 mgs to about 10 mgs for an infant or about 15 mgs to about 35 mgs for a child or adolescent.

In other embodiments, composition including polyamines or diamine or polyamine conjugate or derivative or precursor can be combined with standard treatments, for example administered before, after or at the time of administering (e.g. simultaneously) trimethylglycine (e.g. betaine) where trimethylglycine can be administered to a subject at standard concentrations. In accordance with these embodiments, trimethylglycine (e.g. betaine) can be administered or taken at about 10 mg/kg to about 200 mg/kg; or about 20 mg/kg to about 150 mg/kg; or 30 mg/kg to about 100 mg/kg; or 40 mg/kg to about 80 mg/kg; or about 50 mg/kg 2-4 times per day, daily, every other day, weekly, or other suitable administration schedule to the subject. In accordance with these embodiments, trimethylglycine can be administered in doses of about 20 mg/kg to about 200 mg/kg or about 50 mg/kg to about 150 mg/kg as a single administration or multiple administrations to a subject having homocystinuria (e.g. HCU or other genetic form of homocystinuria) or at mealtime where the dose is tailored to the number of times taken per day to about 1.0 gram to about a 40.0 gm total per subject daily. In certain compositions disclosed herein, an effective amount of trimethylglycine (e.g. betaine) in a composition separate from or in combination with polyamines or derivatives disclosed herein with about 1.0% to about 3% w/v or about 2% w/v concentration of trimethylglycine (e.g. betaine) in solution (e.g. water or other acceptable medium or excipient). In other embodiments, polyamines, diamines or conjugates or derivatives thereof can be combined with amino acid supplements or derivatives thereof such as glycine, serine, histidine or methylglycine or other suitable amino acid to reduce homocysteine levels and treat homocystinuria in the subject.

In some embodiments, compositions or formulations disclosed herein can be administered in powder form, tablet, by microparticle, in a slow or time-release microparticle in a solid or a liquid or other suitable format or other known time-delivery method. In certain embodiments, an effective amount of a composition or formulation can be administered for homocystinuria management (e.g., for a subject's lifetime).

In certain embodiments, one or more polyamine or polyamine-containing agent can be combined with standard HCU/RD or other treatments for genetic homocystinuria or other agents to lower homocysteine (Hcy) levels in a subject. In some embodiments, a formate or formate derivative as indicated herein can be combined with or provided separately from, a polyamine, diamine, or derivative thereof to the subject before, at the time of or after administering the polyamine, diamine, or derivative thereof to the subject. In certain embodiments, a formate derivative or other agent can include a formate prodrug esterified to glycerol, for example, diformylglycerol, triformylglycerol (e.g. triformin) in an oil form, or other suitable form or combined with one or more excipients to improve bioavailability of formate or formate derivative. Alternatively, a formate derivative or prodrug contemplated herein can include a diformylglycerol-glucose conjugate or diformylglycerophosphocholine, diformylglycerophosphoethanolamine, or as a mixed glycerol ester, or other suitable form or combined with one or more excipients to improve bioavailability. In certain embodiments, compositions disclosed herein can include administering pectin known to produce formate by intestinal fermentation in the microbiome, for example administering at mealtime or in a gradual release form over several minutes, hours or more. In other embodiments, a subject can be treated with a microorganism (e.g. a probiotic bacteria or other organism capable of producing formate or formate derivative). In certain embodiments, the concentration of formate or formate derivative contemplated herein can be administered to a subject at about 0.5 mg/kg to about 100.0 mg/kg; or about 2.0 mg/kg to about 80 mg/kg; or about 3.0 mg/kg to about 70 mg/kg: or 4.0 mg/kg to about 60 mg/kg; or 5.0 mg/kg to about 50 mg/kg, 2-4 times per day, daily, every other day, weekly, or other suitable dosing regimen.

Other embodiments disclosed herein contemplate treating a subject having HCU or other form of genetic homocystinuria or related condition with a regimen for a predetermined period of time and then changing or adjusting the treatment in order to avoid waning or lessening effects of the regimen. In accordance with these embodiments, a standard treatment such as trimethylglycine (e.g. betaine) in combination with polyamines and optionally, formate, and/or zinc (and/or copper) and/or polyamines/diamines to treat a subject. Then after a period of about a week, two weeks or more, a month, 2 months or more, 6 months or about a year, treatment regimens can be adjusted to use differing agents or combinations of agents disclosed herein in order to treat the subject and reduce dietary restraints and prolong treatment efficacy to avoid side effects of the HCU or other related genetic condition in a subject in need thereof.

Some embodiments disclosed herein concern kits that can include compositions disclosed herein for treating Hcy overproduction or modifying homocysteine production in a subject. In certain embodiments, kits can include capsules, microparticles, powders, liquid compositions, or tablet forms of the one or more compositions disclosed herein for ready administration or consumption by the subject for treating the disorder. In other embodiments, kits contemplated herein can include single agents, combinations of agents in a single formulation or separate agents. In yet other embodiments, agents of use to treat Hcy overproduction in a subject contemplated herein can include food additives for applying to a food or formulations to be added to a liquid to be consumed by a subject in need thereof.

BRIEF DESCRIPTION OF THE DRAWINGS

FIGS. 4A-4B represent a Western blot comparing the level of DHFR and GAPDH (control) for wild type (WT), treated (HO+betaine) and untreated mice (HO) using the HCU mouse model (FIG. 4A); and further illustrating in a bar graph (FIG. 4B), level of intensity of DHFR for wild type (WT), treated (HO+betaine) and untreated mice (HO) using the HCU mouse model in certain embodiments disclosed herein.

FIG. 5 is a schematic of a pathway where 10-formyltetrahydrofolate dehydrogenase ALDH1l1 catalyzes conversion of 10-formyltetrahydrofolate, NADP, and water to tetrahydrofolate (THF), NADPH, and carbon dioxide to generate methionine and other agents in certain embodiments disclosed herein.

FIGS. 9A-9B represent a bar graph illustrating level of homocysteine (Hcy) versus cysteine (Cys) for wild type (WT), untreated (HO) and treated (HO+glycine) (FIG. 9A); represents a bar graph (9B) of level of homocysteine versus cysteine for wild type (WT), untreated (HO) and treated (HO+serine) (FIG. 9B) of the HCU mouse model in certain embodiments disclosed herein.

FIG. 10 represents a bar graph illustrating level of homocysteine versus cysteine for treated (HO+glycine), (HO+glycine+betaine); and homocysteine (Hcy) versus cysteine (Cys) for treated (HO+serine), and treated (HO+serine+betaine) in certain embodiments disclosed herein.

FIGS. 13A-13C represent exemplary images of WT (FIG. 13A), Cbs null (−/−:BHMT mouse model knock out) (FIG. 13B) and HO (FIG. 13C) of liver samples obtained demonstrating level of tissue damage and demonstrating that treatment response observed herein was at least BHMT dependent.

FIG. 14 represents a bar graph of homocysteine levels (Hcy) of untreated and zinc treated HO mice and assessing level of homocysteine mouse model in certain embodiments disclosed herein.

FIG. 18A is a schematic diagram of the transsulfuration pathway and methionine-folate cycle pathways, FIG. 18B represents a bar graph of plasma levels of tHcy, methionine (Met), and total cysteine (Cys), serine (Ser), glycine (Gly), dimethylglycine (DMG), methylglycine (MG) in wild type mice and HO HCU mice, and FIG. 18C represents a bar graph of plasma SAM and SAH in wild type mice and HO HCU mice of certain embodiments disclosed herein.

FIGS. 21A-21C represent Western blotting analysis of hepatic BHMT, MTR and MTHFR expression levels in HO HCU mice with natural variance of Hcy (FIG. 21A), and MTHFR (FIG. 21B) and BHMT (FIG. 21C) protein levels in HO HCU mice with natural variance of tHcy of certain embodiments disclosed herein.

FIGS. 22A-22C represent Western blotting analysis of hepatic cytoplasmic SHMT1 (FIG. 22A) and hepatic mitochondrial SHMT2 (FIG. 22B) protein levels in HO HCU mice in the presence and absence of one week of betaine treatment; and an illustrative table of comparative metabolomic analysis of liver samples between WT and high HO HCU in the presence and absence of betaine treatment (FIG. 22C) of certain embodiments disclosed herein.

FIGS. 23A-23C represent Western blotting analysis and bar graphs of hepatic SAHH (FIG. 23A), MTHFR (FIG. 23B), and SHMT2 (FIG. 23C) protein levels in HO HCU mice in the presence and absence of one week of betaine treatment of WT and HO HCU mice of certain embodiments disclosed herein.

FIGS. 23D-23F represent Western blotting analysis and bar graphs of hepatic SAHH (FIG. 23D), MTHFR (FIG. 23E), and SHMT2 (FIG. 23F) protein levels in HO HCU mice in the presence and absence of one week of taurine treatment of WT and HO HCU mice of certain embodiments disclosed herein.

DEFINITIONS

Figure 1:
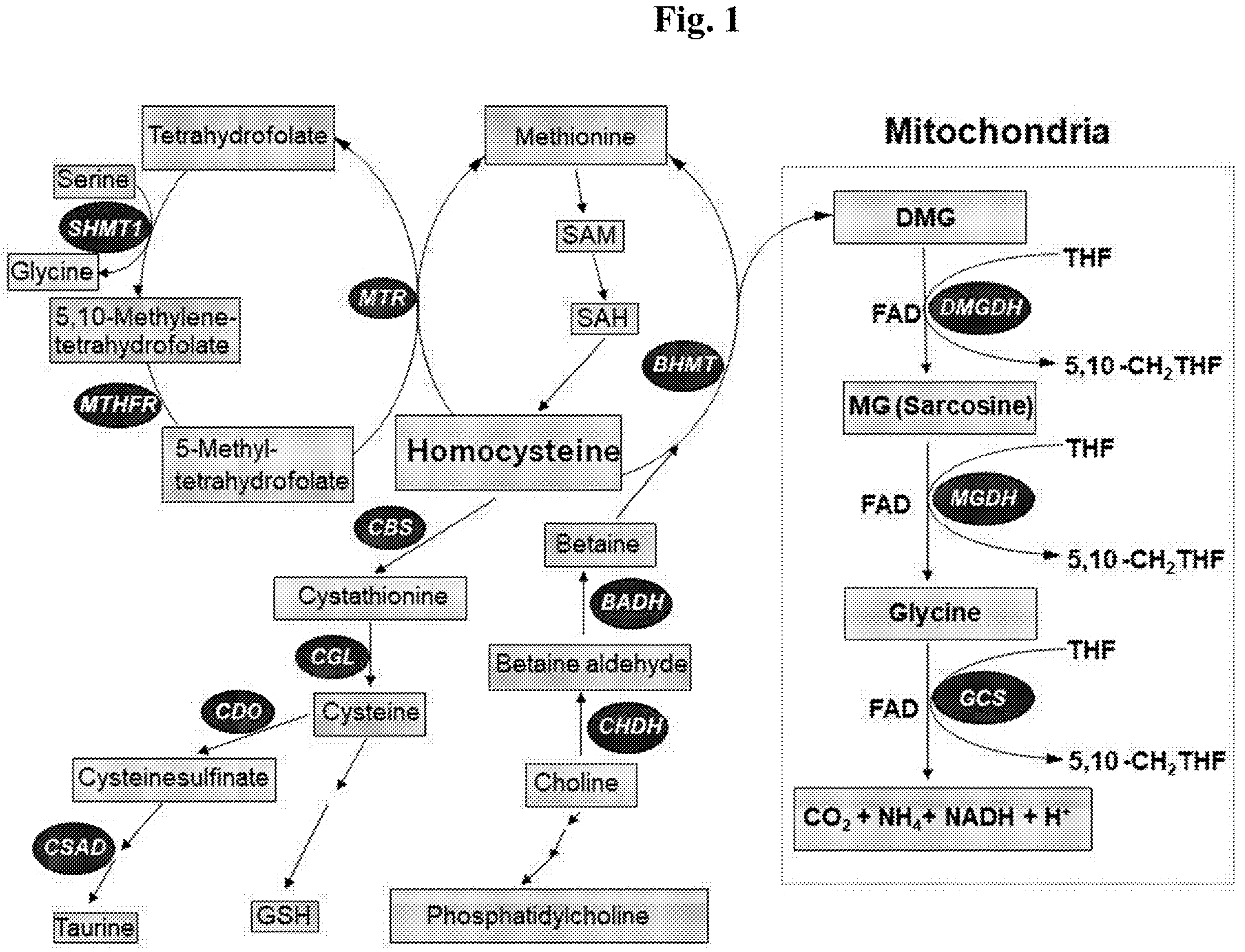
FIG. 1 is a schematic diagram representing methionine and cysteine and choline metabolism in mammals in certain embodiments disclosed herein.

Terms, unless specifically defined herein, have meanings as commonly understood by a person of ordinary skill in the art relevant to certain embodiments disclosed herein or as applicable.

Unless otherwise indicated, all numbers expressing quantities of agents and/or compounds, properties such as molecular weights, reaction conditions, and as disclosed herein are contemplated as being modified in all instances by the term "about." Accordingly, unless indicated to the contrary, the numerical parameters in the specification and claims are approximations that may vary by about 10 to about 15% plus and/or minus depending upon the desired properties sought as disclosed herein. Numerical values as represented herein inherently contain standard deviations that necessarily result from the errors found in the numerical value's testing measurements.

As used herein, "Homocysteine" or "Hcy" can refer to a sulfur-containing amino acid that is closely related to or a precursor of methionine and cysteine. There is no DNA-coding for Hcy, and it is not present in naturally occurring proteins. As used herein, "tHcy" can refer to total homocysteine.

As used herein, "One carbon metabolism" or "OCM" can refer to metabolism mediated by a folate cofactor that supports multiple physiological processes. These include biosynthesis (purines and thymidine), amino acid homeostasis (glycine, serine, and methionine), epigenetic maintenance, and redox defense. Reduced tetrahydrofolates (THFs) can serve as a family of enzyme cofactors that chemically activate and carry one carbon units on the N5 and/or the N10 of THF at the oxidation level of formate (e.g., 10-formylTHF), formaldehyde (e.g., 5,10-methyleneTHF), or methanol (e.g., 5-methylTHF). Folate derivatives also contain a covalently bound polyglutamate peptide of varying length. Serum folates contain a single glutamate residue, whereas intracellular folates contain a polyglutamate peptide usually consisting of five to eight glutamate residues that are polymerized through unusual γ-linked\ peptide bonds. OCM is compartmentalized within the cell with separate pools in the nucleus, cytoplasm and mitochondria as previously disclosed.

As used herein "polyamines" can refer to a family of molecules including putrescine, cadaverine, hypusine, spermine, and spermidine derived from ornithine or derivative or conjugate thereof. Polyamines play an important role in regulating cell growth and proliferation, the stabilization of negative charges of DNA, RNA transcription, protein synthesis, apoptosis, and the regulation of the immune response.

As used herein, "Formate" or "Formate prodrug" or "Formate precursor" or "Formate-like agent" can refer to formic acid or an agent capable of producing formic acid or format upon introduction to a subject as disclosed in certain embodiments disclosed herein. For example, a format derivative can include, but is not limited to, diformylglycerol, triformylglycerol (e.g. triformin) in an oil form, or other suitable form or combined with one or more excipients to improve bioavailability of formate or formate derivative. Alternatively, a formate derivative or prodrug contemplated herein can include a diformylglycerol-glucose conjugate or diformylglycerophosphocholine, diformylglycerophosphoethanolamine, or as a mixed glycerol ester, or other suitable form or combined with one or more excipients to improve bioavailability of formate or a formate derivative to a subject.

As used herein, "reduce," "inhibit." "diminish," "suppress," "decrease," "prevent" and grammatical equivalents (including "lower," "smaller," etc.) when in reference to expression of any symptom or level of any agent in an untreated subject having a condition relative to a treated subject having the same condition, can refer to quantity of an assessed agent and/or magnitude of a symptom or side-effect in the treated subject. In certain embodiments quantity of an assessed agent and/or magnitude of a symptom or side-effect in the treated subject is reduced or lowered when compared to the untreated subject by any amount that is recognized as clinically relevant by one of skill in the art or a health professional. In one embodiment, the quantity and/or magnitude of the agent and or symptom(s) in the treated subject is about 5%, or about 10%, or about 15%, or about 20%, or about 25%, or about 30%, or about 35%, or about 40%, or about 45% or about 50% lower or higher than the quantity and/or magnitude of the agent and or symptom(s) in the untreated subject.

As used herein, "individual", "subject", "host", and "patient" are used interchangeably herein and refer to any mammalian subject for whom diagnosis, treatment, or therapy is desired, particularly humans.

As used herein, "effective amount" as used herein, can refer to a particular amount of a pharmaceutical composition including a therapeutic agent that achieves a clinically beneficial result (e.g., for example, a reduction of symptoms or side effects of the condition).

DETAILED DESCRIPTION OF THE INVENTION

In the following sections, various exemplary compositions and methods are described in order to detail various embodiments of the invention. It will be obvious to one skilled in the art that practicing the various embodiments does not require the employment of all or even some of the specific details outlined herein, but rather that concentrations, times and other specific details may be modified through routine experimentation. In some cases, well known methods, or components have not been included in the description.

In certain embodiments, the instant disclosure relates, in part, to improved compositions for treating homocystinuria (e.g. HCU) in a subject. In some embodiments, improved compositions are contemplated to be used alone or combined with standard treatments to provide life-altering solutions to subjects having genetic homocystinurias. In some embodiments, compositions and/or formulations disclosed herein can reduce symptoms or signs of this Hcy aberrant condition. In other embodiments, compositions and/or formulations disclosed herein can improve lifestyle, reduce symptoms, and/or reduce morbidity in a subject having a Hcy aberrant condition contemplated herein.

Embodiments of the instant disclosure relate to novel compositions, methods and uses for treating a subject having genetic homocystinuria (e.g. HCU or other genetic form of aberrant Hcy levels) to improve clinical outcomes. In some embodiments, compositions and methods disclosed herein concern improving efficacy of existing treatments. In accordance with this embodiment, compositions disclosed herein can be combined with standard treatments of homocystinuria to improve outcomes. In certain embodiments disclosed herein, compositions can be used to treat aberrant homocysteine levels and reduce dietary compliance requirements for improved outcomes of the condition in the subject and improved lifestyle with reduced concerns. In some embodiments, compositions can include an effective amount of a polyamine or diamine thereof, a salt thereof, a polyamine or diamine derivative or polyamine or diamine precursor or prodrug agent, pectin or a recombinant bacteria capable of producing one or more polyamines or diamines of use as a single agent. In certain embodiments, the polyamine can include, putrescine, spermidine, spermine, a polyamine derivative (e.g. hypuscine) or a combination thereof. In other embodiments, a polyamine or diamine thereof, a salt thereof, a polyamine or diamine derivative or polyamine or diamine precursor or prodrug agent, pectin or a recombinant bacteria capable of producing one or more polyamines or diamines can be used to treat a subject in combination with other agents such as standard agents or other agents disclosed herein (e.g. betaine, formate or formate derivative, zinc, copper) to lower homocysteine (Hcy) levels in a subject having HCU, or other form of genetic homocystinuria, or similar condition over-producing homocysteine. In certain embodiments, a polyamine or diamine thereof, a salt thereof, a polyamine or diamine derivative or polyamine or diamine precursor or prodrug agent can be administered alone or in combination with trimethylglycine (e.g. betaine) to treat homocystinuria (HCU/RD or other forms of genetic homocystinuria).

In other embodiments, spermidine synthase and/or spermine synthase or other relevant enzyme can be induced in a subject to increase polyamine production in order to lower homocysteine (Hcy) levels in a subject having HCU, or other form of genetic homocystinuria, or similar condition over-producing homocysteine. In accordance with these embodiments, compositions to treat aberrant Hcy levels can include an effective amount of a polyamine such as spermine or spermidine or a diamine such as putrescine or cadavarine or hypusine or other polyamine or polyamine derivative, a salt thereof or polyamine precursor or prodrug agent to lower homocysteine (Hcy) levels in a subject. In certain embodiments, a polyamine derivative or other agent can include an analog. In some embodiments, other suitable form of polyamine or combination with polyamine can be provided to a subject to improve bioavailability of polyamines or polyamine derivatives.

In certain embodiments, the concentration of polyamines or diamines or derivatives thereof in a composition or as a supplement administered to a subject can be about 0.05 mg/kg to about 100.0 mg/kg; or about 0.05 mg/kg to about 80 mg/kg; or about 0.1 mg/kg to about 70 mg/kg: or 0.1 mg/kg to about 60 mg/kg; or 0.1 mg/kg to about 50 mg/kg; or about 0.1 mg/kg to about 40 mg·kg, at every meal, about 2-4 times per day, about 2-3 times per day, daily, every other day, weekly, or other suitable administration schedule. In certain embodiments, a subject can consume these supplements 1 time to about 3 times per day. It is contemplated that any treatment regimen can be used. In certain embodiments, polyamine or diamine or derivatives thereof can be given with food alone or in combination with other agents to treat HCU or other form of genetic homocystinuria in a subject.

In certain embodiments, one or more polyamine or polyamine-containing agent can be combined with standard HCU/RD or standard treatments for other forms of genetic homocystinuria or other agents to lower homocysteine (Hcy) levels in a subject. In some embodiments, a formate or formate derivative as indicated herein can be combined with or provided separately from, a polyamine (e.g. spermidine, spermine), diamine, or derivative thereof to the subject before, at the time of or after administering the polyamine, diamine, or derivative thereof to the subject. In other embodiments, zinc or zinc conjugate (and/or copper agent) as indicated herein can be combined with or provided separately from, a polyamine, diamine, or derivative thereof to the subject before, at the time of, with, or after, administering the polyamine, diamine, or derivative thereof to the subject. In some embodiments, a polyamine, a diamine, or derivative thereof as disclosed herein (e.g. at the same or different time) can be combined with any standard treatment; for example, trimethylglycine (e.g. betaine) where trimethylglycine can be administered to a subject at standard concentrations as noted above at the time of administering a polyamine or diamine or derivative thereof in a composition. In some embodiments, administration of any agent or combination of agents contemplated herein to treat HCU or other form of genetic homocystinuria or related condition can be during one or more meal.

In other embodiments, compositions contemplated herein can include a pharmaceutically acceptable formulation of one or more polyamines, diamines, polyamine derivative, or diamine derivative, a salt thereof (e.g. ammonium spermine, ammonium spermidine, spermidine trihydrochloride, spermine dihydrochloride, etc.), a polyamine or diamine derivative or polyamine or diamine precursor or prodrug agent for administration to a subject. In some embodiments, one or more polyamines of use herein can be produced by microorganisms or generated synthetically. In certain embodiments, compositions can include zinc or a zinc conjugate (and optionally a copper supplement) or other acceptable zinc delivery agent in combination with a polyamine, diamine, or polyamine or diamine prodrug disclosed herein. In yet other embodiments, compositions contemplated herein can include polyamines and/or zinc (and optionally, copper) and/or a standard treatment for HCU/RD or standard treatments for other forms of genetic homocystinuria such as trimethylglycine (e.g. betaine) or combinations thereof for optimal treatment. In certain embodiments, a polyamine- or diamine-containing compositions can be combined with a standard treatment for homocystinuria, (e.g. HCU) such as trimethylglycine (e.g. betaine, such as an anhydrous betaine, betaine hydrochloride). Modes of administration for these compositions can include any mode suitable for delivery of such agents such as oral administration (e.g. by tablet, liquid or hydratable powder, food supplement or additive or other delivery method), by inhalation, suppository or intra-rectally, intravenously, intra-rectally, or subcutaneously administered or other mode of administration.

In certain embodiments, polyamine or diamine combination regimens can include formate or formate derivative. Formate or formate derivative contemplated herein can be administered to a subject at about 0.5 mg/kg to about 100.0 mg/kg; or about 2.0 mg/kg to about 80 mg/kg; or about 3.0 mg/kg to about 70 mg/kg: or 4.0 mg/kg to about 60 mg/kg; or 5.0 mg/kg to about 50 mg/kg, 2-4 times per day, daily, every other day, weekly, or other suitable dosing regimen.

In some embodiments, a subject contemplated herein has homocystinuria (HCU) but not hyperhomocysteinemia. In some embodiments, a subject has genetic HCU or other genetic forms of homocystinuria such a RD or other genetic form of homocystinuria (for example, a subject having Hcy at a level of 70 μM or greater). In some embodiments, the subject has been taking betaine, and in some embodiments, the betaine treatments have become less effect or ineffective. In certain embodiments, a subject contemplated herein is not folate deficient, folate resistant or a subject having limited ability to absorb or metabolize folic acid (e.g. folate deficient-related condition). In other embodiments, the subject is a young child, adolescent or adult. In some embodiments, the subject is not a pregnant female and/or not a neonate. In other embodiments, a subject contemplated herein having HCU (e.g. genetic HCU) or other genetic form of homocystinuria has a blood homocysteine level of about 70 μM to about 450 μM, or about 100 μM to about 450 μM, or about 150 μM to about 450 μM, or about 200 μM to about 400 μM, or about 250 μM to about 400 μM which differs from a subject having hyperhomocysteinemia. A subject having hyperhomocysteinemia can differ from a subject having genetic HCU wherein a subject having hyperhomocysteinuria can have a level of blood homocysteine above 15 μM or blood homocysteine can differ by about 15 μM to 50 μM or less than 70 μM. One of skill in the art recognizes the difference between these conditions. It is recognized by one of skill in the art that Hyperhomocysteinemia is typically managed with vitamin B6, folic acid, and vitamin B12 supplementation which fails to treat HCU/RD or other form of genetic homocytinuria contemplate herein.

In some embodiments, compositions to treat homocystinuria can include an effective amount of one or more polyamine composition in combination with formate, a salt thereof (e.g. sodium formate), a formate derivative or formate precursor or prodrug agent to lower homocysteine (Hcy) levels in a subject. In certain embodiments, compositions disclosed herein can include administering pectin known to produce formate by intestinal fermentation in the microbiome; for example, administering at mealtime or in a gradual release form over several minutes, hours or more. In other embodiments, a subject can be treated with a microorganism (e.g. a probiotic bacteria or other organism capable of producing formate or formate derivative). In other embodiments, administration of one or more polyamine, diamine or derivative thereof as disclosed herein can be combined with at least one of taurine and n-acetylcysteine, or other equivalent in order to boost glutathione availability for formaldehyde detoxification for a more effective treatment with reduced side effects. In accordance with these embodiments, taurine concentration can be about 10 mg/kg to about 300 mgs/kg; or about 20 mg/kg to about 250 mgs/kg; or about 30 mg/kg to about 200 mgs/kg; or about 50 mg/kg to about 150 mgs/kg provided daily, two or more times per day, every other day or other appropriate dosing regimen separate from or in the same compositions as the other agents. In other embodiments, N-acetylcysteine concentration can be about 20 mg/kg to about 300 mgs/kg; or about 30 mg/kg to about 250 mgs/kg; or about 40 mg/kg to about 200 mgs/kg; or about 100 mg/kg to about 180 mgs/kg provided daily, two or more times per day, every other day or other appropriate dosing regimen separate from or in the same compositions as the other agents.

In certain embodiments, compositions disclosed herein can be administered to a subject having a genetic form of homocystinuria (e.g. HCU or other genetic forms of homocystinuria (e.g. RD)) can be treated with combinations of polyamines or diamines and zinc, mixed or administered separately. In some embodiments, zinc or a zinc conjugate or other acceptable zinc delivery agent can be administered to a subject can be about 1.0 mgs to about 150 mgs daily or every other day or other appropriate dosing regimen; or about 2.0 mgs to about 100 mgs daily or every other day; or about 3.0 mgs to about 80 mgs daily or every other day; or about 4.0 mgs to about 70 mgs daily or every other day; or about 5.0 mgs to about 60 mgs daily or every other day; or about 35 mg to 60 mgs per day for an adult or about 2 mgs to about 10 mgs for an infant or about 15 mgs to about 35 mgs for a child or adolescent.

In other embodiments, composition including polyamines or diamine or polyamine conjugate or derivative or precursor can be combined with standard treatments, for example administered before, after or at the time of administering (e.g. simultaneously) trimethylglycine (e.g. betaine) where trimethylglycine can be administered to a subject at standard concentrations. In accordance with these embodiments, trimethylglycine (e.g. betaine) can be administered or taken at about 10 mg/kg to about 200 mg/kg; or about 20 mg/kg to about 150 mg/kg; or 30 mg/kg to about 100 mg/kg; or 40 mg/kg to about 80 mg/kg; or about 50 mg/kg 2-4 times per day, daily, every other day, weekly, or other suitable administration schedule to the subject. In accordance with these embodiments, trimethylglycine can be administered in doses of about 20 mg/kg to about 200 mg/kg or about 50 mg/kg to about 150 mg/kg as a single administration or multiple administrations to a subject having homocystinuria (e.g. HCU or other genetic form of homocystinuria) or at mealtime where the dose is tailored to the number of times taken per day to about 1.0 gram to about a 40.0 gm total per subject daily. In certain compositions disclosed herein, an effective amount of trimethylglycine (e.g. betaine) in a composition separate from or in combination with polyamines or derivatives disclosed herein with about 1.0% to about 3% w/v or about 2% w/v concentration of trimethylglycine (e.g. betaine) in solution (e.g. water or other acceptable medium or excipient). In other embodiments, polyamines, diamines or conjugates or derivatives thereof can be combined with amino acid supplements or derivatives thereof such as glycine, serine, histidine or methylglycine or other suitable amino acid to reduce homocysteine levels and treat homocystinuria in the subject.

In some embodiments, compositions or formulations disclosed herein can be administered in powder form, tablet, by microparticle, in a slow or time-release microparticle in a solid or a liquid or other suitable format or other known time-delivery method. In certain embodiments, an effective amount of a composition or formulation can be administered for homocystinuria management (e.g., for a subject's lifetime).

In certain embodiments, one or more polyamine or polyamine-containing agent can be combined with standard HCU/RD or other treatments for genetic homocystinuria or other agents to lower homocysteine (Hcy) levels in a subject. In some embodiments, a formate or formate derivative as indicated herein can be combined with or provided separately from, a polyamine, diamine, or derivative thereof to the subject before, at the time of or after administering the polyamine, diamine, or derivative thereof to the subject. In certain embodiments, a formate derivative or other agent can include a formate prodrug esterified to glycerol, for example, diformylglycerol, triformylglycerol (e.g. triformin) in an oil form, or other suitable form or combined with one or more excipients to improve bioavailability of formate or formate derivative. Alternatively, a formate derivative or prodrug contemplated herein can include a diformylglycerol-glucose conjugate or diformylglycerophosphocholine, diformylglycerophosphoethanolamine, or as a mixed glycerol ester, or other suitable form or combined with one or more excipients to improve bioavailability. In certain embodiments, compositions disclosed herein can include administering pectin known to produce formate by intestinal fermentation in the microbiome, for example administering at mealtime or in a gradual release form over several minutes, hours or more. In other embodiments, a subject can be treated with a microorganism (e.g. a probiotic bacteria or other organism capable of producing formate or formate derivative). In certain embodiments, the concentration of formate or formate derivative contemplated herein can be administered to a subject at about 0.5 mg/kg to about 100.0 mg/kg; or about 2.0 mg/kg to about 80 mg/kg; or about 3.0 mg/kg to about 70 mg/kg: or 4.0 mg/kg to about 60 mg/kg; or 5.0 mg/kg to about 50 mg/kg, 2-4 times per day, daily, every other day, weekly, or other suitable dosing regimen.

Other embodiments disclosed herein contemplate treating a subject having HCU or other form of genetic homocystinuria or related condition can be treated with a regimen for a predetermined period of time and then changing or adjusting the treatment in order to avoid waning or lessening effects of the regimen. In accordance with these embodiments, a standard treatment such as trimethylglycine (e.g. betaine) in combination with polyamines and optionally, formate, and/or zinc (and/or copper) and/or polyamines/diamines to treat a subject. Then after a period of about a week, two weeks or more, a month, 2 months or more, 6 months or about a year, treatment regimens can be adjusted to use differing agents or combinations of agents disclosed herein in order to treat the subject and reduce dietary restraints and prolong treatment efficacy to avoid side effects of the HCU or other related genetic condition in a subject in need thereof.

Some embodiments disclosed herein concern kits that can include compositions disclosed herein for treating Hcy overproduction or modifying homocysteine production in a subject. In certain embodiments, kits can include capsules, microparticles, powders, liquid compositions, or tablet forms of the one or more compositions for ready administration or consumption by the subject for treating the disorder. In other embodiments, kits contemplated herein can include single agents, combinations of agents in a single formulation or separate agents. In yet other embodiments, agents of use to treat Hcy overproduction in a subject can include food additives for applying to a food or formulations to be added to a liquid to be consumed by a subject in need thereof.

HCU

Classical homocystinuria (HCU) is caused by deficiency of cystathionine (3-synthase (CBS). The CBS enzyme sits at the branch point between the methionine cycle and trans-sulfuration and catalyzes the condensation of serine and Hcy into cystathionine which is subsequently converted to cysteine by cystathionine γ-lyase (CGL), as illustrated in FIG. 1. HCU is characterized clinically by cognitive impairment with pronounced deficits in memory and learning, psychopathic behavior, seizures, connective tissue disturbances, and cardiovascular disease. Biochemically, HCU induces severe plasma/tissue elevations of Hcy, methionine, S-adenosylmethionine (SAM), S-adenosylhomocysteine (SAH), and abolition of cystathionine synthesis and decreased cysteine and glutathione levels. Cardiovascular complications are the major cause of morbidity in HCU and are also common to other genetic homocystinurias caused by impaired MTHFR or MTR function (e.g. homocysteine remethylation disorder forms of homocystinuria).

In some embodiments, MTR deficiency in a subject as disclosed herein can be inactivated through mutation of MTR or the enzyme that catalyzes the reduction of its cobalamin cofactor (methionine synthase reductase (MTRR)) or a range of genetic defects in cobalamin transport or metabolism that prevent the incorporation of this co-factor into MTR and thus prevent full MTR function. It is contemplated herein that these approaches to MTR deficiency can be combined with compositions, methods and treatment disclosed herein to treat HCU and other forms of genetic homocystinurias as determined by a health professional.

In some embodiments, a subject contemplated herein has homocystinuria (HCU) or other form of genetic homocystinuria but not hyperhomocysteinemia. In certain embodiments, a subject contemplated herein is not folate deficient, folate resistant or a subject having limited ability to absorb or metabolize folic acid (e.g. folate deficient-related condition). In other embodiments, the subject is a young child, adolescent or adult. In some embodiments, the subject is not a pregnant female and/or not a neonate. In other embodiments, a subject contemplated herein having HCU (e.g. genetic HCU) or other form of genetic homocystinuria has a blood homocysteine level of about 70 M to about 500 μM or more, or about 100 μM to about 450 μM, or about 150 μM to about 450 μM, or about 200 μM to about 400 μM, or about 250 μM to about 400 μM which differs from a subject having hyperhomocysteinemia. In yet other embodiments, compositions and combination compositions and regimens disclosed herein can be provided to a subject to treat HCU or other form of genetic homocystinuria in the subject. One of skill in the art recognizes the difference between these conditions. Hyperhomocysteinemia is typically managed with vitamin B6, folic acid, and vitamin B12 supplementation which fails to treat HCU in a subject.

One definition of hyperhomocysteinemia is that this condition as opposed to genetic HCU or other form of genetic homocystinuria is that hyperhomocysteinemia is characterized in relatively mild elevations in total plasma homocysteine. A typical concentration of homocysteine in normal humans is about 5 to about 13 μM. Elevations in plasma in the general population are typically very mild (reaching about 20 μM) and rarely as high as 50 μM. Plasma homocysteine in untreated HCU is typically about 70 μM to about 471 μM. In this latter condition, this significantly elevated level of homocysteine can be accompanied by severely elevated plasma methionine (normal reference range in humans is about 13 to 45 μM, HCU: elevated levels are frequently greater than 300 μM, such as 353-1891 μM), and/or S-adenosyl methionine (normal reference range in humans is 59 to 120 nM, HCU: elevated levels are frequently greater than 800 μM, such as 888-2030 nM), and/or S-adenosylhomocysteine (normal reference range in humans is about 9 to 21 nM, HCU: elevated levels are frequently greater than 100 nM, such as about 147-1700 nM). Often, in a subject having HCU, these elevated markers can be accompanied by a significant decrease in plasma cysteine concentrations (normal reference range in humans is 200 to 361 μM, HCU: reduced levels are frequently less than 200 μM, such as about 40-140 μM). Cystathionine can be completely absent in a subject having HCU compared to the about 50-342 nM that is typically observed in the normal human population.

In some embodiments, a subject to be treated by compositions and methods disclosed herein can have inherited homocysteine remethylation defects where homocystinuria can be due to one or more of methylenetetrahydrofolate deficiency (MTHFR); mutation in methionine synthase deficiency (MTR) or genetic defects in cobalamin B12 absorption, transport or metabolism including methionine synthase reductase, that can directly or indirectly impair methionine synthase function and lead to homocystinuria. In certain embodiments, side effects of genetic homocystinuria or other hypercoagulative conditions or related conditions thereof reduced or eliminated by treatments contemplated herein can include increasing clotting time or reducing hypercoagulation, a common side effect of these conditions. In other embodiments, side effects of genetic homocystinuria or other hypercoagulative conditions or related conditions thereof reduced or eliminated by treatments contemplated herein can include one or more conditions including, but not limited to, dislocation of the lenses in the eyes, nearsightedness, abnormal blood clots, osteoporosis, or weakening of the bones, learning disabilities, developmental problems, chest deformities, such as a protrusion or a caved-in appearance of the breastbone, long, spindly arms and legs, scoliosis or other side effect due to these conditions.

Other research using animal models has demonstrated that severely elevated homocysteine in a subject having HCU can lead to a decrease in hepatic taurine, glutathione, betaine and significantly altered phospholipid and lysophospholipid metabolism. In contrast to HCU, mild elevations of homocysteine in hyperhomocysteinemia do not affect any of the affected metabolites of subjects having HCU either in plasma or tissues. Therefore, hyperhomocysteinemia differs from genetic HCU or other form of genetic homocystinuria.

In contrast to mildly elevated homocysteine in hyperhomocysteinemia subjects, severe metabolic disturbances induced by inactivation of CBS are accompanied by multiple severe clinical features in genetic HCU or other form of genetic homocystinurias. In a previous study, it was observed that untreated pyridoxine non-responsive HCU patients had an average IQ of about 52, about an 82% chance of having a dislocated lens by the age of 10; about a 27% chance of experiencing clinically detected thromboembolic event; and about a 64% chance of radiologic detection of spinal osteoporosis by the age of 15. Methionine restriction to lower homocysteine initiated neonatally to a subject was able to completely prevent mental retardation and reduced the rate of lens dislocation. Subsequent studies demonstrated that when HCU patients are placed on homocysteine-lowering therapy (high doses of vitamin B6, vitamin B12, folic acid, and/or betaine, along with dietary methionine restriction) the risk of adverse vascular events and other pathogenic features were markedly reduced, demonstrating a very clear causative link between metabolic control and pathogenesis in this condition. This observation reinforces the point that there is no ambiguity about the causative relationship between the metabolic disturbances in genetic homocystinurias and clinical outcome. Later, it was demonstrated that treatment using a standard agent, betaine, in a mouse model of HCU significantly lowered plasma homocysteine below 100 μM and significantly ameliorated the hypercoagulative phenotype in these mice. Unfortunately, it was discovered that efficacy of betaine in lowering plasma total homocysteine in these HCU mice diminished significantly over a longer period of treatment with a return to total homocysteine levels greater than 100 μM accompanied by a return to the hypercoagulative phenotype further reinforcing the causative nature between metabolic control in HCU and pathogenesis. Therefore, the instantly claimed formulations and uses provide alternative and/or complementary treatments to betaine.

Given these differences in metabolic and clinical sequelae and respective response to homocysteine lowering treatments, mild hyperhomocysteinemia (Hcy from 15 μM 50 μM) referred to as hyperhomocysteinemia and genetic homocystinurias (HCU/RD or other forms of genetic homocystinuria) (Plasma total homocysteine >70) are different conditions. Further, the former being solely correlative and essentially benign, while the latter being serious and life-threatening diseases.

Standard Treatment of HCU

It is known in the art that treatment strategies for HCU and more specifically for pyridoxine non-responsive HCU by a health professional attempts to lower plasma and tissue levels of Hcy in an affected subject using a combination of restricting dietary intake of Hcy precursors such as methionine and further dietary supplementation with trimethylglycine, more commonly referred to as betaine. Betaine (N,N,N-trimethylglycine) is a zwitterionic quaternary ammonium compound that is also known as oxyneurin, glycine-betaine, or trimethylglycine. Trimethylglycine serves as a methyl donor in the remethylation of Hcy to methionine in a reaction occurring almost exclusively in the liver and catalyzed by betaine-homocysteine S-methyltransferase (BHMT). Early intervention with this treatment can prevent or ameliorate the clinical signs of HCU resulting in significantly improved survival and clinical outcome. However, compliance with a methionine-restricted diet is extremely difficult and often patients fail to adhere to such strict dietary constraints often with detrimental consequences. It is noted herein that standard HCU treatment using betaine lowers plasma and tissue levels of homocysteine in the treatment of genetic homocystinurias caused at least in part by impaired CBS, MTHFR or MTR (e.g. impairment of MTR can arise from either direct mutation of MTR, or the enzyme that catalyzes the reduction of its cobalamin cofactor (methionine synthase reductase (MTRR) (e.g. homocysteine remethylation disorder forms of homocystinuria)) or a range of genetic defects in cobalamin transport or metabolism that prevent the incorporation of this co-factor into MTR and thus prevent full MTR function). Betaine has no utility in lowering homocysteine in mild hyperhomocysteinemia cases as this condition is considered essentially benign and typically, an indirect consequence of other conditions or genetic polymorphisms and has been essentially eradicated by folic acid supplementation of flour and vitamins, for example.

It is known that the efficacy of betaine treatment in HCU diminishes significantly over time. If the efficacy of betaine treatment could be increased or this treatment replaced with a longer lasting treatment, it is conceivable that strict adherence to the methionine-restricted diet could be relaxed thus constituting a significant improvement in both outcome and quality of life for individuals with HCU. Improving understanding of metabolism in subject having genetic homocytinuria can lead to improving betaine treatment in all forms of homocystinuria with a view towards reducing dependence upon methionine-restriction and improving clinical outcome.

In certain embodiments, it was observed that there are significantly higher levels of BHMT protein in the long-term betaine treatment group where BHMT mediated remethylation of Hcy is diminished. By this observation, it raised the possibility that the BHMT protein is impaired in its function. Previous work demonstrated that purified BHMT requires a thiol-reducing agent for activity and that prolonged exposure of BHMT to buffers lacking reducing agents results in the slow irreversible loss of its catalytic zinc molecule and a corresponding loss of activity. In this context, further induction of BHMT expression observed in a long-term betaine treatment group could constitute a not entirely successful compensatory mechanism designed to mitigate the effects of diminished BHMT activity.

In other embodiments disclosed herein, it was observed that BHMT is unusual in that it constitutes approximately 2% of total protein in the liver. During long-term betaine treatment this concentration rises to up to four to five-fold (about 8-10%) of total hepatic protein which is an enormous amount of protein that would require zinc for its function. The increased requirement for zinc cannot be supplied because zinc cannot be stored in mammals and must be supplemented by diet or other source. Unfortunately, dietary sources of zinc are typically very high in protein and therefore precluded by the low methionine diet required of HCU patients. Therefore, long term betaine treatment in HCU could induce a significant zinc deficiency in a subject, impairing BHMT protein function and concomitantly reducing the betaine response.

It is contemplated herein that combination formulations of polyamines, and/or betaine and/or zinc and/or a copper supplement can be provided to a subject having aberrant levels of Hcy as a single composition or in one, two or three separate formulations and administered to a subject at the same time or consecutively. In certain embodiments, it is contemplated that these combination treatment regimens can be used alone or in combination with a formate or formate derivative and/or pectin to significantly reduce dietary compliance needs of a subject having aberrant Hcy levels while reducing symptoms of the condition, improving outcomes and survival.

In some embodiments, polyamines or a polyamine derivative can be administered at mealtime to the subject alone or in combination with standard treatments for lowering Hcy; and/or in combination with zinc or zinc-containing agent and/or betaine and/or formate. In certain aspects of the invention, compositions disclosed herein for treating a subject having aberrant levels of Hcy can reduce or eliminate the need for monitoring the diet of the subject depending on the subject being treated and level of Hcy in the subject or other factors. In certain aspects of the invention, polyamines, or a polyamine derivative alone or in a combination disclosed herein is capable of prolonging the effects of; or reducing the tolerance of standard Hcy management regimens (e.g. betaine administration). In other embodiments, compositions disclosed herein decrease plasma tHcy levels by at least 10%, at least 20%, at least 30%, at least 40%, at least 50%, at least 60%, or more, up to 100% or normalized to control levels using an effective amount of a composition including polyamines or a polyamine derivative.

In other embodiments, compositions disclosed herein decrease plasma tHcy levels by at least 30, by at least 40, by at least 50, by at least 60, by at least 70, by at least 80 or by at least 90% or more, up to 100% restored to normal levels (compared to an untreated subject having the condition) using an effective amount of a composition including polyamines or a polyamine derivative and a standard treatment. In certain embodiments, these treatment reduce or eliminate the need for dietary restraints.

In other embodiments, polyamines or a polyamine derivative can include providing to the subject, a composition (e.g. pharmaceutical composition) containing one or more polyamine or diamine, a salt thereof, a polyamine or diamine derivative or polyamine or diamine precursor or prodrug agent. In other embodiments, recombinant bacteria capable of producing one or more polyamines or diamines can be used to generate these agents as recombinants for use in methods disclosed herein. In certain embodiments, polyamines or diamines can be used single agents or in a combination with other agents such as standard agents or other agents disclosed herein (e.g. formate or formate derivative, zinc, copper) to lower homocysteine (Hcy) levels in a subject having HCU or other form of genetic homocystinuria or similar condition over-producing homocysteine. In other embodiments, spermidine and/or spermine compositions can be used to treat the subject. In accordance with these embodiments, compositions to treat aberrant Hcy levels can include an effective amount of spermine or spermidine or other polyamine or polyamine derivative, a salt thereof or polyamine precursor or prodrug agent to lower homocysteine (Hcy) levels in a subject. In certain embodiments, a polyamine derivative or other agent can include an analog. In some embodiments, other suitable forms of polyamines or combinations with polyamines can be provided to a subject to improve bioavailability of polyamines or polyamine derivatives. In some embodiments, other suitable form of polyamine or other agents in combination with polyamine can be provided to a subject to improve bioavailability of polyamines or polyamine derivatives. In some embodiments, the concentration of polyamines or diamines or derivatives thereof administered to a subject can be about 0.05 mg/kg to about 100.0 mg/kg; or about 0.05 mg/kg to about 80 mg/kg; or about 0.1 mg/kg to about 70 mg/kg: or 0.1 mg/kg to about 60 mg/kg; or 0.1 mg/kg to about 50 mg/kg; or about 0.1 mg/kg to about 40 mg·kg, about 2-4 times per day, about 2-3 times per day, daily, every other day, weekly, or other suitable administration schedule. In certain embodiments, a subject can consume these supplements 1 time to about 3 times per day. It is contemplated that any treatment regimen can be used. In certain embodiments, polyamine or diamine or derivatives thereof can be given with food alone or in combination with other agents to treat HCU or other form of genetic homocystinuria in a subject.

In certain embodiments, one or more polyamine or polyamine-containing agent can be combined with standard HCU, or other form of genetic homocystinuria or other agents used to lower homocysteine (Hcy) levels in a subject.

In some embodiments, a polyamine, a diamine, or derivative thereof as disclosed herein (e.g. at the same or different time) can be combined with any standard treatment; for example, trimethylglycine (e.g. betaine) where trimethylglycine can be administered to a subject at standard concentrations as noted above at the time of administering a polyamine or diamine or derivative thereof in a composition. In other embodiments, a formate or formate derivative as indicated herein can be combined with or provided separately from, one or more polyamine, diamine, or derivative thereof to the subject before, at the time of or after administering the polyamine, diamine, or derivative thereof to the subject. In other embodiments, zinc or zinc conjugate (and/or copper agent) as indicated herein can be combined with or provided separately from, a polyamine, diamine, or derivative thereof to the subject before, at the time of or after administering the polyamine, diamine, or derivative thereof to the subject. In some embodiments, a polyamine, a diamine, or derivative thereof as disclosed herein (e.g. at the same or different time) can be combined with any standard treatment; for example, trimethylglycine (e.g. betaine) where trimethylglycine can be administered to a subject at standard concentrations as noted above at the time of administering a polyamine or diamine or derivative thereof in a composition. In some embodiments, administration of any agent or combination of agents contemplated herein to treat HCU, or other form of genetic homocystinuria or related condition can be during one or more meal.

In other embodiments, compositions contemplated herein can include a pharmaceutically acceptable formulation of one or more polyamines, diamines, polyamine derivative, or diamine derivative, a salt thereof (e.g. ammonium spermine, ammonium spermidine, spermidine trihydrochloride, spermine dihydrochloride, etc.), a polyamine or diamine derivative or polyamine or diamine precursor or prodrug agent for administration to a subject. In some embodiments, one or more polyamines or one or more diamines of use herein can be produced by microorganisms or generated synthetically using recombinant or other appropriate technologies. In certain embodiments, compositions can include zinc or a zinc conjugate (and optionally a copper supplement) or other acceptable zinc delivery agent alone or in combination with a polyamine, diamine, or polyamine or diamine prodrug disclosed herein. In certain embodiments, a composition can include the polyamine precursor ornithine. In yet other embodiments, compositions contemplated herein can include polyamines and/or zinc (and optionally, copper) and/or a standard treatment for HCU such as trimethylglycine (e.g. betaine) or combinations thereof for optimal treatment. In certain embodiments, a polyamine- or diamine-containing compositions can be combined with a standard treatment for homocystinuria, (e.g. HCU) such as trimethylglycine (e.g. betaine, such as an anhydrous betaine, betaine hydrochloride). Modes of administration for these compositions can include any mode suitable for delivery of such agents, for example, oral administration (e.g. by tablet, liquid or hydratable powder or supplement), intravenously, intra-rectally, by dissolvable intra-buccal administration (e.g. under the tongue dissolving form or absorption through the cheek by adherence to the cheek) or subcutaneously administered or other mode of administration. In some embodiments, polyamine- or diamine-containing compositions can be provided as a food additive or given before, during or after meal consumption.

In some embodiments, polyamine- or diamine-containing compositions can be part of a slow or timed-release tablet or microparticle (e.g. in a capsule or for dispersing or sprinkling on food or into a liquid etc.). In certain embodiments, the polyamine can be spermidine, spermine or a combination thereof. Other agents such as standard treatments used to treat HCU, or other form of genetic homocystinuria or related conditions can also be administered at the same time, sequentially or alternating with treatment of polyamine- or diamine-containing compositions.

Other embodiments disclosed herein contemplate treating a subject having HCU, or other form of genetic homocystinuria, or related condition with a regimen disclosed herein for a predetermined period of time and then changing or adjusting the treatment in order to avoid waning, and/or tolerance to the treatment or lessening effectiveness of the regimen. In accordance with these embodiments, a standard treatment such as trimethylglycine (e.g. betaine) alone or in combination with polyamines and at least one of formate, and/or zinc (and/or copper) can be used to treat a subject and then after a period of about a week, two weeks or more, a month, 2 months or more, 6 months or about a year, treatment regimens can be adjusted to use differing agents or combinations of agents disclosed herein in order to treat the subject, reduce dietary restraints and/or prolong treatment efficacy in a subject in need thereof. In certain embodiments, a subject can assess Hcy levels on a multi-daily, daily, every other day, a couple of times per week, weekly, every other week or other regimen in order to assess efficacy of a given treatment in order to adjust the treatment or change the treatment for improved control of Hcy levels in the subject.

In some embodiments, treatment regimens disclosed herein can be used to reduce side effects due to over production of homocysteine such as side effects in the liver and kidneys. In certain embodiments, treatment regimens disclosed herein can be used to reduce and/or stabilize adverse conditions in the kidneys such as hepatic levels of N-acetylmethionine, N-formylmethionine, methionine sulfoxide, 5-methylcysteine, N-acetyl taurine, taurocyamine and N-acetylserine or other enzyme or by-product of over-production or lack of control of homocysteine metabolism in a subject contemplated herein. It has been observed that standard treatments such as trimethylglycine (e.g. betaine) alone fail to adequately control certain side effects in subjects having HCU, or other form of genetic homocystinuria and in fact, these standard treatments if continued without other interventions can lead to tolerance and/or reduced effects in a subject experiencing such a treatment. In certain embodiments, compositions disclosed herein can be used to supplement, replace or be used as an alternative treatment for HCU by, for example, controlling, reducing or modifying levels of N-acetylmethionine, N-formylmethionine, methionine sulfoxide, 5-methylcysteine, N-acetyl taurine, taurocyamine and/or N-acetylserine or other agent or enzyme(s) or by-product of over-production or lack of control of homocysteine metabolism in a subject. In accordance with these embodiments, compositions disclosed herein can be used to supplement, replace or be used as an alternative treatment for controlling, reducing or modifying levels of N-acetylmethionine, N-formylmethionine, methionine sulfoxide, 5-methylcysteine, N-acetyl taurine, taurocyamine and/or N-acetylserine or other agent or enzyme(s) or by-product of over-production or lack of control of homocysteine metabolism in the kidneys of a subject in need thereof. In other embodiments, compositions disclosed herein can be used to supplement, replace or be used as an alternative treatment for controlling, reducing or modifying levels of MTA in the liver of a subject having HCU or other form of genetic homocystinuria, or related condition. In accordance with these embodiments, composition containing agents such as polyamines, diamines, formate, zinc or other agents disclosed herein or derivatives thereof or salts thereof, can be used alone or in combination with standard treatments to regulate MTA and/or reduce MTA accumulation in the liver of a subject.

Some embodiments disclosed herein concern kits that can include compositions disclosed herein for treating Hcy overproduction in a subject. In certain embodiments, kits can include capsules, microparticles, powders, slow-release formulations, liquid compositions or supplements, or tablet forms of the one or more compositions for ready administration or consumption by the subject for treating the disorder (e.g. HCU). In other embodiments, kits contemplated herein can include combinations of agents in a single formulation or separate agents. In yet other embodiments, agents of use to treat Hcy overproduction in a subject can include food additives for applying to a food to be consumed by a subject in need thereof and/or liquid formulations or the like.

Pharmaceutical Compositions

Pharmaceutically acceptable salts as contemplated herein are known in the art and can be prepared using standard methods. See, for example, Remington's Pharmaceutical Sciences, 20th ed., Lippincott Williams & Wilkins, Baltimore, Md., 2000, p. 704; and "Handbook of Pharmaceutical Salts: Properties, Selection, and Use," P. Heinrich Stahl and Camille G, Wermuth, Eds., Wiley-VCH, Weinheim, 2002. Pharmaceutically acceptable salt can include alkali metal salts, including sodium or potassium salts; alkaline earth metal salts, e.g., calcium or magnesium salts; and salts formed with suitable organic ligands, e.g., quaternary ammonium salts. Examples of suitable formate salts include calcium formate, sodium formate, ammonium formate, potassium formate, magnesium formate, and combinations thereof.

It is contemplated herein that bacteria or other microorganism capable of producing formate are known in the art. Any microorganism such as bacteria capable of producing formate or a formate derivative and modified for administration to a subject are contemplated for use to treat a subject having homocystinuria or with other agents disclosed herein.

Exemplary methods of administering a composition and/or formulation disclosed herein can include: oral administration, for example, drenches (aqueous or non-aqueous solutions or suspensions), tablets, dissolving buccal patch, e.g., those targeted for buccal, sublingual, and systemic absorption, boluses, powders, granules, pastes for application to the tongue; parenteral administration, for example, by subcutaneous, intra-rectal, intramuscular, intravenous or epidural injection as, for example, a sterile solution or suspension, or sustained-release formulation; and topical administration, for example, as a cream, patch, ointment, or a controlled-release patch or spray applied to the skin. Any other known methods for administering compositions and/or formulations disclosed herein are considered plausible given the types of compositions and/or formulations.

In some embodiments, effective amount of an agent (e.g. polyamine) can refer to a particular amount of a pharmaceutical composition including a therapeutic agent that achieves a clinically beneficial result (e.g., for example, a reduction of symptoms or side effects of the condition). Toxicity and therapeutic efficacy of such compositions can be determined by one of skill in the art by, for example, determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred Data obtained from these studies can be used in formulating a range of dosage for a particular subject having or suspected of developing the condition. Dosage of such compounds can be a range of circulating concentrations that includes the $ED_{50}$ with little or no toxicity. Dosage can vary within this range depending upon the dosage form employed, sensitivity of the subject, age of the subject and other standard parameters tested, and the route and frequency of administration.

It is contemplated that regimens used to treat homocystinuria as disclosed in some embodiments of the present invention can be checked for efficacy. In accordance with these embodiments, treatment regimens can be modified by a health professional to achieve desired outcomes as needed. In certain embodiments, levels of homocystinuria are measured before and after treatment or periodically in a subject having homocystinuria to assess efficacy and regimens are adjusted as necessary.

Kits

In some embodiments, composition disclosed herein can be present in one or more containers or vials, e.g., single use or multi-use containers or vials. In other embodiments, multi-use vials can include a rubber diaphragm suitable for retrieving multiple doses of the agent or a container for storing tablets or caplets or other orally administered agent. In other embodiments, compositions and formulations disclosed herein can be stored for administration to a subject in a bag for intravenous delivery. In certain embodiments, the composition can be diluted in a suitable diluent or mixed with other agents for distributing on food of for administration as a tablet or other form to a subject. In some embodiments, compositions or formulations disclosed herein can be delivered to a subject in a buccal patch for rapid delivery or other delivery method such as a slow-release microparticle disclosed herein. In other embodiments, compositions and formulations disclosed herein can be stored as part of a kit for treating homocystinuria or other condition having aberrant Hcy production and can include at least one delivery device.

In some embodiments, the kit or composition can include a single-dose or multiple doses such as a week or month's supply of any composition or multiple compositions disclosed herein. In other embodiments, compositions disclosed herein can be part of a liquid formulation or readily available for adding to a liquid consumable such as water, a dietary supplement or other liquid form. In some embodiments, compositions disclosed herein can include a preservative. In other embodiments, a delivery device can include a syringe or intravenous delivery. In other embodiments, a syringe can be used to or is adapted for use to deliver the composition.

In certain embodiments, the subject is a mammal (e.g. horse, dog, cat, cow, pig, sheep, goat, rabbit). In other embodiments, the subject is a human. In yet other embodiments, the subject is a baby, a toddler, a young child, a child or adolescent or teenager. In other embodiments, the subject is an adult of 18 years or older.

EXAMPLES

The following examples are included to illustrate various embodiments. It should be appreciated by those of skill in the art that the techniques disclosed in the examples which follow represent techniques discovered to function well in the practice of the claimed methods, compositions, and apparatus. However, those of skill in the art should, in light of the present disclosure, appreciate that changes may be made in some embodiments which are disclosed and still obtain a like or similar result without departing from the spirit and scope of the invention.

Example 1

In one exemplary method, as illustrated in FIG. 1, pathways of production and control of aberrant homocysteine (Hcy) are studied. FIG. 1 is an exemplary schematic diagram of methionine, cysteine and choline metabolism in mammals related to embodiments disclosed herein. Referring to FIG. 1, the transsulfuration pathway, methionine-folate cycles and the choline-betaine pathways are illustrated. Betaine-aldehyde dehydrogenase (BHDH) Betaine-homocysteine S-methyltransferase (BHMT), choline dehydrogenase (CHDH) cystathionine β-synthase (CBS), cystathionine γ-lyase (CGL), cysteinesulfinate decarboxylase (CASD) cysteine dioxygenase (CDO), dimethylglycine dehydrogenase DMGDH), glycine N-methyltransferase (GNMT), glycine cleavage system (GCS), methionine adenosyl transferase (MAT1A), methionine synthase (MTR), methylenetetrahydrofolate reductase (MTHFR), methylglycine dehydrogenase (MGDH), S-adenosyl homocysteine hydrolase (SAHH) are identified in the figure for ease of reference.

As illustrated in FIG. 1, one major regulatory point in the Hcy-betaine pathway response occurs after betaine is converted to dimethylglycine (DMG) during remethylation of Hcy where DMG can serve as an allosteric inhibitor of BHMT and further BHMT activity requires its removal via dimethylglycine dehydrogenase (DMGDH) followed by MG (sarcosine) production to glycine production via dehydrogenase (MGDH) and subsequent degradation of glycine by the glycine cleavage system.

As observed in this schematic diagram, these three later steps have a need for the folate compound tetrahydrofolate (THF) as a co-factor. Methionine synthase (MTR) deficiency can create a "methyl-folate trap" due at least in part to the generation of 5-methyl-THF (5-Me-THF) which is irreversible. Interruption of this MTR pathway to convert Hcy to methionine and or THF prevents conversion of Hcy to THF resulting in adverse accumulation of 5-Me-THF and significant depletion of THF. Therefore, as disclosed herein, one aspect of embodiments of the instant invention is directed to improving betaine performance and it is understood that reduced betaine efficacy can be due at least in part to depleted THF levels. Exemplary compositions and methods disclosed herein are directed to improving betaine efficacy and directed to improving THF levels in a subject having overproduction of Hcy.

Homocystinuria induces multiple interruptions in hepatic one-carbon metabolism (OCM) with the potential to impair betaine treatment by limiting THF supply. Further, aberrant Hcy levels in a HCU mouse model was observed to induce hepatic 5-Me-THF accumulation and repress dihydrofolate reductase, ALDH111, GART and AMT and GLDC—all of these repressions have the potential to limit THF supply and thus impair the betaine response.

The HO Transgenic Mouse Model of HCU

In another exemplary method, an acceptable mouse mode of HCU was used to study various effects of exemplary compositions disclosed herein on aberrant Hcy levels. To date, the majority of research on HCU had been performed using a CBS knockout mouse model. These Cbs (−/−) animals experienced pronounced liver injury and typically die within 2-3 weeks of birth. It has been demonstrated that betaine treatment improved survival of Cbs (−/−) mice and restored fertility to female Cbs (−/−) mice, but without significantly lowering Hcy. Surviving Cbs (−/−) mice failed to show any alteration in coagulation parameters compared to wild-type controls and exhibited severe liver injury, steatosis, and fibrosis that were not significantly improved by betaine treatment. The failure of betaine treatment to lower Hcy in Cbs null mice was most likely due to the influence of severe liver injury upon hepatic BHMT expression. The fact that betaine treatment significantly improved survival in Cbs null mice without significantly lowering tHcy indicated that this compound may exert significant protective effects in HCU independent of its role as a substrate for BHMT.

To date, the only animal model of HCU that had been demonstrated to accurately recapitulate the biochemical response to betaine that was typically observed in human subjects with HCU, was a transgenic model in which the mouse Cbs gene was inactivated and that exhibited very low-level expression of the human CBS gene under the control of the human CBS promoter. This mouse model which is designated "human only" (HO), exhibited severe elevations in both plasma and tissue levels of Hcy, methionine, AdoMet, and AdoHcy and a concomitant decrease in plasma and hepatic levels of cysteine.

In addition, betaine treatment of the HO model demonstrated an increase in plasma methionine, DMG, MG, and cysteine respectively ($P<0.0001$ for all four metabolites). Lowering plasma tHcy by betaine treatment also resulted in a 40% decrease in plasma AdoMet ($P=0.0039$) and a fivefold decrease in AdoHcy levels ($P<0.0001$). These data indicated that the HO mouse recapitulates the biochemical response of human subjects with HCU to betaine treatment. This mouse model constituted a suitable model for investigating ways to optimize the therapeutic effects of treatments for HCU in a human subject.

The HO mouse model of HCU exhibited constitutive expression of multiple pro-inflammatory cytokines and a hypercoagulative phenotype both of which respond to short-term standard (e.g. betaine) treatment. Investigation of the effects of long-term betaine treatment in the absence of methionine-restriction in HO HCU mice revealed that the ability of betaine treatment to lower homocysteine diminished significantly over time. Plasma metabolite analysis indicated that this effect was due at least in part, to reduced betaine-homocysteine S-methyltransferase (BHMT) mediated remethylation of homocysteine. An observed increase in plasma homocysteine during prolonged betaine treatment was accompanied by a significant increase in the plasma levels of TNF-α and IL-1β and reversion to a hypercoagulative phenotype. Despite this decrease in the ability to respond to betaine, significantly higher levels of BHMT protein was observed during long-term betaine treatment indicating that the specific activity of this enzyme had decreased.

Exemplary experiments using the HO mouse model and various Hcy lowering treatments are disclosed herein for studying HCU. In certain exemplary methods, formate treatment alone or combined with betaine may dramatically improve clinical outcome in HCU. These treatments may be able to remove the need for a methionine restricted diet in a subject having HCU. It was observed that aberrant levels of Hcy can induce significant dysregulation of OCM and that formate or a formate derivative is capable of exerting its therapeutic effects by serving as a THF donor compound and thus can lead to remethylation of Hcy.

In the following exemplary experiments, it was observed that betaine supplementation was limited as observed in a mouse model of MTR deficient homocystinuria. As noted in FIG. 1, homocystinuria can occur due to defects in the Hcy remethylation enzymes MTR or MTHFR. It was observed that supplementation of betaine in certain experiments with a mouse model of MTR deficient homocystinuria lead to reduction of tHcy of approximately 25% having little effect on the condition. This modest decrease in betaine mediated treatment of MTR deficient homocystinuria has also been observed in human patients with this form of homocystinuria.

Figures 2, 3:
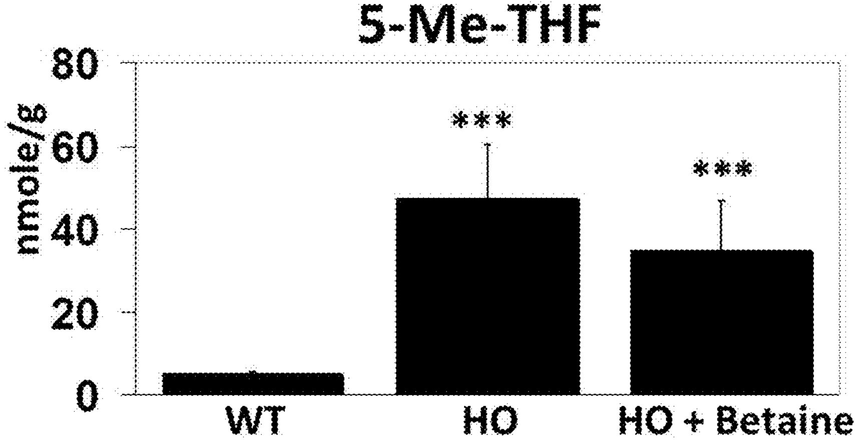
FIG. 2 represents an exemplary comparison of the effects of trimethylglycine (e.g. betaine) compared to controls of the levels of hepatic 5-methyl-THF in a HCU mouse model (e.g. HO, human only, mice) for wild type (WT), treated (HO+betaine) and untreated mice (HO) in certain embodiments disclosed herein.
FIG. 3 illustrates an exemplary supply chain of THF through the enzyme dihydrofolate reductase (DHFR) where DHFR reduces dihydrofolate to THF using NADPH as an electron donor in certain embodiments disclosed herein.

As illustrated in one example, see FIG. 2, HCU (HO) induced a significant accumulation of hepatic 5-methyl-THF which by sequestering one carbon units had the potential to decrease the available pool of THF available to the betaine pathway for lowering Hcy. FIG. 2 illustrates an example of hepatic metabolomic analysis of HO and WT controls compared to an HO mouse treated with betaine. Comparative hepatic metabolomic analysis of HO mice and WT controls illustrated about a 10-fold accumulation in the MTHFR product 5-MeTHF. Betaine treatment alone reduced 5-MeTHF by about 15-25%. Data illustrated in FIG. 2 was derived from the livers of 8 (4 male, 4 female) individual HO or WT or HO Betaine mice per group. Betaine was given at 2% w/v in drinking water given ad libitum. P<0.0001 vs WT.

Example 2

In another exemplary method, as illustrated in FIG. 3, an exemplary supply chain of THF occurred through the enzyme dihydrofolate reductase (DHFR) where DHFR reduces dihydrofolate to THF using NADPH as an electron donor in certain embodiments disclosed herein. As indicated above, induction of this pathway can serve to supplement THF in a subject having HCU. Hepatic DHFR expression was strongly repressed in HCU in a manner likely to diminish THF availability for the betaine pathway.

In other exemplary experiments, levels of DHFR were assessed using the HO mouse model in untreated and betaine treated mice. As illustrated in an exemplary Western blot, level of DHFR compared to a control enzyme, GAPDH were observed for various conditions, wild type (WT) without a condition and treated (HO+betaine) compared to untreated mice (HO) using the HCU mouse model (FIG. 4A). In addition, level of intensity of DHFR for wild type (WT), treated (HO+betaine) and untreated mice (HO) using the HCU mouse model was examined (FIG. 4B). It was noted that the level of DHFR in betaine treated mice was not restored to control levels and only about a 5-10% improvement was observed (FIG. 4B). (See FIGS. 4A-4B). As noted herein, Western blotting analysis of hepatic DHFR protein levels in WT and HO HCU mice. N=9 per group. These data are representative of three independent experiments.

Example 3

In another exemplary method, as illustrated in FIG. 5, a schematic is presented of a relevant pathway to embodiments disclosed herein where 10-formyltetrahydrofolate dehydrogenase ALDH1l1 catalyzes conversion of 10-formyltetrahydrofolate, NADP, and water to tetrahydrofolate (THF), NADPH, and carbon dioxide to generate 5, 10 MethylTHF and methionine and other agents.

Figure 6A:
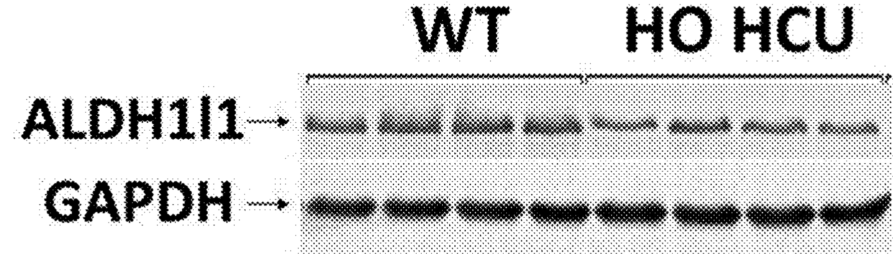
FIGS. 6A-6B represent a Western blot comparing the level of ALDH1l1 and GAPDH (control) for wild type (WT) and untreated (HO HCU) mice (HO) using the HCU mouse model (FIG. 6A); and further illustrating in a bar graph (FIG. 6B), level of intensity of ALDH1l1 for wild type (WT) and untreated (HO HCU) of the HCU mouse model in certain embodiments disclosed herein.
Figure 6B:
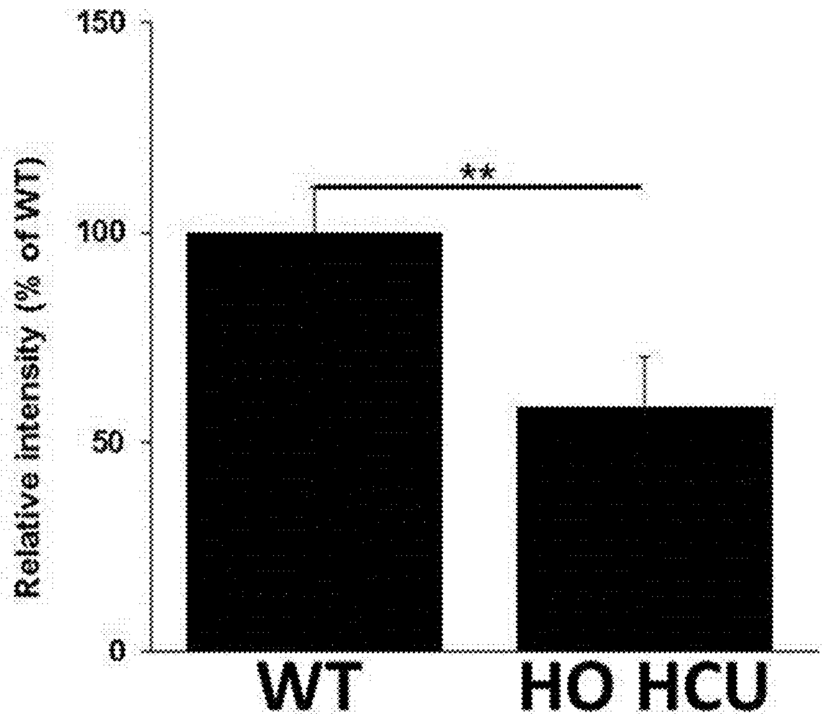

In another exemplary method, levels of the catalyst enzyme ALDH1l1 were measured in WT and experimental HO mice having aberrant Hcy levels. As illustrated in FIGS. 6A-6B, a Western blot image represents the level of ALDH1l1 and GAPDH (control) for wild type (WT) and untreated (HO HCU) mice (HO) using the HCU mouse model (FIG. 6A); and further illustrating in a histogram plot (FIG. 6B), level of intensity of ALDH1l1 for wild type (WT) and untreated (HO HCU) of the HCU mouse model. As observed herein the level of ALDH1l1 in the HCU mouse model was significantly reduced by about 50% or more. Western blot analysis of hepatic ALDH1l1 protein levels in WT and HO HCU mice had an N=9 per group. FIGS. 6A-6B is representative of three independent experiments.

Example 4

Figure 7:
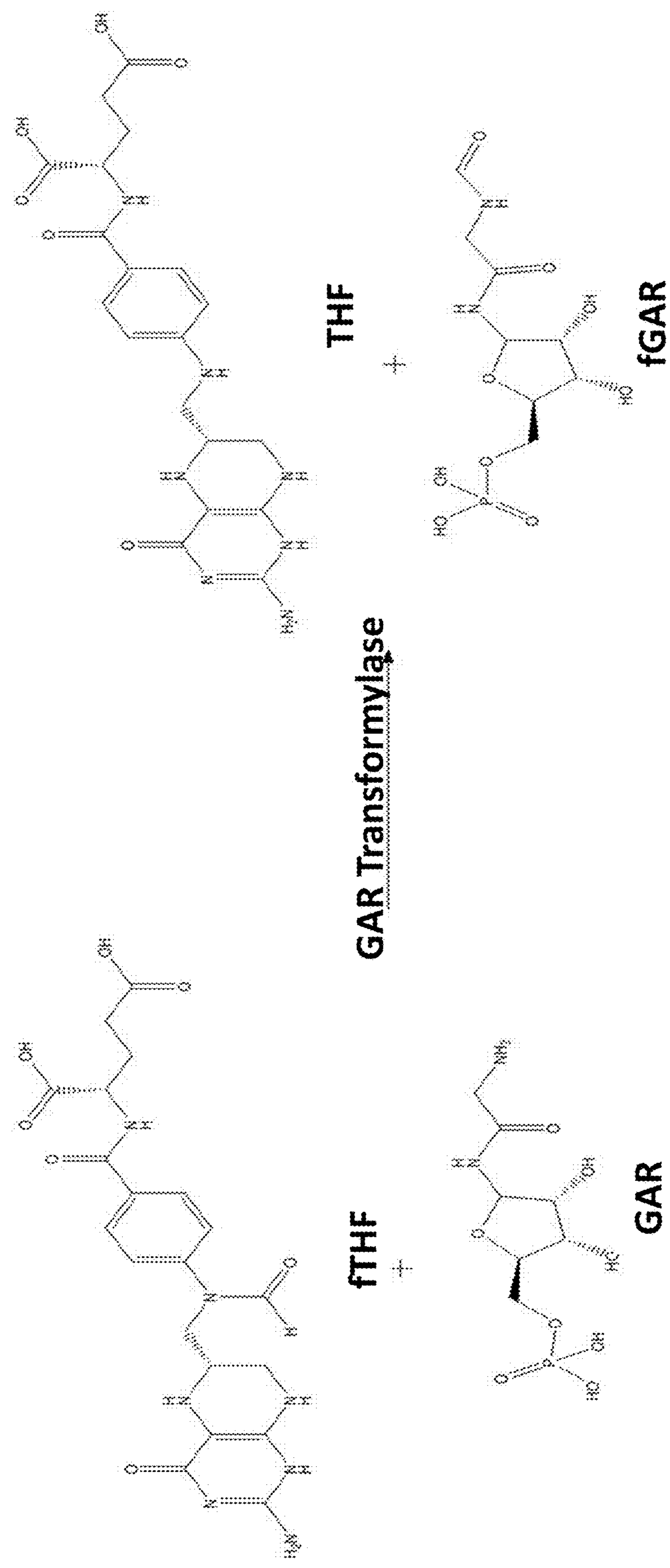
FIG. 7 is a schematic of a pathway where GART (also referenced as AIRS; GARS; PAIS; PGFT; PRGS; GARTF) is represented. GART is a trifunctional polypeptide having all three of phosphoribosylglycinamide formyltransferase, phosphoribosylglycinamide synthetase, phosphoribosylaminoimidazole synthetase activities which lead to de novo purine biosynthesis. Phosphoribosylglycinamide formyltransferase of GART is capable of generating THF from 10-formylTHF during de novo purine synthetic pathway in certain embodiments disclosed herein.

In another exemplary method, FIG. 7 is a schematic of a pathway where GART (also referenced as AIRS; GARS; PAIS; PGFT; PRGS; GARTF) is represented. GART is a trifunctional polypeptide having all three of phosphoribosylglycinamide formyltransferase, phosphoribosylglycinamide synthetase, phosphoribosylaminoimidazole synthetase activities which lead to de novo purine biosynthesis. Phosphoribosylglycinamide formyltransferase of GART was capable of generating THF from 10=formylTHF during de novo purine synthetic pathway in certain embodiments disclosed herein. In some exemplary experiments, GART levels were measured in WT and experimental HO mice having aberrant Hcy levels.

Example 5

Figure 8:
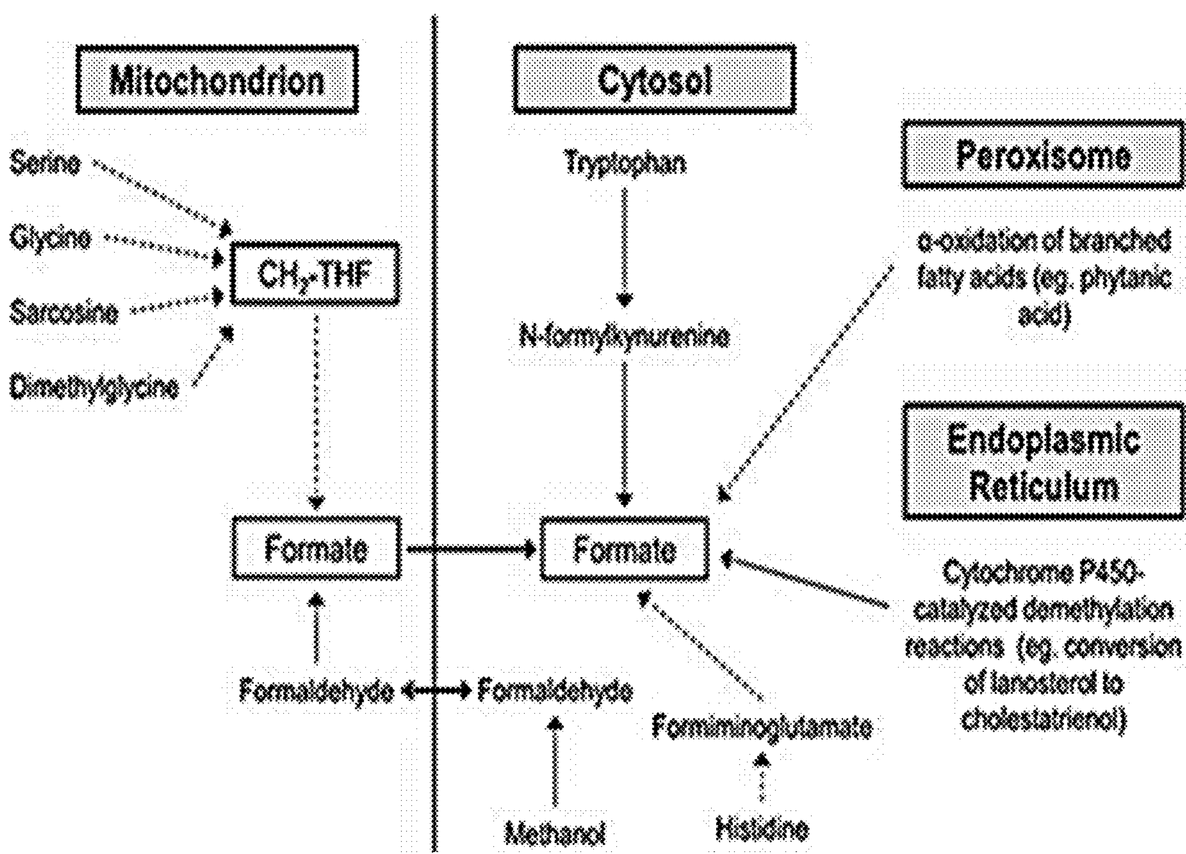
FIG. 8 is a schematic diagram of formate synthesis where multiple amino acids can serve as formate donors of certain embodiments disclosed herein.

FIG. 8 represents importance of formate in multiple pathways and is a schematic diagram of formate synthesis where multiple amino acids can serve as formate donors of certain embodiments disclosed herein.

In other exemplary methods, experiments were performed using the HO mouse model and administering various amino acids or amino acid derivatives to the mice and observing Hcy levels in the mice based on these treatments. It was observed that treatment with high level glycine (FIG. 9A) or serine (FIG. 9B) in drinking water significantly lowered plasma Hcy and increased plasma cysteine levels in HO mice in the presence of a normal methionine diet. As illustrated in FIGS. 9A and 9B, a histogram plot of level of homocysteine (Hcy) versus cysteine (Cys) for wild type (WT), untreated (HO) and treated (HO+glycine) (FIG. 9A); and FIG. 9B represents a histogram plot of the level of homocysteine (Hey) versus cysteine (Cys) for wild type (WT), untreated (HO) and treated (HO+serine) (B) of the HCU mouse model.

It is noted that WT mice (n=6) include untreated controls. HO HCU mice (N=8, 4 of each sex in each group) were either untreated or treated with about 3.0% (w/v) glycine w/v or about 3.0% (w/v) serine given in drinking water supplied ad libitum for one week. Plasma samples were taken and Hcy and cysteine levels were determined. *** denotes a P value <0.0001. Similar levels of Hcy reduction were observed with about 3.0% sarcosine (methylglycine) or about 3.0% (w/v) histidine. Therefore, these amino acid supplements can be used alone or in combination with other disclosed agents in order to treat aberrant Hcy levels in a subject such as a subject having HCU.

Surprisingly, when either of these treatments was combined with betaine treatment, no further reduction in plasma tHcy levels was observed (alternate treatment regimens are contemplated herein). Collectively, these points indicate a critical role for OCM in regulating tHcy levels in HCU.

Example 6

In other exemplary methods, combinations of exemplary amino acids (e.g. glycine and serine) in combination with standard betaine treatment was examined for further lowering of Hcy using the HO mouse model representative of a human having HCU.

In accordance with these methods, HO HCU mice (N=8, 4 of each sex in each group) were treated with either about 3.0% glycine w/v or about 3.0% w/v serine given in drinking water supplied ad libitum for one week in the presence and absence of about 3.0% w/v betaine. Plasma samples were taken from the mice at various times and Hcy levels were determined. It was observed that in the presence of the amino acids, further lowering of Hcy due to betaine was reduced and/or completely prevented. It is noted that this observation for glycine and serine in combination with betaine was also observed with certain other amino acids, histidine, sarcosine/methylglycine and tryptophan treatment.

As illustrated in FIG. 10, a histogram plot was generated to represent levels of homocysteine (Hcy) versus cysteine (Cys) levels for treated (HO+glycine), treated (HO+glycine+betaine); and homocysteine (Hcy) versus cysteine (Cys) for treated (HO+serine), treated (HO+serine+betaine) in certain embodiments disclosed herein.

It is noted that very high levels of glycine, serine and formate (e.g. 5.0% w/v concentration in drinking water) were administered over four days ad libitum (e.g., 1 ml/day, although such amounts may vary on size and potential intake of each mouse). In some implementations, a glycerol-formate (gradual release) system may be used. In some implementations, a glycerol-glucose conjugate (gradual release with improved solubility) system may be used. In some implementations, other compounds with much lower toxicity may be capable of replicating this effect.

Example 7

In another exemplary method, treatment of HO HCU mice with a formate agent (e.g. sodium formate) significantly lowered plasma Hcy levels. In other exemplary methods, a formate agent was combined with standard HCU treatments in order to assess whether there were additive or synergistic effects of a formate agent when combined with the standard treatment. It was observed that treatment with formate alone reduced Hcy levels in the acceptable mouse model to greater levels that the standard treatment (e.g. betaine alone as previously observed to be about 15-25% reduction) and when combined with the standard treatment near normal levels of Hcy were observed. It is noted that these experiments were performed in the presence of a normal methionine/protein diet not a methionine reduced diet. Surprisingly, synergistic effects of the combination of agents were observed in these experiments reducing Hcy to normal or near normal levels in the presence of a normal protein diet.

Figure 11:
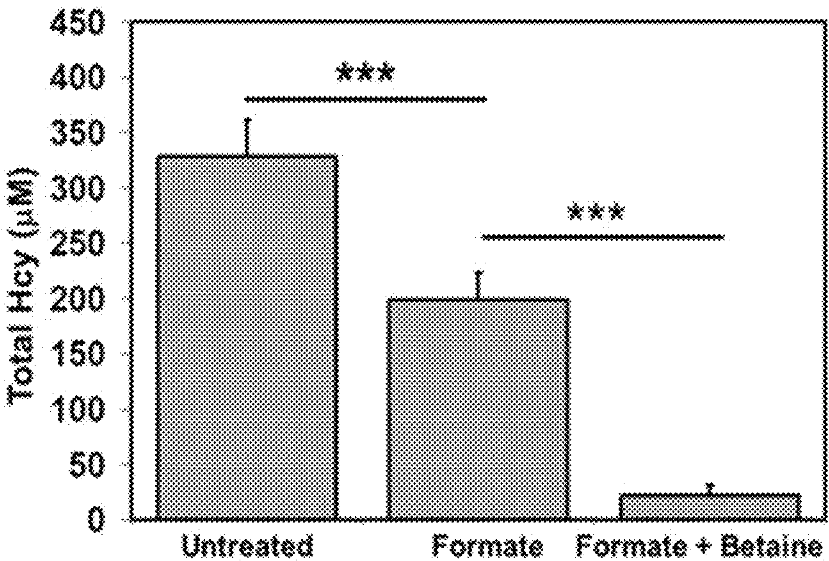
FIG. 11 represents a bar graph of level of homocysteine levels (Hcy) untreated (HO), treated (e.g. formate agent) and treated with standard treatment combinations (e.g. formate and trimethylglycine (e.g. betaine)) using the HCU mouse model in certain embodiments disclosed herein.

As found in FIG. 11, a histogram plot illustrates level of homocysteine levels (Hcy) in untreated (HO), treated (e.g. formate agent) and treated with standard treatment combinations (e.g. formate and trimethylglycine (e.g. betaine)) using the HCU mouse model in certain embodiments disclosed herein. Plasma Hcy levels were determined from HO HCU mice (n=8 per group) in the presence and absence of either about 5.0% w/v sodium formate alone or in combination with about 3.0% betaine given in drinking water given ad libitum. Results shown are representative of 3 independent experiments. *** denotes a P value of $<0.0001$.

Example 8

In another exemplary method, experiments were performed to measure levels of a critical enzyme in treated and untreated mouse models (HO). In these methods, a formate agent (e.g. sodium formate) was observed to restore normal expression levels of the critical enzyme, DMGDH, in HO HCU mice. In addition, when a formate agent was combined with standard treatment (e.g. betaine), response level for restoring DMGDH was surprisingly synergistic and conducive to improved lowering of homocysteine by betaine treatment.

Figure 12A:
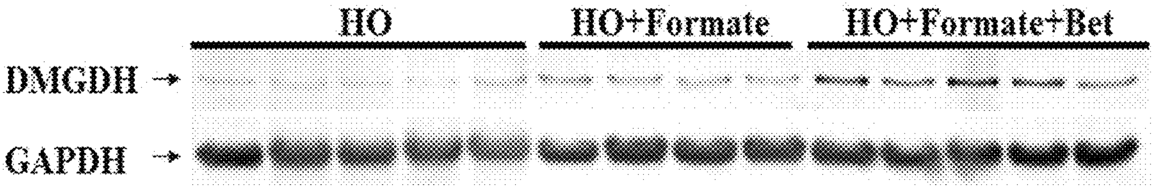
FIGS. 12A-12B represent a Western blot comparing the level of DMGDH and GAPDH (control) for untreated (HO), treated (e.g. formate agent) and treated with standard treatment combinations (e.g. formate and trimethylglycine (e.g. betaine)) using the HCU mouse model (FIG. 12A); and further illustrating in a histogram plot (FIG. 12B), level of intensity of DMDGH for untreated (HO), treated (e.g. formate agent) and treated with standard treatment combinations (e.g. formate and trimethylglycine (e.g. betaine)) using the HCU mouse model in certain embodiments disclosed herein.
Figure 12B:
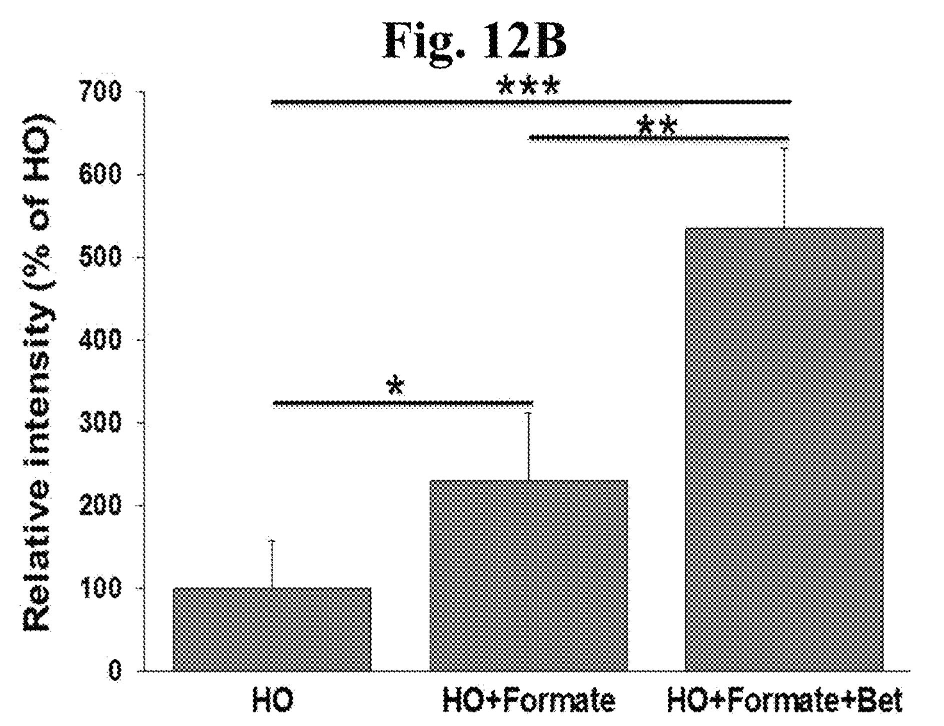

As shown in FIGS. 12A-12B, a Western blot comparing the level of DMGDH and GAPDH (control) for untreated (HO), treated (e.g. formate agent) and treated with standard treatment combinations (e.g. formate and trimethylglycine (e.g. betaine)) using the HCU mouse model (FIG. 12A); and further illustrating in a histogram plot (FIG. 12B), level of intensity of DMDGH for untreated (HO), treated (e.g. formate agent) and treated with standard treatment combinations (e.g. formate and trimethylglycine (e.g. betaine)) using the HCU mouse model in certain embodiments disclosed herein. Western blotting analysis of hepatic DMGDH protein levels in HO HCU mice in the presence and absence of either about 5.0% sodium formate alone or in combination with about 3.0% betaine given ad libitum in drinking water for about one week. N=9 per group. This figure is representative of three independent experiments.

Example 9

In another exemplary method, agents were used to verify involvement of BHMT in the homocystinuria treatment process. In these exemplary methods, a Cbs null mouse was used where severe liver damage to the mouse model interferes with standard HCU treatments to reduce Hcy. Using the Cbs null mouse model where severe liver damage abolished BHMT-mediated betaine response, it was observed that agents capable of reducing Hcy with and without standard treatment in the HO mouse model were unable to reduce Hcy in the Cbs null mouse model. It is noted that the tested formate agent, and amino acids, serine or glycine were unable to lower Hcy in the Cbs null mouse model. This data supports that at least part of the effect of these additional agents are BHMT dependent.

As represented in FIGS. 13A-13C, exemplary images in this example illustrate WT (FIG. 13A), Cbs null (−/−:BHMT mouse model knock out) (FIG. 13B) and HO (FIG. 13C) of liver samples obtained demonstrating level of tissue damage and further demonstrating that treatment response is at least BHMT dependent.

Example 10

In another exemplary method, zinc and zinc-containing agents were examined for effects on aberrant levels of homocysteine. It was known that there are significantly higher levels of BHMT protein in the long-term betaine treatment group where BHMT mediated remethylation of Hcy is diminished, this raised the possibility that the BHMT protein was impaired in its function. Previous work demonstrated that purified BHMT requires a thiol reducing agent for activity and that prolonged exposure of BHMT to buffers lacking reducing agents results in the slow irreversible loss of its catalytic zinc molecule and a corresponding loss of activity. In this context, further induction of BHMT expression observed in the long-term betaine treatment group could constitute a not entirely successful compensatory mechanism designed to mitigate the effects of diminished BHMT activity.

BHMT is unusual in that it constitutes approximately 2% of total protein in the liver. During long-term betaine treatment this rises to up to 8-10% of total hepatic protein which is an enormous amount of protein that would require zinc for its function. Zinc cannot be stored in mammals and must be replenished by the diet. However dietary sources of zinc are typically high in protein and therefore precluded by the low methionine diet. Therefore long term betaine treatment in HCU or other homocystinurias has the potential to induce zinc deficiency and thus impair BHMT protein function and concomitantly reduce the betaine response.

In one exemplary method, mice were given zinc in drinking water. For this example, 8 HO HCU mice were provided drinking water supplemented with zinc (e.g. 0.05% w/v Zinc sulfate) given ad libitum for one week. It was observed that this treatment resulted in an average 25% decrease in plasma homocysteine ($p<0.001$). When this treatment was combined with betaine (data not shown), zinc supplementation prevented the previously observed decrease in betaine efficacy during long term betaine treatment.

These data indicate that zinc supplementation is a novel strategy for improving treatment outcome in HCU and conceivably other forms of homocystinuria due to remethylation disorders. The use of zinc in HCU or these other diseases has never been proposed or reported in the literature. It is also contemplated that zinc can be combined with one or more of glycine, methylglycine, serine, histidine in combination with or without formate or formate derivative (e.g. triformin etc.) in the presence or absence of betaine to treat HCU and other homocysteine aberrant conditions.

FIG. 14 represents a histogram plot of homocysteine levels (Hcy) untreated and treated with zinc using the HCU mouse model in certain embodiments disclosed herein.

Example 11

In another exemplary method, hepatic ADH5 expression levels were examined in untreated (WT) mice and HO HCU mice in the presence and absence of formate (e.g. 5% w/v sodium formate in drinking water given ad libitum) treatment for one week (N=8, 4 of each sex, for each group). Under normal conditions, cellular concentration of folate-binding proteins exceeds that of folate derivatives, and therefore, the concentration of free folate in the cell is negligible. The provision of a significant excess of one-carbon donor compounds such as formate, serine, or glycine has the potential to change that situation and lead to the oxidation of folate species to formaldehyde which can be genotoxic. Cells express ADH5 to guard against the accumulation of toxic levels of formaldehyde. The detoxification of formaldehyde is initiated by the natural cellular antioxidant defense afforded by glutathione, which spontaneously reacts with formaldehyde to form S-hydroxymethylglutathione. Followed by NADP+-dependent oxidation of S-hydroxymethylglutathione to S-formylglutathione is catalyzed by ADH5. S-Formylglutathione is subsequently converted by S-formylglutathione hydrolase (FGH) to formate, which is then free to enter the one-carbon cycle. In addition to the conversion from formate, formaldehyde is also formed in the reaction catalyzed by dimethylglycine dehydrogenase as part of the betaine pathway. In certain exemplary methods, to reduce any adverse effects of formaldehyde formation and accumulation, co-administration of taurine and n-acetylcysteine can be used to treat HCU or NKU or other homocystinuria aberrant conditions. In part, these additional agents were able to boost available tissue and plasma levels of glutathione and likely boost formaldehyde detoxification.

Figure 15A:
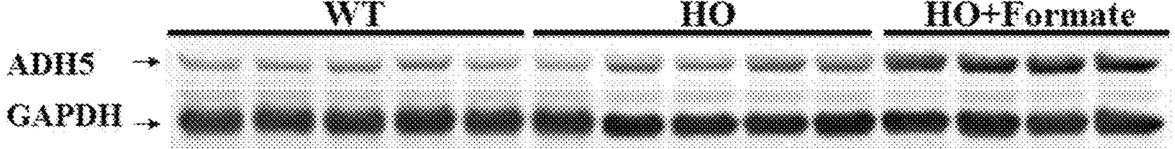
FIGS. 15A-15B represent a Western blot comparing the level of ADH5 and GAPDH (control) for wild type (WT), untreated (HO), and treated (e.g. formate agent) using the HCU mouse model (FIG. 15A); and further illustrating in a histogram plot (FIG. 15B), level of intensity of ADH5 for wild type (WT), untreated (HO), and treated (e.g. formate agent) using the HCU mouse model in certain embodiments disclosed herein.
Figure 15B:
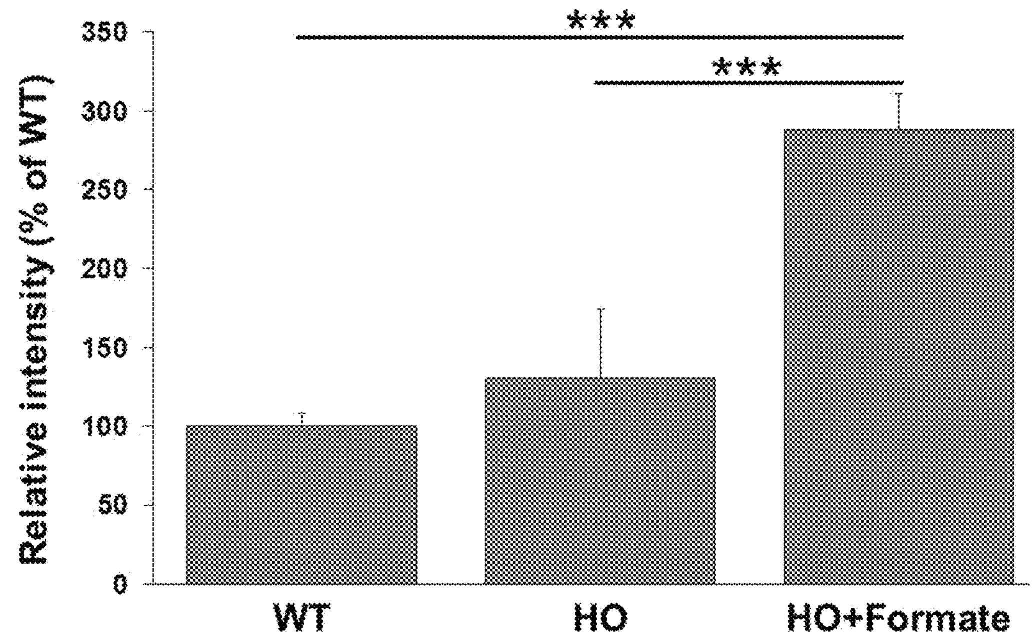

FIGS. 15A-15B represent a Western blot comparing the level of ADH5 and GAPDH (control) for wild type (WT), untreated (HO), and treated (e.g. formate agent) using the HCU mouse model (FIG. 15A); and further illustrating in a histogram plot (FIG. 15B), level of intensity of ADH5 for wild type (WT), untreated (HO), and treated (e.g. formate agent) using the HCU mouse model in certain embodiments disclosed herein.

Example 12

Figure 16:
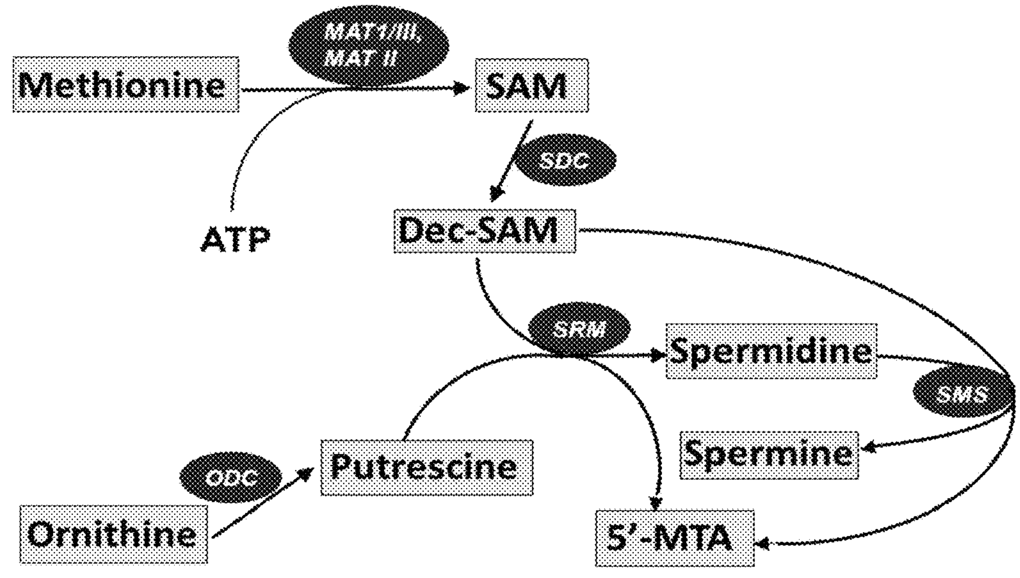
FIG. 16 is a schematic diagram representing polyamine synthesis and metabolism in mammalian liver of certain embodiments disclosed herein.

In another exemplary method, polyamines and/or diamines or combination regimens or compositions are contemplated herein of use to treat HCU or related condition. It is known that cystathionine beta-synthase (CBS: L-serine hydro-lyase (adding homocysteine), EC 4.2.1.22) is localized at a key regulatory branch point in the eukaryotic methionine cycle (FIG. 16). CBS catalyzes a pyridoxal 5'-phosphate dependent beta-replacement reaction condensing serine and homocysteine (Hcy) into cystathionine that is subsequently converted to cysteine in a reaction catalyzed by cystathionine $\gamma$-lyase (CGL, EC 4.4.1.1). Inactivation of CBS by mutation can result in classical homocystinuria (HCU) which in human subjects, is characterized by a range of connective tissue disturbances including marfanoid habitus and lens dislocation, intellectual impairment and a dramatically increased incidence of vascular disorders particularly thromboembolic disease.

As disclosed herein, a transgenic mouse model of HCU was able to recapitulate multiple aspects of the HCU phenotype including exhibiting a hypercoagulative phenotype and constitutive induction of multiple pro-inflammatory cytokines including tumor necrosis factor-alpha (TNF-$\alpha$) and interleukin-1beta (Il-1$\beta$) and altered apolipoprotein expression and function. This HO mouse model responds biochemically to the Hcy lowering effects of standard treatment (e.g. betaine) and one week of this treatment results in significant amelioration of the hypercoagulative phenotype and virtual ablation of most of the pro-inflammatory cytokine expression indicating this a highly relevant model to study both pathogenesis and treatment of the human disease.

It is known that the function of CBS is intrinsically linked to that of the methionine and folate cycle in mammals (FIG. 16). One function of the methionine cycle is the generation of S-adenosylmethionine (SAM) from methionine in a reaction catalyzed in the liver by methionine adenosyltransferase 1A (MAT1A). SAM is a physiologic methyl radical donor involved in enzymatic transmethylation reactions catalyzed by a wide range of methyltransferases including glycine N-methyltransferase (GNMT). This enzyme catalyzes the synthesis of N-methylglycine (MG aka sarcosine) from glycine using SAM as the methyl donor. This process generates S-adenosylhomocysteine (SAH), a powerful inhibitor of multiple cellular methylases. SAH is converted into homocysteine (Hcy) in a reaction catalyzed by S-adenosylhomocysteine hydrolase (SAHH). In HCU, the processing of Hcy to cysteine via transsulfuration is blocked due to inactivation of CBS and Hcy is either excreted into the extracellular space and from there, into plasma and urine, or remethylated back to methionine. The remethylation of Hcy occurs via two routes, one of which occurs primarily in the liver in a reaction catalyzed by betaine-homocysteine S-methyltransferase (BHMT) that uses betaine (trimethylglycine) as a methyl donor generating methionine and dimethylglycine (DMG). Alternatively, Hcy is remethylated to methionine via the action of the folate cycle. In this process, methylenetetrahydrofolate reductase (MTHFR) catalyzes the conversion of 5,10-methylenetetrahydrofolate to 5-methyltetrahydrofolate, (5-Me-THF). Subsequently, methionine synthase (MTR) catalyzes the conversion of 5-Me-THF and Hcy into methionine and tetrahydrofolate (THF). The folate cycle is completed by serine hydroxymethyltransferase that catalyzes conversion of serine to glycine and THF back to the MTHFR substrate 5,10-Methylenetetrahydrofolate (FIG. 19). In addition to its role in the methionine and folate cycles and serving as a substrate for methylation reactions, SAM plays a critical role in the synthesis of the polyamines spermine and spermidine.

HCU induces significant alteration of hepatic polyamine metabolism and accumulation of the biologically active sulfur-containing nucleoside MTA. Polyamines are a family of molecules including putrescine, spermine, and spermidine derived from ornithine. Polyamines play an important role in regulating cell growth and proliferation, the stabilization of negative charges of DNA, RNA transcription, protein synthesis, apoptosis, and the regulation of the immune response. More recently, evidence has begun to emerge that abnormalities in the control of polyamine metabolism might be implicated in multiple pathological processes relevant to HCU. Although the principal fate of SAM is its utilization as a methyl donor in biological methylation reactions, the decarboxylation of SAM in a reaction catalyzed by SAM decarboxylase (SDC) results in the formation of S-adenosylmethioninamine (Dec-SAM) which is used to donate aminopropyl groups during the endogenous synthesis of spermine and spermidine from putrescine.

In one exemplary method, using liver samples from our three experimental groups, it was determined the hepatic levels of putrescine, spermine and spermidine in WT mice and in HO HCU mice in the presence and absence of betaine treatment (n=8 per group). It was observed that no statistical difference in the hepatic levels of putrescine for any of the experimental groups (data not shown). Interestingly, it was observed that an approximate 60% and 70% decrease in hepatic spermidine and spermine content respectively ($p<0.001$ for both) in HO HCU mice relative to WT controls. The hepatic levels of both polyamines were normalized relative to WT mice by betaine treatment (FIG. 17A).

The involvement of Dec-SAM in polyamine metabolism in the synthesis of spermidine and spermine can lead to formation of the sulfur-containing nucleoside methylthioadenosine (5'-deoxy-5'-methylthioadenosine; adenine-9-β-D (5'-deoxy-5'-methylthio) ribofuranoside commonly abbreviated as MTA). This compound is a sulfur-containing nucleoside present in all mammalian tissues that behaves as a powerful inhibitory product in polyamine biosynthesis (FIG. 16). This compound is metabolized solely by MTA-phosphorylase, to yield 5-methylthioribose-1-phosphate and adenine, a crucial step in the methionine and purine salvage pathways, respectively. Determination of hepatic MTA levels in mice from the three experimental groups revealed that HCU induces a highly significant 250% increase in hepatic MTA levels compared to WT control mice ($P<0.001$, FIG. 17B). In contrast to spermine and spermidine, betaine treatment resulted in an approximate doubling of hepatic MTA levels compared to untreated HO HCU mice ($p<0.001$). Previous work has indicated a key pathogenic role for oxidative stress in HCU and multiple aspects of pathogenesis in this disease resemble accelerated senescence including mitochondrial dysfunction. If aspects of HCU induced pathogenesis are indeed related to a mitochondrial dysfunction linked accelerated aging phenotype, then the observed decrease in hepatic spermidine and spermine levels in HCU mice (FIG. 17A) is likely to be a contributory factor.

Figure 17A:
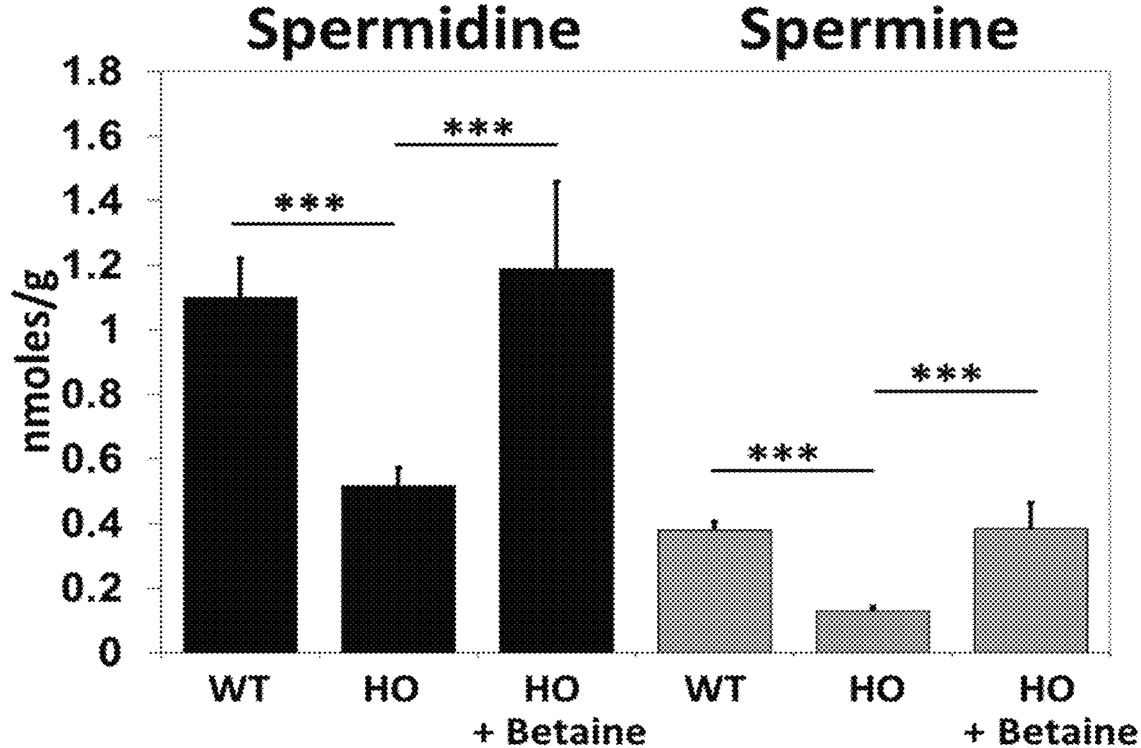
FIGS. 17A-17B represent exemplary experiments of hepatic spermidine and spermine levels (FIG. 17A) and MTA in WT and HO HCU mice in the presence and absence of one week of betaine treatment (n=8 for each group) (FIG. 17B) of certain embodiments disclosed herein.
Figure 17B:
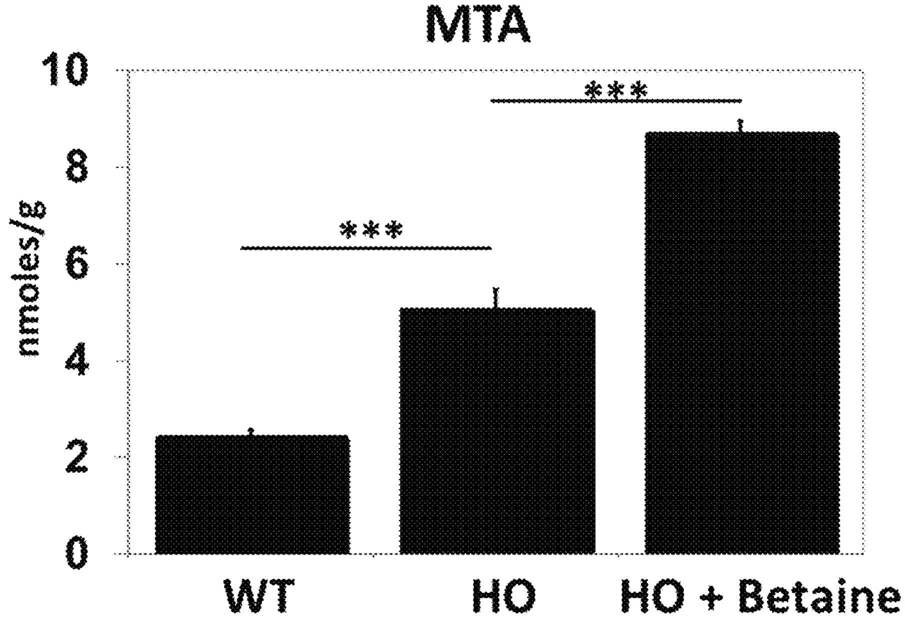

FIGS. 17A-17B illustrate significantly altered polyamine metabolism with decreased levels of hepatic spermine and spermidine while MTA is significantly increased. FIG. 16 illustrates the synthesis and metabolism of polyamines in the mammalian liver. Putrescine is formed from ornithine in a reaction catalyzed by ornithine decarboxylase (ODC). Subsequent polyamine synthesis starts with the decarboxylation of SAM by SAM decarboxylase (SDC), Decarboxylated SAM is a substrate for the aminopropytransferases spermidine synthase (SRM) and spermine synthase (SMS) that transfer the aminopropyl group of decarboxylated SAM to putrescine forming spermidine and spermine respectively. The synthesis of spermidine and spermine also results in the formation of the sulfur-containing nucleoside MTA (FIG. 17A) Hepatic spermidine and spermine and MTA in WT and HO HCU mice in the presence and absence of one week of betaine treatment (n=8 for each group) (FIG. 17B).

Example 13

In another exemplary method, spermidine and/or spermine supplementation can be administered to a subject having HCU or RD or other form of genetic homocystinuria. In this example, spermidine and/or spermine can be provided to a subject having HCU or RD or other form of genetic homocystinuria at about 0.1 mg/kg and 40 mg/kg per treatment for about 1 to about 3 times at mealtime. In other methods, these treatments can be combined with other treatments or used as alternating treatments in order to optimize control of aberrant homocysteine levels in a subject. It is contemplated herein that supplementations of spermidine and/or spermine to a subject having HCU or RD or other form of genetic homocystinuria can improve for example, bone density, cognition and/or improve abnormal platelet function and hypercoagulative phenotypes typically observed in a subject having HCU or RD or other form of genetic homocystinuria.

Example 14

Figure 18A:
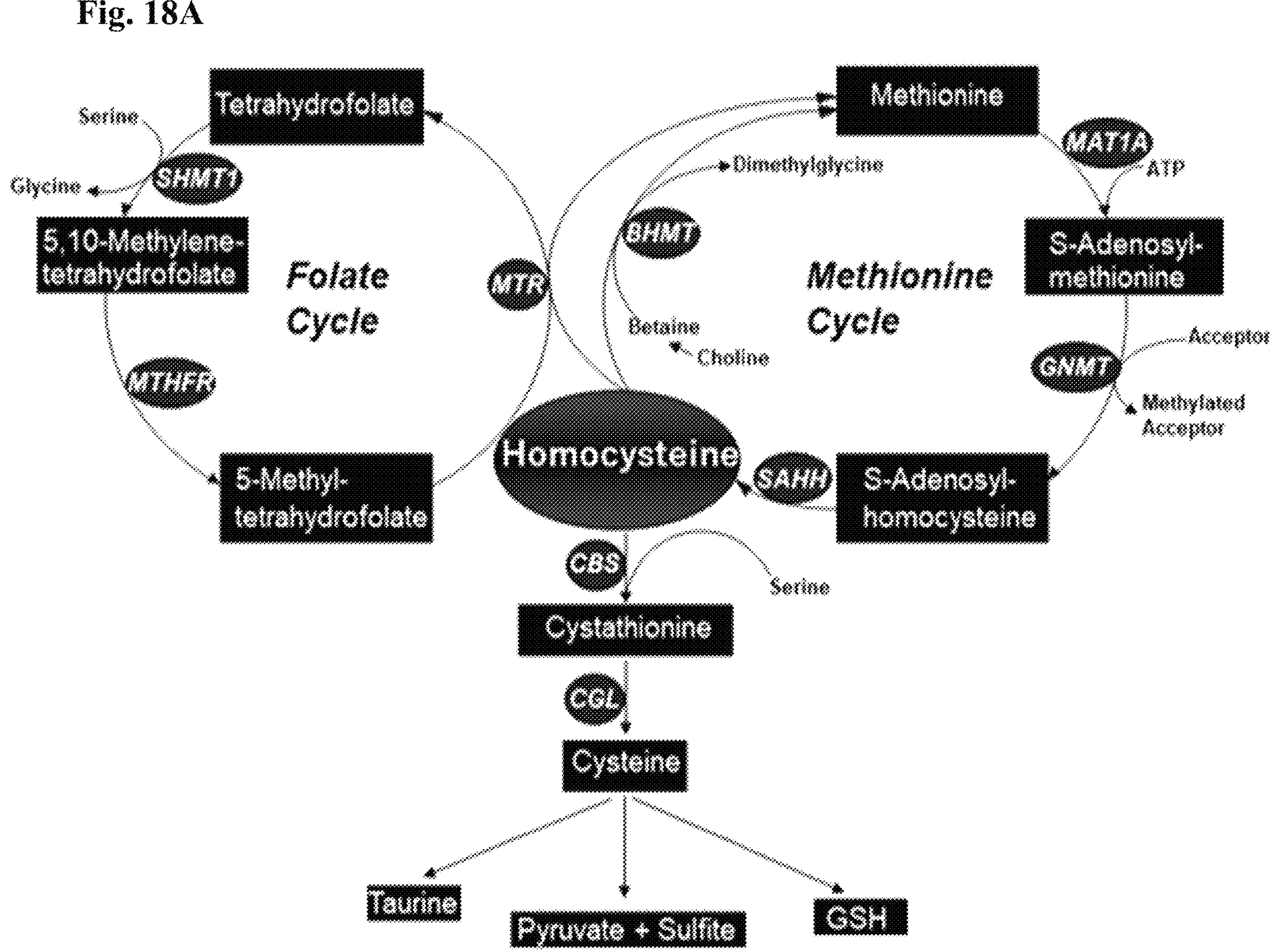
FIGS. 18A-18C represent an exemplary experiment of methionine and folate cycle in mammals where

In another exemplary method, the transsulfuration pathway and methionine-folate cycle pathways, as show in the sematic illustrated in FIG. 18A, were assessed. In brief, three experimental groups (n=8 for each group) of male mice consisting of either untreated WT controls or HO HCU mice in the presence or absence of betaine treatment. Betaine was administered by dissolving the compound in drinking water at 30 g/l and was supplied ad libitum to the mice for one week. Treatment water was replenished twice per week. The concentrations of betaine using the one-week treatment protocol with the HO model were found to significantly lower Hcy, increase ApoA-1 expression and decrease pro-inflammatory cytokine expression or ameliorate the dysregulation of cysteine oxidation pathways in HCU. The doses were well tolerated and did not limit water intake by mice which was important both in terms of animal welfare and avoiding possible confounding effects of dehydration.

A comparative reference data set was generated for these mice by examining plasma levels of tHcy, methionine, cysteine, serine, glycine, dimethylglycine, methylglycine (MG, SAM and SAH). In brief, determination of plasma levels of amino acids relevant to the methionine cycle were determined using methods similar to those described in Stabler et al., *Blood.* 81 (1993) 3404-3413, incorporated in its entirety herein. Determination of hepatic 5-methylTHF was performed by liquid chromatography-tandem mass spectrometry using methods similar to those described in Witham et al., *PLoS One.* 8 (2013) e77923, incorporated in its entirety herein. The global metabolomic analysis of methionine and folate cycle related metabolites was carried out by Metabolon, Inc. Briefly, sample preparation was performed utilizing the automated MicroLab STAR® system. Sample preparation was performed using a proprietary series of organic and aqueous extractions to remove the protein fraction while allowing maximum recovery of small molecules. The resulting extract was divided into two fractions: one for analysis by liquid chromatography and one for analysis by gas chromatography. Each sample was then frozen and dried under vacuum. The LC/mass spectrometer portion of the platform was based on a Waters ACQUITY UPLC and a Thermo-Finnigan LTQ mass spectrometer, which consisted of an electrospray ionization source and linear ion-trap mass analyzer. Samples were analyzed on a Thermo-Finnigan Trace DSQ fast-scanning single-quadrupole mass spectrometer using electron impact ionization. Identification of known chemical entities was based on comparison to library entries of authenticated standards. Tissue polyamines putrescine, spermidine and spermine and 5-methylthioadenosine (MTA) were determined by liquid chromatography-tandem mass spectrometry using methods similar to those described in Stevens et al., *J Chromatogr* A 1217 (2010) 3282-3288, incorporated in its entirety herein.

Figure 18B:
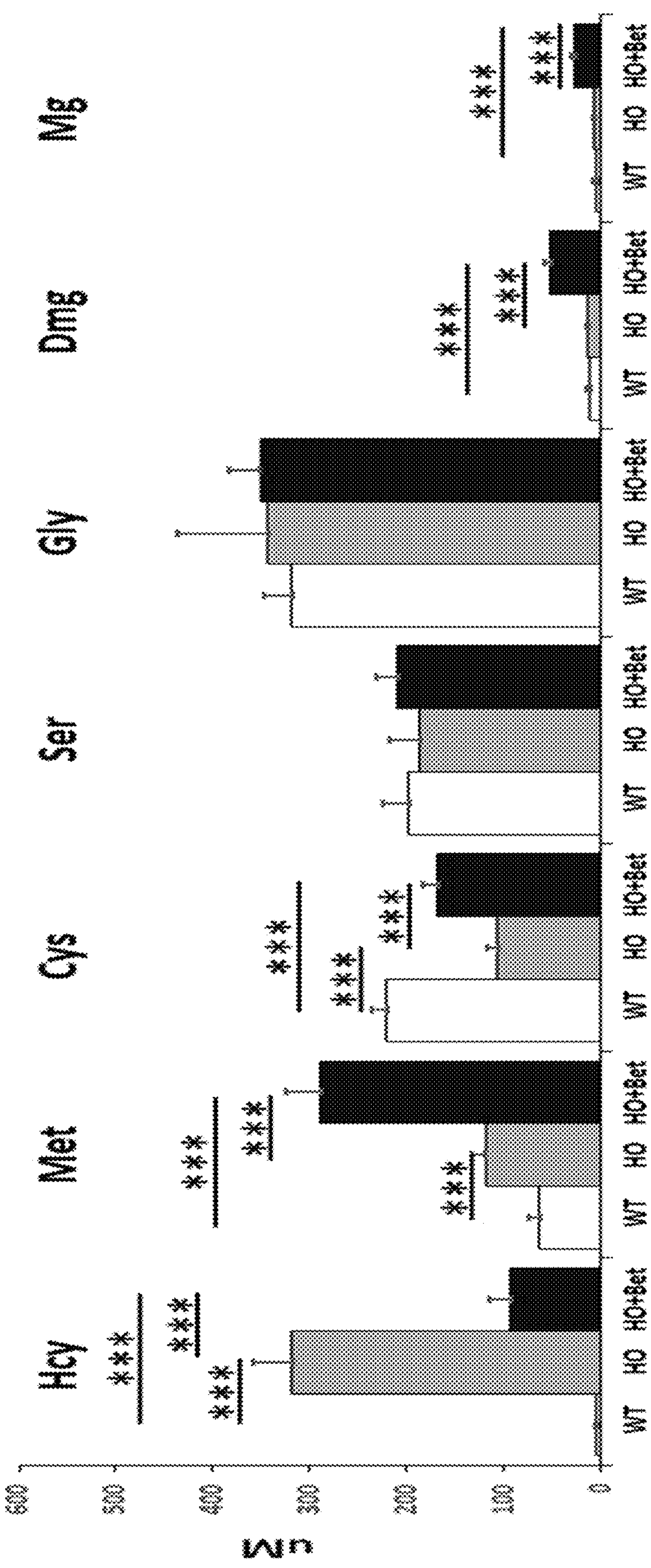
Figures 18C, 19A:
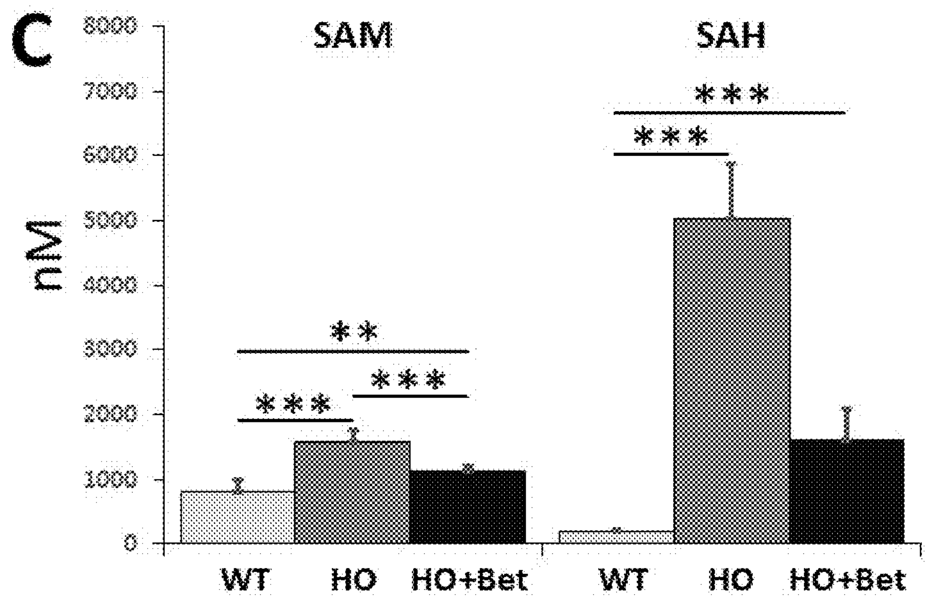
FIGS. 19A-19C represent a comparative metabolomic analysis of liver samples between WT and HO HCU mice in the presence and absence of betaine treatment (FIG. 19A); a Western blot and a histogram plot of level of intensity comparing the level of MAT1A and GAPDH (control) for wild type (WT) and HO mice treated with betaine (FIG. 19B); and a Western blot and a bar graph of level of intensity comparing the level of SAHH and beta-actin (control) for wild type (WT) and HO mice treated with betaine (FIG. 19C) of certain embodiments disclosed herein.
Figure 19B:
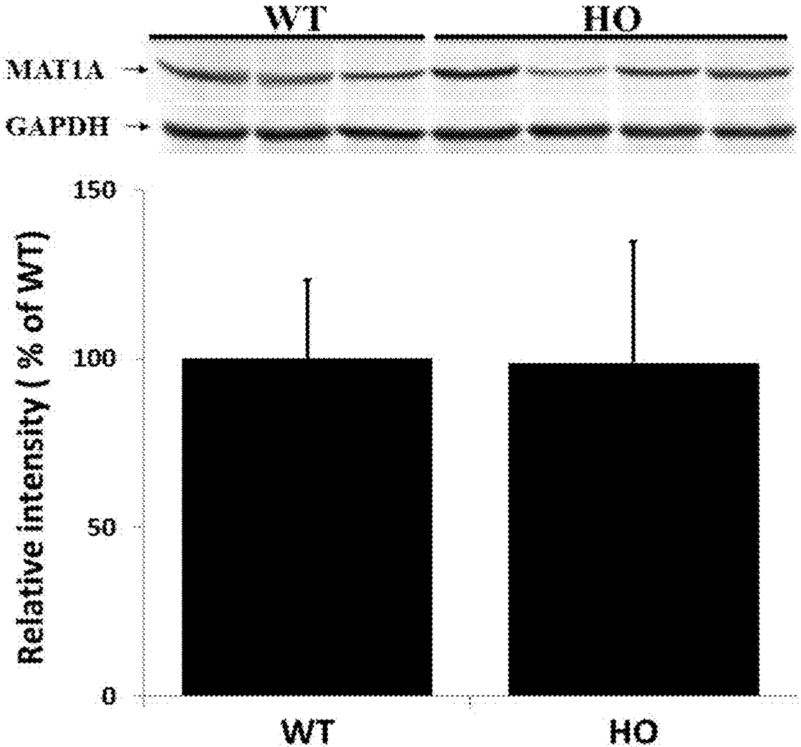

In this analysis (FIG. 18B), an approximate 57-fold increase in tHcy was observed in untreated HO mice compared to WT controls ($P<0.0001$). Treatment of HO HCU mice with betaine for one week resulted in an approximate 60% decrease in tHcy ($P<0.0001$), which remained significantly elevated compared to WT controls ($P<0.0001$). Plasma Met levels were effectively doubled ($P<0.0001$) and were increased 3-fold compared to untreated HCU mice as a consequence of betaine treatment. Plasma total cysteine levels were approximately half that observed in WT controls ($P<0.0001$). This depletion was significantly ameliorated by betaine treatment ($P<0.0001$); however, plasma levels of cysteine remained significantly lower than the WT control ($P<0.0001$). Serine and glycine did not change significantly in any of the experimental groups. DMG and MG in untreated HO mice did not differ significantly from WT ($P=0.552$ and 0.348 respectively) but were both strongly increased a consequence of betaine treatment ($P<0.0001$). Plasma SAM and SAH levels in untreated HO mice were increased approximately 2 and 24-fold respectively compared to WT controls ($P<0.0001$) (FIG. 18C). Both of these metabolites were significantly decreased, but not normalized, by betaine treatment ($P<0.0001$ for both).

In the hepatic metabolomic analyses of the three experimental groups (n=8 for each group) an approximate 10-fold increase in hepatic tHcy was observed. The scale of this elevation compared to WT controls was significantly lower than that observed in plasma but it was lowered by approximately 20% by one week of betaine treatment. Additionally, it was observed that HCU induced a significant (131%, $P<0.05$) increase in methionine levels in untreated HO mice (FIG. 19A). In contrast to the plasma data, betaine treatment had no detectable effect upon the hepatic levels of this amino acid compared to untreated HO mice. In addition to methionine, the present disclosure reported for the first time that HCU also significantly increased the hepatic level of the methionine derivative compounds, N-formylmethionine (230%), methionine sulfoxide (283%) and N-acetlymethionine (273%) ($P<0.05$ for all metabolites). Betaine treatment significantly lowered the latter of these compounds (23%) compared to untreated HO HCU mice. Similar to what was observed in plasma, it was observed that SAM and SAH were significantly increased in the HO HCU mouse liver. In contrast to what was observed in plasma, SAM and SAH did not change significantly in HO HCU mice as a consequence of betaine treatment. Collectively, the data indicated that liver levels of multiple potentially deleterious methionine cycle metabolites remain high and, in multiple cases, did not show the same response to betaine treatment as that observed in plasma.

In addition to methionine cycle metabolites, the metabolomic analysis also provided data on the end product of transsulfuration, cysteine and both its related derivatives and oxidation products. In common with the plasma data described herein, it was observed that HCU induced a significant 42% decrease in the hepatic level of cysteine. An even greater 77% decrease was observed for N-acetylcysteine. The methylated derivative S-methylcysteine was increased by 322% compared to WT control mice as a consequence of HCU. The cysteine oxidation product hypotaurine was significantly decreased as a consequence of HCU but the N-amidino derivative of taurine taurocyamine and N-acetyltaurine were significantly increased in HCU liver by 166% and 321% respectively. This was the first ever report that HCU induced significant changes in hepatic N-acetylcysteine, taurocyamine and N-acetyltaurine levels. Of these changes, only the decrease in cysteine and N-acetylcysteine were reversed by betaine treatment.

To date there has never been an extensive analysis of the effect of HCU upon the expression levels of the enzymes involved in the methionine and folate cycles. Given the profound metabolic changes induced by deletion of CBS, alteration in the expression patterns of some of these enzymes was assessed by qRT-PCR analysis of liver samples from the WT and untreated HO cohorts (n=8 for each group). RNA was isolated using an RNeasy mini kit according to the manufacturer's standard protocol. Extracted RNA (200 ng) was treated with RNase-free DNase and reverse-transcribed using random hexamers. Real-time quantitative reverse transcriptase PCR (qRT-PCR) was performed using cDNA samples diluted 1:4, and 1 μl was used in each 20 μl qRT-PCR reaction and SYBR Green PCR Master Mix. Transcript levels were analyzed on a Light Cycler 480 System II over 40 cycles of 95° C. for 10 seconds, 60° C. for 10 seconds, and 72° C. for 15 seconds, preceded by an initial 5 minute step at 95° C. GAPDH was used as the normalizing endogenous control gene to standardize qRT-PCR data. All real-time qRT-PCR data were generated using RNA isolated from tissues of individual animals (n=8/group) and mouse gene specific primers:

```
MTR
(forward 5'-GCTCTGTGAAGACCTCATCTGG-3' (SEQ ID
NO: 1),

reverse 5'-GAGCCATTCCTCCACTCATCTG-3')(SEQ ID
NO: 2)),
```

-continued

```
MAT1A
(forward 5'-CCTTCTCTGGAAAGGACTACACC-3' (SEQ ID
NO: 3),

reverse 5'-GACAGAGGTTCTGCCACACCAA-3' (SEQ ID
NO: 4)),

GNMT
(forward 5'-TGGTGATCGACCACCGCAACTA-3' (SEQ ID
NO: 5),

reverse 5'-GTCGTAATGTCCTTGGTCAGGTC-3' (SEQ ID
NO: 6)),

SAHH
(forward 5'-CAGGCTATGGTGATGTGGGCAA-3' (SEQ ID
NO: 7),

reverse 5'-CCTCCTTACAGGCTTCGTCCAT-3' (SEQ ID
NO: 8)),

MTHFR
(forward 5'-TACCTCTCTGGAGAGCCGAATC-3' (SEQ ID
NO: 9),

reverse 5'-GGCTGAGAGTTGATGGTGAGGA-3' (SEQ ID
NO: 10)),

SHMT1
(forward 5'-CTGGAGATGCTGTGTCAGAAGC-3' (SEQ ID
NO: 11),

reverse 5'-TGAGGCTCTACCAGGGCAGTAT-3' (SEQ ID
NO: 12)).
```

No significant change in the mRNA levels of MTR, MAT1A, SAHH, GNMT, SAHH, MTHFR, MTR and SHMT1 was observed using this method (data not shown).

Figure 19C:
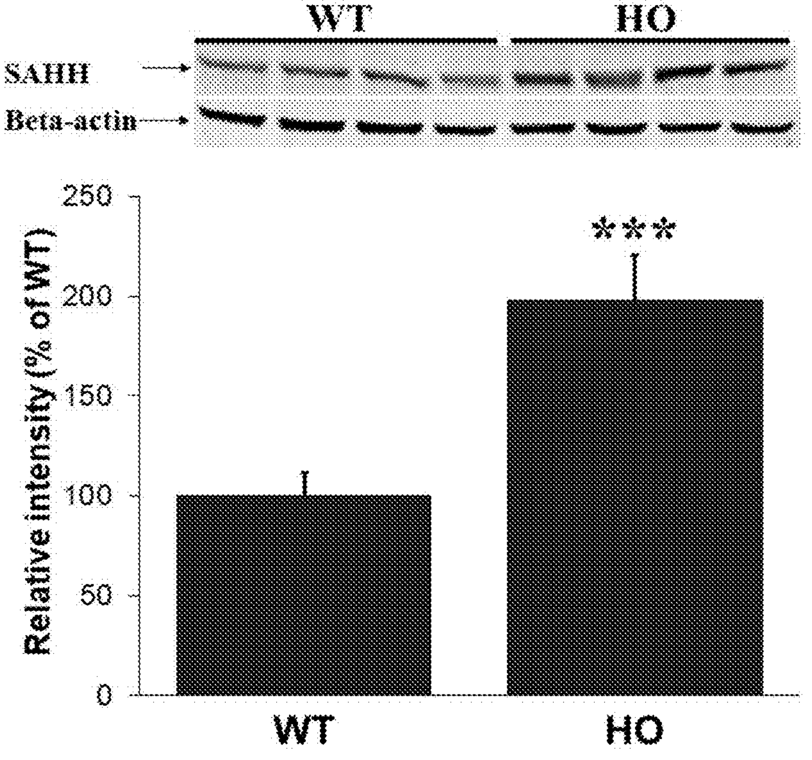

To further characterize the effects of HCU upon methionine cycle metabolism, Western blotting analysis of the protein levels of the methionine cycle proteins MAT1A, GNMT and SAHH was performed using WT and untreated HCU mouse liver samples. No significant change in MAT1A (FIG. 19B) and GNMT (data not shown) protein levels were observed but hepatic levels of SAHH were strongly induced and effectively doubled (FIG. 19C).

Example 15

Figure 20A:
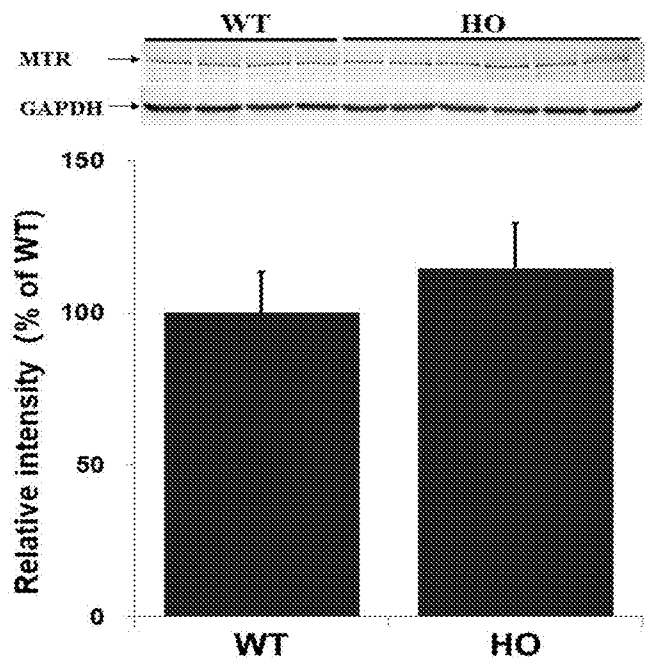
FIGS. 20A-20C represent Western blotting analysis of hepatic MTR (FIG. 20A) and MTHFR (FIG. 20B) protein levels and hepatic 5-Me-THF levels in WT and HO HCU mice (FIG. 20C) of certain embodiments disclosed herein.
Figure 20B:
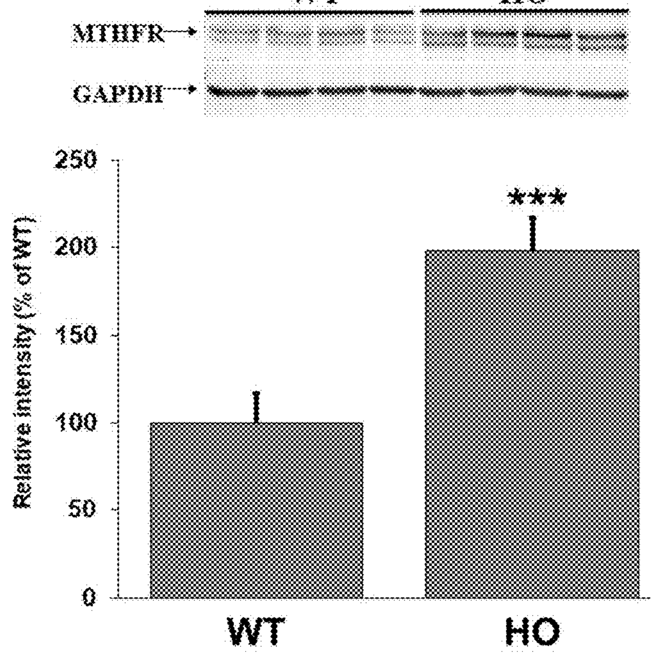
Figure 20C:
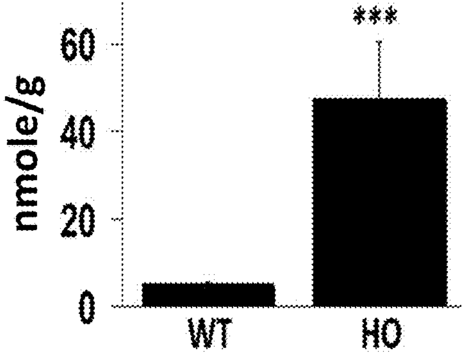

In another exemplary method, effect of HCU upon the enzymes of the folate cycle was assessed. In brief, using Western blotting analysis, the abundance of MTHFR and MTR protein levels in liver samples from WT controls and untreated HO HCU mice was examined. It was observed that hepatic expression of MTR was unaffected but that expression of both the phosphorylated and non-phosphorylated forms of MTHFR were induced approximately 2-fold by HCU (FIGS. 20A and 20B). Next, hepatic 5-methylTHF levels were determined by liquid chromatography-tandem mass spectrometry. Determination of hepatic 5-Me-THF levels indicated that HCU induced an approximate 10-fold accumulation of 5-me-THF with the potential to unbalance cellular folate pools and act to cause a decrease in available THF (FIG. 20C), confirming that the induction of MTHFR without any discernible change in MTR expression has could dysregulate folate metabolism and cause an accumulation of 5-Me-THF.

MTHFR activity is the rate-limiting step in the remethylation of Hcy via the folate cycle. BHMT is repressed in HCU mice and the scale of that repression is inversely proportional to the degree of Hcy elevation. In order to investigate for existence of a reciprocal relationship between the two competing Hcy remethylation pathways, BHMT and MTHFR protein levels were examined as a function of elevated tHcy in these mice, designated either low tHcy HO HCU (mean tHcy: 54.1 μM±27.6; n=5), or medium tHcy HO (mean tHcy: 223.9.2 μM±9.3; n=4) and high tHcy HO HCU mice (mean tHcy: 328.6 μM±52.2; n=4). Observed was a direct relationship between the degree of tHcy elevation and hepatic MTHFR protein levels ($R^2$=0.6052, P<0.01, FIGS. 21A and 21B). In the same liver samples, observed was a strikingly clear inverse relationship between BHMT protein levels and plasma tHcy levels ($R^2$=0.6282, P<0.01, FIGS. 21A and 21C). Taken together, these findings indicate a likely reciprocal regulatory mechanism between competing Hcy remethylation pathways in HCU.

In another exemplary method, another component of the folate cycle examined herein was SHMT. This enzyme converts serine and THF into glycine and 5,10-methyleneTHF (FIG. 18A). Mammals have both a cytosolic form (SHMT1) and a mitochondrial form (SHMT2) of the enzyme. To date, there has been no investigation of the effect of HCU upon the expression levels of either SHMT isoforms. Western blotting analysis of hepatic SHMT1 protein levels in WT and HO mice demonstrated no significant change in expression as a consequence of HCU (FIG. 22A). The mitochondrial isoform SHMT2 was significantly repressed by approximately 40% (FIG. 22B, P<0.01) indicating that these enzymes are differentially regulated in HCU.

To assess effects of HCU in this component of metabolism, targeted metabolomics of hepatic serine, glycine and their related metabolites were assessed. Similar to what was observed in HO HCU plasma, (FIG. 18B) no significant change in hepatic glycine, DMG and MG levels in untreated HO mice relative to WT controls was observed (FIG. 22C). DMG and MG were 3 to 4-fold increased as a consequence of betaine treatment. In contrast to what was observed in plasma, there was a statistically significant 132% and 204% increase in hepatic serine and N-acetylserine levels respectively as a consequence of HCU (P<0.05, n=8 for both). Neither of these metabolites were significantly altered by betaine treatment. Collectively, these results showed significant alteration of serine metabolism as a consequence of HCU and reiterated the point that plasma data does not always provide an accurate picture of the metabolic disturbances in tissues.

Example 16

In another exemplary method, the effects of betaine and taurine in HCU were assessed. Current treatment for HCU typically consists of a methionine-restricted diet combined with betaine treatment as noted previously. Betaine treatment lowers tHcy levels by serving as a methyl donor in the remethylation of Hcy to methionine and DMG catalyzed by BHMT, and is effective in significantly lowering plasma tHcy in both humans and HO HCU mice (FIG. 18B). HCU induced significant alteration in the synthesis of taurine, and supplementation with taurine effectively normalized HCU-induced disturbances in glutathione metabolism and the gamma-glutamyl cycle, enhances the efficacy of betaine treatment in mice, and acts to completely ablate endothelial dysfunction in human HCU patients.

To investigate the effects of these treatments upon the hepatic regulatory changes in enzyme expression induced by HCU, the human transgenic HO mouse model of HCU was used. In brief, experimental groups consisting of 8 HO mice on a C57BL/6J background and 8 C57BL/6J WT littermate control mice bred in house were used. Mice in both groups were male and aged between 3 and 4 months. Except where otherwise stated, all mice were maintained on standard chow. All diets were administered using a paired-feeding design to ensure isocaloric intake between all experimental groups and body weights were measured once per week. There was no significant difference in body weight between mice in any of the experimental groups. Betaine and taurine were in this example, both administered by dissolving these compounds in drinking water at 30 g/l (2% or 3% w/v) and were supplied ad libitum for one week. Treatment water was replenished twice per week. The concentrations of betaine, taurine and one-week treatment protocol with the HO model were found to significantly lower Hcy, increase ApoA-1 expression and decrease pro-inflammatory cytokine expression (betaine) or ameliorate the dysregulation of cysteine oxidation pathways in HCU. The doses were well tolerated and do not limit water intake by mice which was important both in terms of animal welfare and avoiding possible confounding effects of dehydration.

Western blotting analysis of SAHH, MTHFR and SHMT2 expression was performed in liver samples from HO mice in the presence and absence of betaine or taurine treatment. In this analysis, it was observed that betaine treatment completely reversed the HCU-mediated induction of SAHH and MTHFR expression ($P<0.05$) (FIGS. 23A and 23B, respectively). Similarly, betaine treatment completely reversed the repression of hepatic SHMT2 induced by HCU (FIG. 23C) ($P<0.01$). When the analyses were extended to compare the effects of taurine treatment upon the expression levels of these enzymes, an essentially identical reversal of the HCU-induced regulatory changes as that observed with betaine treatment was observed (FIGS. 23D-23F).

Figure 24A:
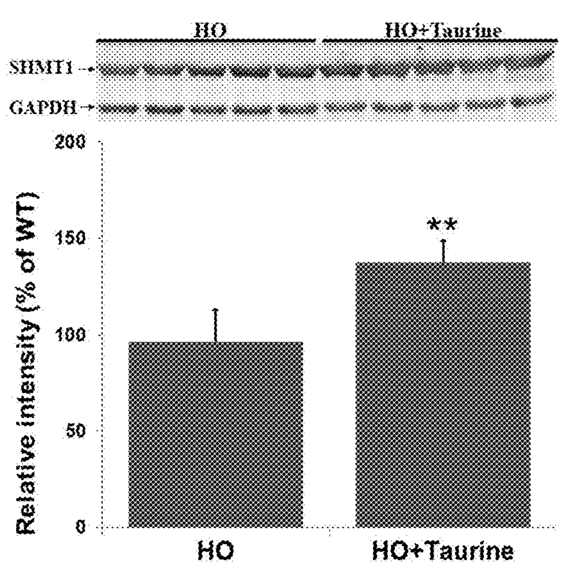
FIGS. 24A-24C represent Western blotting analysis and bar graphs of hepatic SHMT1 protein levels (FIG. 24A) in HO mice in the presence and absence of taurine treatment; and MAT1A (FIG. 24B) and GNMT (FIG. 24C) protein levels in HO HCU mice in the presence and absence of one week of betaine or taurine treatment of certain embodiments disclosed herein.
Figure 24B:
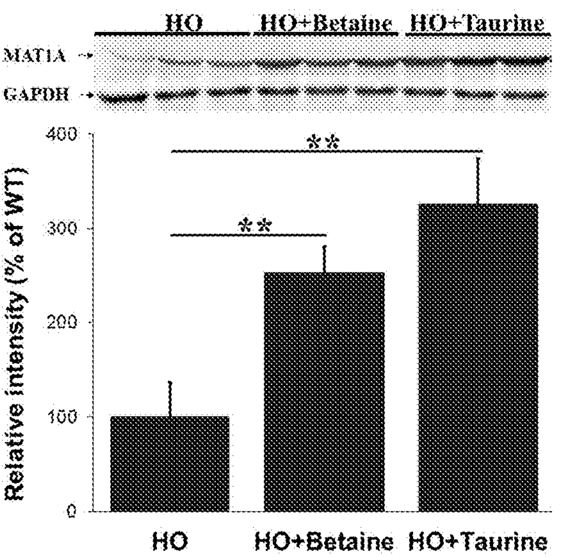
Figure 24C:
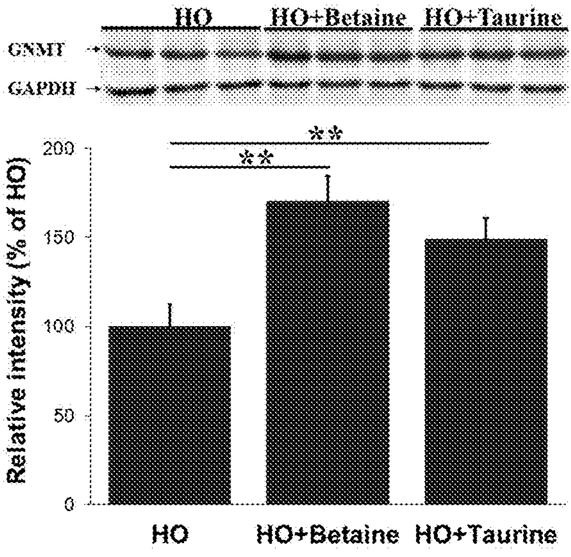

In addition to studying the effects of betaine and taurine upon enzymes that were altered in expression due to HCU, the analyses herein also included an assessment of hepatic expression of those enzymes that did not exhibit any HCU induced derangement. In this analysis, it was observed that taurine, but not betaine, induced a small but statistically significant 35% increase in SHMT1 expression (FIG. 24A). Similarly, it was observed that both betaine- and taurine-induced expression of both MAT1a and GNMT in the livers of HO HCU mice (FIGS. 24B-24C). These observations are the first to report betaine and taurine acting to regulate expression of these processes. Therefore, this observation supports that taurine alone or in combination with betaine and other treatments for genetic homocystinuria are viable options for avoiding dietary restraints and treating these conditions.

Example 17

Figures 25, 26:
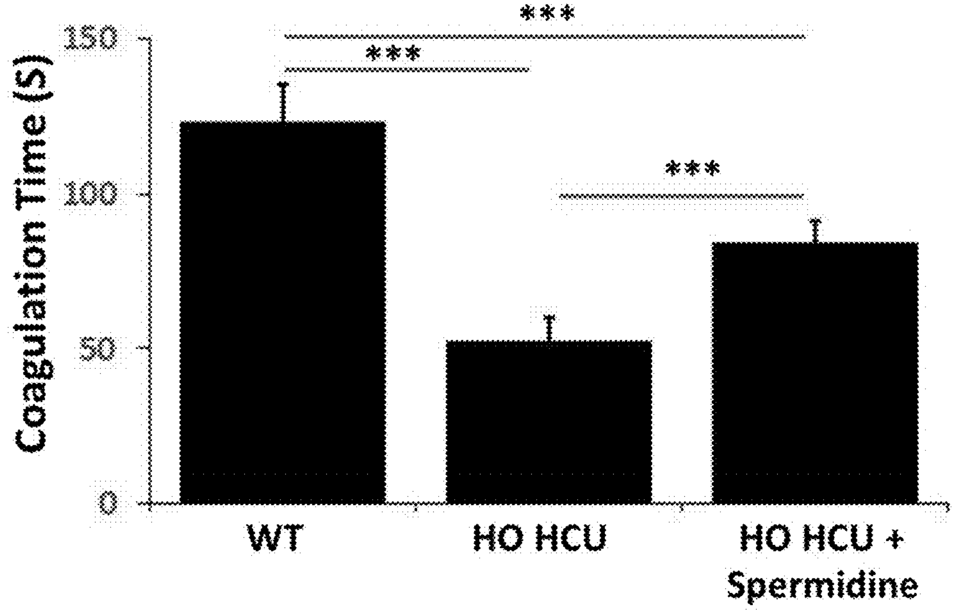
FIG. 25 illustrates a comparative table of plasma tHcy and hepatic SAHH, MTHFR, BHMT expression in mice that were CBS or MTR deficient of certain embodiments disclosed herein.
FIG. 26 illustrates a representative bar graphs of tail bleeding times to assess coagulation time for HO HCU and wild type (WT) control mice and HO HCU after mice one week of spermidine treatment of certain embodiments disclosed herein.

In another exemplary method, in addition to serving as a marker of mitochondrial dysfunction and accelerated senescence, methionine sulfoxide could be contributing to pathogenesis in HCU directly. The reversal of the HCU changes in expression of SAHH, MTHFR, BHMT and SHMT2 by the Hcy lowering treatment observed herein could be this metabolite playing a key role in these changes. However, it was striking that these changes were diametrically opposed to those previously observed in female (but not male) Cgl null mice that also exhibited severely elevated plasma tHcy around 200 μM (FIG. 25). These latter mice exhibited severely elevated tHcy as a consequence of a 70% decrease in hepatic MTR expression and served as a mouse model of homocystinuria due to a remethylation defect. Comparison of the regulatory changes induced by severely elevated Hcy in these two models (FIG. 25) served to indicate that the changes in methionine and folate gene expression induced by homocystinuria were influenced by the mechanism by which the elevation of that metabolite occurs, consistent with the observation that taurine treatment was capable of reversing all of the changes induced by HCU in SAHH, MTHFR and SHMT2 expression with only a mild effect upon lowering plasma tHcy levels.

The folate cycle is intimately connected to one-carbon metabolism. The induction of MTHFR in proportion to tHcy elevation and the concomitant accumulation of 5-Me-THF can significantly impact one-carbon metabolism by limiting the pool of available THF and conceivably, impair the betaine response over time. The following addresses such a condition and proposes new options for treatments/supplementation of subjects having genetic homocystinuria or other related condition affecting these pathways.

Example 18

In another exemplary method, effect of polyamines (e.g. spermidine and spermine) on the hypercoagulative phenotype induced by HCU was assessed which is a measure of treatment for genetic HCU where rapid coagulation is a side effect of these conditions. In brief, mice containing both the human CBS transgene and no functional copy of the mouse equivalent gene were identified by PCR from the litters of progeny of 11181×$MKO^{+/-}$ F1 mice backcrossed to $MKO^{+/-}$ mice. These mice were designated as "human only" (HO) mice and used as a human model of HCU. Tail bleeding time determinations demonstrated that, like human HCU patients, HO HCU mice exhibited a hypercoagulative phenotype that responded to betaine treatment (data not shown).

In order to further investigate the possible therapeutic potential of polyamine (e.g. spermidine and spermine) therapy in HCU, WT and HO HCU mice were given either: one week of spermidine treatment given orally as a 4 mM solution in drinking water given ad libitum; one week of spermine treatment given orally as a 4 mM solution in drinking water given ad libitum; or drinking water (untreated, control). After one week, tail bleeding times were determined for untreated wild type (WT) control B6 mice and HO HCU mice from all treatment groups.

Figure 27:
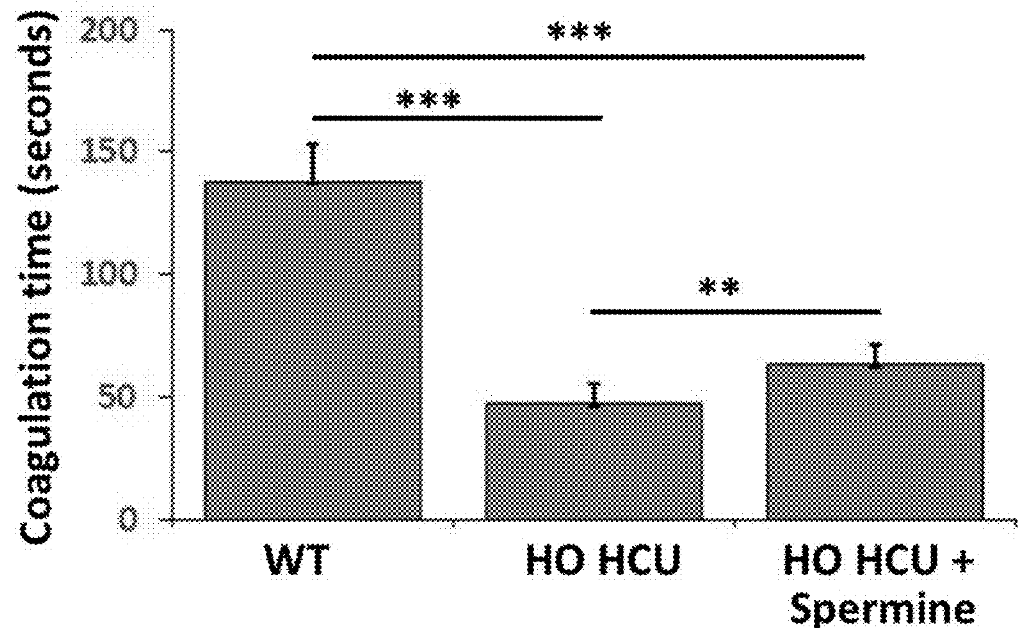
FIG. 27 illustrates a representative bar graph of tail bleeding times to assess coagulation for HO HCU and wild type (WT) control mice and HO HCU after mice one week of spermine treatment of certain embodiments disclosed herein.

In these experiments, it was found that that the untreated HO mice clotted approximately 2.5-fold faster than the wild type controls (FIGS. 26 and 27) ($p<0.0001$) indicating that these mice were in a hypercoagulative state. One week of spermidine treatment in HO mice was accompanied with a highly significant increase in clotting time compared to untreated HO mice (FIG. 26) ($p<0.0001$). The hypercoagulative state in HO HCU mice was also significantly ameliorated ($P<0.01$) after one week of spermine treatment (FIG. 27). These results indicate that supplemental polyamines such as spermidine and/or spermine have considerable therapeutic potential in HCU to treat this condition and reduce side effects. It is contemplated that these agents can be used as supplements alone or in combination with other treatments (e.g. betaine, folate, glycine, serine, zinc or copper or other agent used to treat genetic homocystinuria or similar condition)

All of the COMPOSITIONS and METHODS disclosed and claimed herein may be made and executed without undue experimentation in light of the present disclosure. While the COMPOSITIONS and METHODS have been described in terms of preferred embodiments, it will be apparent to those of skill in the art that variation may be applied to the COMPOSITIONS and METHODS and in the steps or in the sequence of steps of the METHODS described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A pharmaceutical composition, comprising:

a first agent comprising one or more of a polyamine, diamine or polyamine derivative or precursor thereof;

a second agent for treating a subject having genetic homocystinuria comprising at least one of trimethylglycine or derivative thereof, formate, formate salt, diformylglycerol or derivative thereof, taurine, n-acetylcysteine, and zinc conjugate or zinc delivery agent or copper; and a pharmaceutically acceptable excipient.

2. The composition according to claim 1, wherein the first agent comprises one or more of spermine, spermidine, putrescine, hypusine, and cadaverine.

3. The composition according to claim 1, wherein the second agent comprises trimethylglycine or derivative thereof.

4. The composition according to claim 1, wherein the second agent comprises formate, formate salt, diformylglycerol or derivative thereof, zinc conjugate or zinc delivery agent or copper, or combinations thereof.

5. The composition according to claim 4, wherein the formate, formate salt, diformylglycerol or derivative thereof comprises diformylglycerol-glucose or derivative thereof; triformyl glycerol or derivative thereof; diformylglycerophosphocholine or derivative thereof; diformylglycerophosphoethanolamine or derivative thereof; or combinations thereof.

6. The composition according to claim 1, wherein the composition is formulated into a powder, a food additive, a beverage additive, a capsule, tablet, a gum, a slow-releasing patch, a time-released patch or an aqueous solution.

7. The composition according to claim 1, wherein the polyamine, diamine or polyamine derivative or precursor thereof comprises about 0.1 mg/kg to about 100 mg/kg per dose.

8. The composition according to claim 1, wherein the composition further comprises a flavoring.

9. The composition according to claim 1, wherein the second agent comprises at least one of taurine and n-acetylcysteine.

10. The composition according to claim 9, wherein the genetic homocystinuria in the subject comprises classical cystathionine beta-synthase (CBS) deficient homocystinuria (HCU) or other genetic forms of homocystinuria due to mutations in either methylenetetrahydrofolate reductase or methionine synthase or deficiencies in cobalamin transport and/or metabolism (referred to as remethylation disorders (RD)).

11. The composition according to claim 1, further comprising a third agent comprising one or more of trimethylglycine or derivative thereof, formate, formate salt, diformylglycerol or derivative thereof, taurine, n-acetylcysteine, and zinc conjugate or zinc delivery agent or copper.

12. The composition according to claim 1, wherein the composition comprises at least one of spermidine and spermine, at least one of trimethylglycine or derivative thereof, and at least one of formate, formate salt, diformylglycerol or derivative thereof.

13. A method of treating a subject having genetic homocystinuria, the method comprising: administering an effective amount of a pharmaceutical composition according to claim 1, and treating the subject having genetic homocystinuria or side effect thereof.

14. The method according to claim 13, wherein the second agent comprises at least one of trimethylglycine or derivative thereof, formate, formate salt, and diformylglycerol or derivative thereof.

15. The method according to claim 13, wherein administering the composition comprises administering the composition 2-5 times per day per dose to the subject.

16. The method according to claim 13, wherein the subject is evaluated for levels of at least one of homocysteine and polyamines before, during and after administering the pharmaceutical composition, to assess efficacy of dosing regimens to the subject.

17. The method according to claim 13, wherein administering the composition comprises administering orally, intravenously, subcutaneously, intra-rectally, topically, dropwise, by rapid or slow-release patch, or other suitable mode of administration to the subject.

18. The method according to claim 13, wherein the genetic homocystinuria comprises classical cystathionine beta-synthase (CBS) deficient homocystinuria (HCU) or other genetic forms of homocystinuria due to mutations in either methylenetetrahydrofolate reductase or methionine synthase or deficiencies in cobalamin transport and/or metabolism (referred to as remethylation disorders (RD)) in the subject.

19. The method according to claim 13, wherein the side effects comprise one or more of hypercoagulation, stroke and thrombosis.

20. A kit comprising the composition according to claim 1, and at least one container.

* * * * *

SEQUENCE LISTING

```
Sequence total quantity: 12
SEQ ID NO: 1             moltype = DNA  length = 22
FEATURE                  Location/Qualifiers
misc_feature             1..22
                         note = Synthetic sequence; MTR Forward Primer
source                   1..22
                         mol_type = other DNA
                         organism = synthetic construct
SEQUENCE: 1
gctctgtgaa gacctcatct gg                                           22

SEQ ID NO: 2             moltype = DNA  length = 22
FEATURE                  Location/Qualifiers
misc_feature             1..22
                         note = Synthetic sequence; MTR Reverse Primer
source                   1..22
                         mol_type = other DNA
                         organism = synthetic construct
SEQUENCE: 2
gagccattcc tccactcatc tg                                           22

SEQ ID NO: 3             moltype = DNA  length = 23
FEATURE                  Location/Qualifiers
misc_feature             1..23
                         note = Synthetic sequence; MAT1A Forward Primer
source                   1..23
                         mol_type = other DNA
                         organism = synthetic construct
SEQUENCE: 3
ccttctctgg aaaggactac acc                                          23

SEQ ID NO: 4             moltype = DNA  length = 22
FEATURE                  Location/Qualifiers
misc_feature             1..22
                         note = Synthetic sequence; MAT1A Reverse Primer
source                   1..22
                         mol_type = other DNA
                         organism = synthetic construct
SEQUENCE: 4
gacagaggtt ctgccacacc aa                                           22

SEQ ID NO: 5             moltype = DNA  length = 22
FEATURE                  Location/Qualifiers
misc_feature             1..22
                         note = Synthetic sequence; GNMT Forward Primer
source                   1..22
                         mol_type = other DNA
                         organism = synthetic construct
SEQUENCE: 5
tggtgatcga ccaccgcaac ta                                           22

SEQ ID NO: 6             moltype = DNA  length = 23
FEATURE                  Location/Qualifiers
misc_feature             1..23
                         note = Synthetic sequence; GNMT Reverse Primer
source                   1..23
                         mol_type = other DNA
                         organism = synthetic construct
SEQUENCE: 6
gtcgtaatgt ccttggtcag gtc                                          23

SEQ ID NO: 7             moltype = DNA  length = 22
FEATURE                  Location/Qualifiers
misc_feature             1..22
                         note = Synthetic sequence; SAHH Forward Primer
source                   1..22
                         mol_type = other DNA
                         organism = synthetic construct
SEQUENCE: 7
caggctatgg tgatgtgggc aa                                           22
```

-continued

```
SEQ ID NO: 8            moltype = DNA  length = 22
FEATURE                 Location/Qualifiers
misc_feature            1..22
                        note = Synthetic sequence; SAHH Reverse Primer
source                  1..22
                        mol_type = other DNA
                        organism = synthetic construct
SEQUENCE: 8
cctccttaca ggcttcgtcc at                                           22

SEQ ID NO: 9            moltype = DNA  length = 22
FEATURE                 Location/Qualifiers
misc_feature            1..22
                        note = Synthetic sequence; MTHFR Forward Primer
source                  1..22
                        mol_type = other DNA
                        organism = synthetic construct
SEQUENCE: 9
tacctctctg gagagccgaa tc                                           22

SEQ ID NO: 10           moltype = DNA  length = 22
FEATURE                 Location/Qualifiers
misc_feature            1..22
                        note = Synthetic sequence; MTHFR Reverse Primer
source                  1..22
                        mol_type = other DNA
                        organism = synthetic construct
SEQUENCE: 10
ggctgagagt tgatggtgag ga                                           22

SEQ ID NO: 11           moltype = DNA  length = 22
FEATURE                 Location/Qualifiers
misc_feature            1..22
                        note = Synthetic sequence; SHMT1 Forward Primer
source                  1..22
                        mol_type = other DNA
                        organism = synthetic construct
SEQUENCE: 11
ctggagatgc tgtgtcagaa gc                                           22

SEQ ID NO: 12           moltype = DNA  length = 22
FEATURE                 Location/Qualifiers
misc_feature            1..22
                        note = Synthetic sequence; SHMT1 Reverse Primer
source                  1..22
                        mol_type = other DNA
                        organism = synthetic construct
SEQUENCE: 12
tgaggctcta ccagggcagt at                                           22
```